United States Patent
Edmunds et al.

(10) Patent No.: US 10,556,884 B2
(45) Date of Patent: Feb. 11, 2020

(54) PESTICIDALLY ACTIVE HETEROCYCLIC DERIVATIVES WITH SULPHUR CONTAINING SUBSTITUENTS

(71) Applicant: SYNGENTA PARTICIPATIONS AG, Basel (CH)

(72) Inventors: Andrew Edmunds, Stein (CH); Pierre Joseph Marcel Jung, Stein (CH); Michel Muehlebach, Stein (CH); André Jeanguenat, Stein (CH); Daniel Emery, Stein (CH); Roger Graham Hall, Stein (CH); Vikas Sikervar, Goa (IN); Jagadish Pabba, Goa (IN)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/763,230

(22) PCT Filed: Sep. 21, 2016

(86) PCT No.: PCT/EP2016/072351
§ 371 (c)(1),
(2) Date: Mar. 26, 2018

(87) PCT Pub. No.: WO2017/055147
PCT Pub. Date: Apr. 6, 2017

(65) Prior Publication Data
US 2018/0273512 A1 Sep. 27, 2018

(30) Foreign Application Priority Data

Sep. 28, 2015 (IN) .......................... 3091/DEL/2015

(51) Int. Cl.
*C07D 401/14* (2006.01)
*A01N 43/653* (2006.01)
*C07D 401/04* (2006.01)
*C07D 249/08* (2006.01)

(52) U.S. Cl.
CPC ......... *C07D 401/14* (2013.01); *A01N 43/653* (2013.01); *C07D 249/08* (2013.01); *C07D 401/04* (2013.01)

(58) Field of Classification Search
CPC .. C07D 401/04; C07D 401/14; C07D 249/08; A01N 43/653
See application file for complete search history.

(56) References Cited

U.S. PATENT DOCUMENTS 8,178,546 B2 * 5/2012 Aster ................... C07D 403/04
514/266.4

FOREIGN PATENT DOCUMENTS

| JP | H0892224 A | 4/1996 |
|---|---|---|
| WO | 2000/24735 A1 | 5/2000 |
| WO | 2015/144826 A1 | 10/2015 |

OTHER PUBLICATIONS

International Search Report and Written Opinion for PCT/EP2016/072351, dated Dec. 19, 2016.

* cited by examiner

*Primary Examiner* — John Pak
*Assistant Examiner* — Nathan W Schlientz
(74) *Attorney, Agent, or Firm* — Baker & Hostetler, LLP; Toni-Junell Herbert

(57) ABSTRACT

Compounds of formula (I), wherein the substituents are as defined in claim 1, and the agrochemically acceptable salts salts, stereoisomers, enantiomers, tautomers and N-oxides of those compounds, can be used as insecticides and can be prepared in a manner known per se.

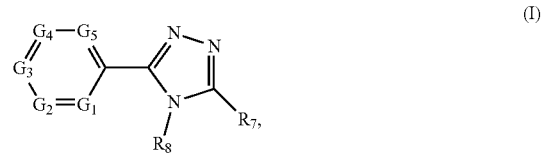

(I)

19 Claims, No Drawings

PESTICIDALLY ACTIVE HETEROCYCLIC DERIVATIVES WITH SULPHUR CONTAINING SUBSTITUENTS

CROSS-REFERENCE TO RELATED APPLICATIONS

This application is a 371 National Stage application of International Application No. PCT/EP2016/072351, filed Sep. 21, 2016, which claims priority to Indian Patent Application No. 3091/DEL/2015, filed Sep. 28, 2015, the entire contents of which are hereby incorporated by reference.

The present invention relates to pesticidally active, in particular insecticidally active heterocyclic derivatives containing sulphur substituents, to processes for their preparation, to compositions comprising those compounds, and to their use for controlling animal pests, including arthropods and in particular insects or representatives of the order Acarina.

Heterocyclic compounds with pesticidal action are known and described, for example, in WO 2010/125985 and WO 2013/018928. There have now been found novel pesticidally active heterocyclic triazole derivatives with sulphur containing amino derivative substituents.

The present invention accordingly relates to compounds of formula I,

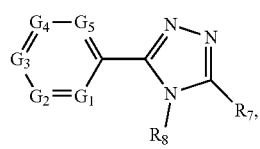

(I)

wherein $G_1$ is nitrogen or $CR_2$;

$G_2$ is nitrogen or $CR_3$;

$G_3$ is nitrogen or $CR_4$;

$G_4$ is nitrogen or $CR_5$;

$G_5$ is nitrogen or $CR_6$, with the proviso that not more than 2 nitrogen as G may follow consecutively;

$R_2$, $R_3$, $R_4$, $R_5$ and $R_6$ are, independently from each other, hydrogen, halogen, $C_1$-$C_6$haloalkyl or $C_1$-$C_6$alkyl; or $R_2$, $R_3$, $R_4$, $R_5$ and $R_6$ are, independently from each other, $C_1$-$C_6$haloalkylsulfanyl, $C_1$-$C_6$haloalkylsulfinyl, $C_1$-$C_6$haloalkylsulfonyl, $C_1$-$C_6$alkylsulfanyl, $C_1$-$C_6$alkylsulfinyl, $C_1$-$C_6$alkylsulfonyl, $C_1$-$C_6$alkoxy, $C_1$-$C_6$haloalkoxy, $C_1$-$C_4$haloalkoxy$C_1$-$C_4$alkyl, $C_1$-$C_4$alkoxy$C_1$-$C_4$alkyl, $SF_5$, cyano, $C_3$-$C_6$cycloalkyl$C_1$-$C_4$alkyl or —C(O)$C_1$-$C_6$haloalkyl; or $R_2$, $R_3$, $R_4$, $R_5$ and $R_6$ are, independently from each other, $C_3$-$C_6$cycloalkyl which can be mono- or polysubstituted by substituents selected from the group consisting of halogen, cyano, $C_1$-$C_4$haloalkyl and $C_1$-$C_4$alkyl;

$R_8$ is hydrogen, $C_1$-$C_6$alkyl, $C_1$-$C_6$haloalkyl or $C_1$-$C_4$alkyl substituted by $C_1$-$C_4$alkylsulfanyl;

$R_7$ is a radical selected from the group consisting of formula $Q_1$, $Q_2$, $Q_3$, $Q_4$, $Q_5$, $Q_6$, $Q_7$, $Q_8$, $Q_9$, $Q_{10}$, $Q_{11}$, $Q_{12}$, $Q_{13}$ and $Q_{14}$

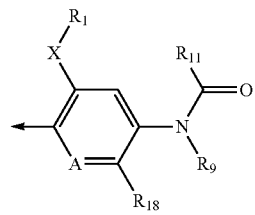

$Q_1$

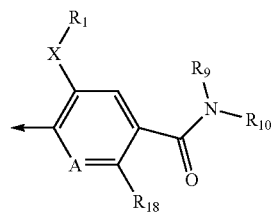

$Q_2$

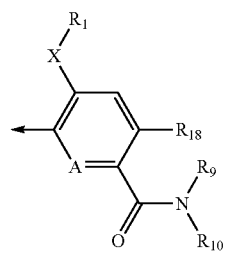

$Q_3$

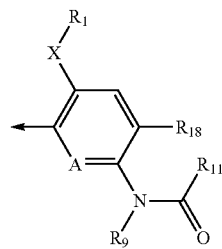

$Q_4$

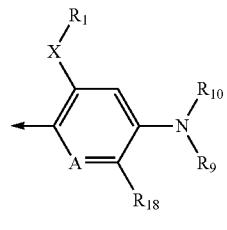

$Q_5$

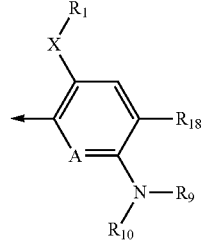

$Q_6$

Q7
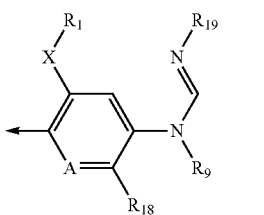

Q8
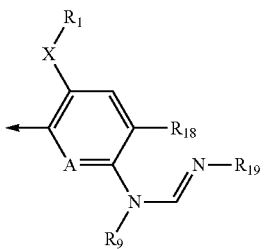

Q9
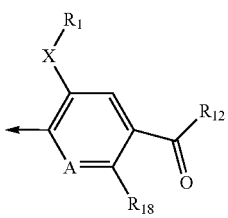

Q10
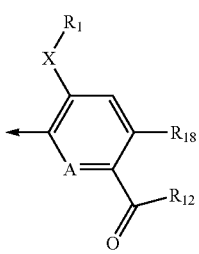

Q11
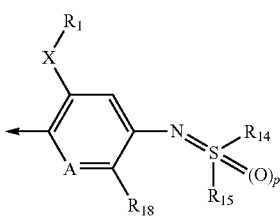

Q12
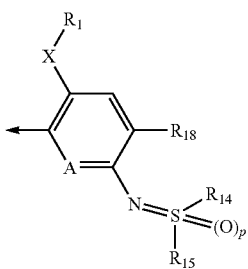

Q13
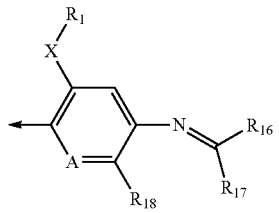

Q14
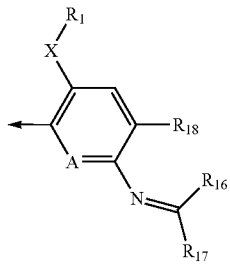

wherein the arrow denotes the point of attachment to the triazole ring;

A represents CH or N;
X is S, SO or $SO_2$;
$R_1$ is $C_1$-$C_4$alkyl or $C_1$-$C_4$haloalkyl; or
$R_1$ is $C_3$-$C_6$cycloalkyl which can be mono- or polysubstituted by substituents selected from the group the group consisting of halogen, $C_1$-$C_4$haloalkyl, cyano and $C_1$-$C_4$alkyl;
$R_9$ is hydrogen, $C_1$-$C_6$alkyl, $C_1$-$C_6$haloalkyl, $C_1$-$C_4$alkoxy$C_1$-$C_4$alkyl, hydroxyl or $C_1$-$C_6$alkoxy, S(O)$mR_{13}$; or
$R_9$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or
$R_9$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;
$R_{10}$ is hydrogen, $C_1$-$C_6$alkyl, cyano, $C_1$-$C_6$alkoxy, $C_1$-$C_6$haloalkoxy, $C_2$-$C_6$alkynyl, $C_2$-$C_6$alkenyl, amino, NH—CN, N—($C_1$-$C_4$ alkyl)amino, N—($C_1$-$C_4$ alkyl)N—($C_1$-$C_4$ alkyl)amino, N—($C_3$-$C_6$cycloalkyl)amino, N—($C_1$-$C_4$alkyl)N—($C_3$-$C_6$cycloalkyl)amino, N—($C_1$-$C_4$alkylcarbonyl)amino, N—($C_1$-$C_4$alkyl)N—($C_1$-$C_4$alkylcarbonyl)amino, N—($C_1$-$C_4$ alkyl)N—($C_3$-$C_6$cycloalkylcarbonyl)amino, N—($C_3$-$C_6$cycloalkylcarbonyl)amino, N—($C_1$-$C_4$alkylcarbonyl)N—($C_3$-$C_6$cycloalkyl)amino or —S(O)$mR_{13}$; or
$R_{10}$ is $C_1$-$C_4$alkyl mono- or polysubstituted by substituents independently selected from the group Z; or
$R_{10}$ is a five- to six-membered ring aromatic or heteroaromatic system, said aromatic or heteroaromatic ring system can contain 1 to 4 hetero atoms selected from the group consisting of nitrogen, oxygen and sulfur, with the proviso that each ring system cannot contain more than 2 oxygen atoms and more than 2 sulfur atoms, said five- to six-membered ring system can be mono- or polysubstituted by substituents independently selected from the group V;
$R_{11}$ is hydrogen, $C_1$-$C_6$alkyl, $C_1$-$C_6$alkoxy, $C_1$-$C_6$haloalkoxy, amino, N—$C_1$-$C_4$alkylamino, N—($C_1$-$C_4$ alkyl)N—($C_3$-$C_6$cycloalkyl)amino, N—($C_3$-$C_6$cycloalkyl)amino or N—($C_1$-$C_4$ alkyl)-N—($C_1$-$C_4$ alkyl)amino; or $R_{11}$ is $C_1$-$C_4$alkyl mono- or polysubstituted by substituents independently selected from the group Z; or $R_{11}$ is $C_3$-$C_6$cycloalkyl which can be mono—or polysubstituted by substituents selected from the group consisting of halogen, $C_1$-$C_4$haloalkyl, cyano and $C_1$-$C_4$alkyl; or $R_{11}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl; or $R_{11}$ is a five- to six-membered aromatic or heteroaromatic ring system, said aromatic or heteroaromatic ring system can contain 1 to 4 hetero atoms selected from the group consisting of nitrogen, oxygen and sulfur, with the proviso that each ring system cannot contain more than 2 oxygen atoms and more than 2 sulfur atoms, said five- to six-membered aromatic or heteroaromatic ring system can be mono- or polysubstituted by substituents independently selected from the group V;

$R_{12}$ is hydrogen, $C_1$-$C_6$ alkyl, $C_1$-$C_6$alkoxy, hydroxy or $C_1$-$C_6$ haloalkoxy; or $R_{12}$ is $C_1$-$C_4$alkyl mono- or polysubstituted by substituents independently selected from the group Z; or $R_{12}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{12}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;

$R_{13}$ is $C_1$-$C_4$alkyl, $C_1$-$C_4$haloalkyl, N—$C_1$-$C_4$alkylamino, N,N—($C_1$-$C_4$ alkyl)$_2$amino or phenyl; said phenyl can be mono- or polysubstituted by substituents selected from the group consisting of halogen, $C_1$-$C_4$alkyl, cyano, $C_1$-$C_4$haloalkyl and $C_1$-$C_4$alkoxy; or $R_{13}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{13}$ is $C_3$-$C_6$cycloalkyl$C_1$-$C_4$alkyl which can be mono- or polysubstituted by substituents selected from the group consisting of halogen, $C_1$-$C_4$haloalkyl, cyano and $C_1$-$C_4$alkyl;

m is 0, 1 or 2;

$R_{14}$ is hydrogen or $C_1$-$C_6$ alkyl;

$R_{15}$ is hydrogen, $C_1$-$C_6$ alkyl, $C_1$-$C_6$alkoxy, $C_1$-$C_6$ haloalkoxy, amino, N—$C_1$-$C_4$alkylamino or N,N—($C_1$-$C_4$ alkyl)$_2$amino; or $R_{15}$ is $C_1$-$C_4$alkyl mono- or polysubstituted by substituents independently selected from the group Z; or $R_{15}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{15}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;

p is 0 or 1;

$R_{16}$ is hydrogen or $C_1$-$C_6$ alkyl;

$R_{17}$ is hydrogen, $C_1$-$C_6$alkyl, $C_1$-$C_6$haloalkyl, $C_1$-$C_6$alkoxy or $C_1$-$C_6$ haloalkoxy; or $R_{17}$ is amino which can be mono- or disubstituted by substituents selected from the group consisting of cyano, $C_1$-$C_6$alkyl, $C_1$-$C_6$alkoxy, $C_1$-$C_6$haloalkoxy, $C_3$-$C_6$cycloalkyl and $C_3$-$C_6$cycloalkyl-$C_1$-$C_4$alkyl, said $C_3$-$C_6$cycloalkyl and $C_3$-$C_6$cycloalkyl-$C_1$-$C_4$alkyl groups itself can be mono- or polysubstituted by substituents selected from the group consisting of halogen, $C_1$-$C_4$haloalkyl, cyano and $C_1$-$C_4$alkyl; or $R_{17}$ is $C_1$-$C_4$alkyl mono- or polysubstituted by substituents independently selected from the group Z; or $R_{17}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{17}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl; or $R_{17}$ is a five- to six-membered ring aromatic or heteroaromatic ring system, said aromatic or heteroaromatic ring system can contain 1 to 4 hetero atoms selected from the group consisting of nitrogen, oxygen and sulfur, with the proviso that each ring system cannot contain more than 2 oxygen atoms and more than 2 sulfur atoms, said five- to six-membered aromatic or heteroaromatic ring system can be mono- to polysubstituted by substituents independently selected from the group V;

$R_{18}$ is hydrogen, halogen, $C_1$-$C_4$haloalkyl, amino, cyano, $C_1$-$C_4$alkyl, $C_3$-$C_6$cycloalkyl, $C_1$-$C_4$haloalkyl or is $C_3$-$C_6$cycloalkyl mono-, di- or tri-substituted by substituents selected from the group consisting of halogen, $C_1$-$C_4$haloalkyl, cyano and $C_1$-$C_4$alkyl;

$R_{19}$ is hydrogen, $C_1$-$C_6$alkyl, $C_1$-$C_6$alkoxy, $C_1$-$C_6$haloalkoxy, $C_3$-$C_6$cycloalkyl$C_1$-$C_4$alkyl, $C_3$-$C_6$cycloalkyl;

Z is cyano, halogen, hydroxy, —SH, amino, nitro, $C_1$-$C_4$alkoxy, $C_1$-$C_4$haloalkoxy, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl or phenyl; said phenyl can be mono- or polysubstituted by substituents selected from the group consisting of halogen, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, cyano, $C_1$-$C_4$haloalkyl and $C_1$-$C_4$alkyl; or Z is pyridyl; said pyridyl can be mono- or polysubstituted by substituents selected from the group consisting of halogen, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, cyano, $C_1$-$C_4$haloalkyl and $C_1$-$C_4$alkyl; or Z is pyrimidyl; said pyrimidinyl can be mono- or polysubstituted by substituents selected from the group consisting of halogen, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, cyano, $C_1$-$C_4$haloalkyl and $C_1$-$C_4$alkyl; and V is cyano, halogen, $C_1$-$C_4$alkyl, $C_3$-$C_6$ cycloalkyl, $C_1$-$C_4$alkoxy, $C_1$-$C_4$alkoxy$C_1$-$C_4$alkyl, $C_1$-$C_4$haloalkyl, $C_1$-$C_4$haloalkoxy, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl or $C_1$-$C_4$haloalkylsulfonyl; and agrochemically acceptable salts, stereoismers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

The cycloalkyl groups preferably have from 3 to 6 ring carbon atoms, for example cyclopropyl, cyclobutyl, cyclopentyl and cyclohexyl.

Haloalkoxy groups preferably have a chain length of from 1 to 4 carbon atoms. Haloalkoxy is, for example, difluoromethoxy, trifluoromethoxy or 2,2,2-trifluoroethoxy.

Haloalkylsulfanyl groups preferably have a chain length of from 1 to 4 carbon atoms. Haloalkylsulfanyl is, for example, difluoromethylsulfanyl, trifluoromethylsulfanyl or 2,2,2-trifluoroethylsulfanyl. Similar considerations apply to the radicals $C_1$-$C_4$haloalkylsulfinyl and $C_1$-$C_4$haloalkylsulfonyl, which may be, for example, trifluoromethylsulfinyl, trifluoromethylsulfonyl or 2,2,2-trifluoroethylsulfonyl.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

The compounds of formula I according to the invention also include hydrates which may be formed during the salt formation.

According to the present invention, a five- to six-membered aromatic or heteroaromaticring system, which can contain 1 to 4 hetero atoms selected from the group consisting of nitrogen, oxygen and sulfur, it not being possible for each ring system to contain more than 2 oxygen atoms and more than 2 sulfur atoms, are preferably selected from the group consisting of the following aromatic or heteroaromatic groups: phenyl, pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl, pyranyl; (1H-pyrrol-1-yl)-; (1H-pyrrol-2-yl)-; (1H-pyrrol-3-yl)-; (1H-pyrazol-1-yl)-; (1H-pyrazol-3-yl)-; (3H-pyrazol-3-yl)-; (1H-pyrazol-4-yl)-; (3-isoxazolyl)-; (5-isoxazolyl)-; (2-furanyl)-; (3-furanyl)-; (2-thienyl)-; (3-thienyl)-; (1H-imidazol-2-yl)-; (1H-imidazol-4-yl)-; (1H-imidazol-5-yl)-; (2-oxazol-2-yl)-; (oxazol-4-yl)-; (oxazol-5-yl)-; (thiazol-2-yl)-; (thiazol-4-yl)-; (thiazol-5-yl)-; (isothiazol-3-yl)-; (isothiazol-5-yl)-; (1H-1,2,3-triazol-1-yl)-; (1H-1,2,4-triazol-3-yl)-; (4H-1,2,4-triazol-4-yl)-; (1H-1,2,4-triazol-1-yl)-; (1,2,3-oxadiazol-2-yl)-; (1,2,4-oxadiazol-3-yl)-; (1,2,4-oxadiazol-4-yl)-; (1,2,4-oxadiazol-5-yl)-; (1,2,3-thiadiazol-2-yl)-; (1,2,4-thiadiazol-3-yl)-; (1,2,4-thiadiazol-4-yl)-; (1,3,4-thiadiazol-5-yl)-; (1H-tetrazol-1-yl)-; (1H-tetrazol-5-yl)-; (2H-tetrazol-5-yl)-; (2-pyridyl)-; (3-pyridyl)-; (4-pyridyl)-; (2-pyrimidinyl)-; (4-pyrimidinyl)-; (5-pyrimidinyl)-; (2-pyrazinyl)-; (3-pyridazinyl)-; (4-pyridazinyl)-; (1,3,5-triazin-2-yl)-; (1,2,4-triazin-5-yl)-; (1,2,4-triazin-6-yl)-; and (1,2,4-triazin-3-yl)-; (furazan-3-yl)-.

Preferably in the compounds of formula I,
$R_9$ is hydrogen, $C_1$-$C_6$alkyl, $C_1$-$C_6$haloalkyl, $C_1$-$C_4$alkoxy$C_1$-$C_4$alkyl, hydroxyl or $C_1$-$C_6$alkoxy; or $R_9$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or
$R_9$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;
V is cyano, halogen, $C_1$-$C_4$alkoxy, $C_1$-$C_4$alkoxy$C_1$-$C_4$ alkyl, $C_1$-$C_4$haloalkyl, $C_1$-$C_4$haloalkoxy, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl or $C_1$-$C_4$haloalkylsulfonyl; and
$R_{18}$ is hydrogen, halogen, amino, cyano, $C_1$-$C_4$alkyl or $C_1$-$C_4$haloalkyl.

A preferred group of compounds of formula I is represented by the compounds of formula I-1

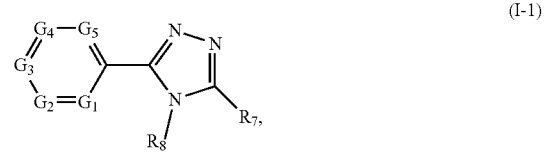

(I-1)

wherein $R_7$ is a radical selected from the group consisting of formulae $Q_1$, $Q_2$, $Q_3$, $Q_4$, $Q_5$, $Q_6$, $Q_7$, $Q_8$, $Q_9$, $Q_{10}$, $Q_{11}$, $Q_{12}$, $Q_{13}$ and $Q_{14}$
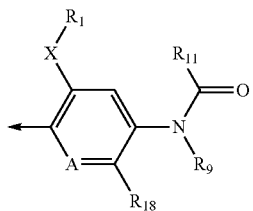
$Q_1$
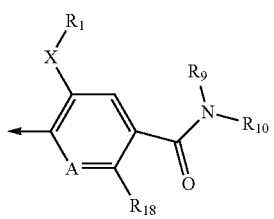
$Q_2$
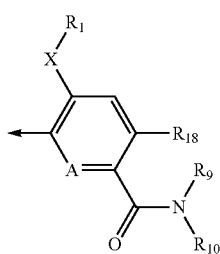
$Q_3$
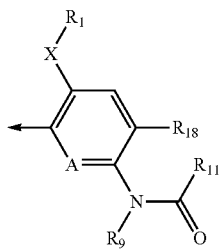
$Q_4$
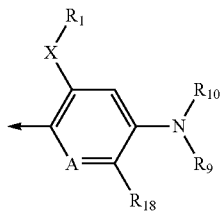
$Q_5$
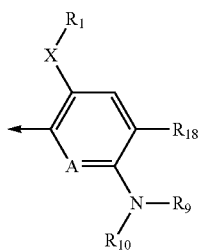
$Q_6$
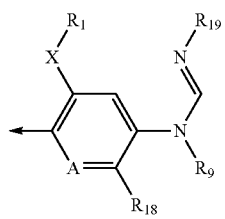
$Q_7$
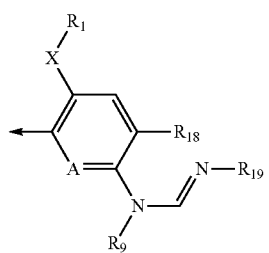
$Q_8$
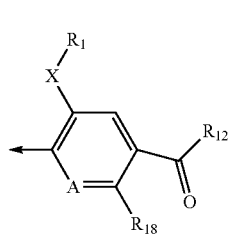
$Q_9$
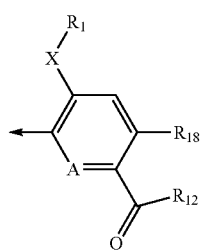
$Q_{10}$
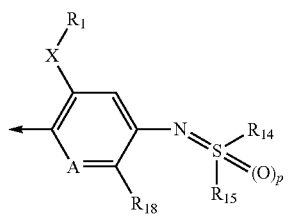
$Q_{11}$
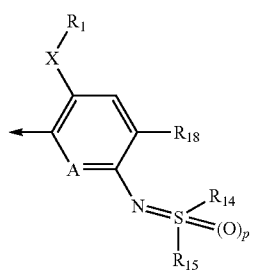
$Q_{12}$

Q13

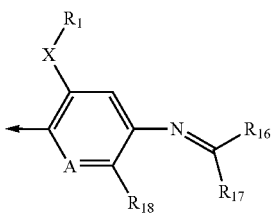

Q14

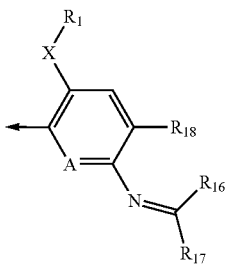

wherein A, $G_1$, $G_2$, $G_3$, $G_4$, $G_5$, $R_9$, $R_{10}$, $R_{11}$, $R_{12}$, $R_{14}$, $R_{15}$, $R_{16}$, $R_{17}$, $R_{18}$ and $R_{19}$ are as defined under formula I above; and wherein X is S, SO or $SO_2$; $R_1$ is methyl, ethyl, n-propyl, i-propyl or cyclopropylmethyl, preferably ethyl; and $R_8$ is as defined above under formula I, preferably methyl, and agrochemically acceptable salts, stereoismers, enantiomers, tautomers and N-oxides of those compounds.

Also preferred are compounds of formula I-1, wherein $G_1$ is N; $G_4$ is $C(C_1\text{-}C_4\text{haloalkyl})$; and $G_2$, $G_3$ and $G_5$ are CH.

In an especially preferred group of compounds of formula I-1, $G_1$ is N; $G_4$ is $C(CF_3)$; and $G_2$, $G_3$ and $G_5$ are CH.

In said especially preferred group of compounds of formula I-1, $R_8$ is preferably methyl. A further preferred embodiment of said especially preferred group of compounds of formula I-1 comprises compounds of formula I-1, wherein A is preferably N; X is preferably S or $SO_2$ and $R_1$ is preferably ethyl.

In compounds of formula I-1 and all of the preferred embodiments of compounds of formula I-1 mentioned above, $R_7$ is preferably selected from the group Q consisting of $Q_1$ to $Q_6$

Q1

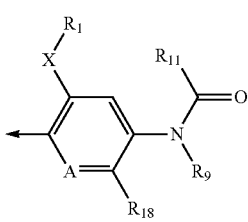

Q2

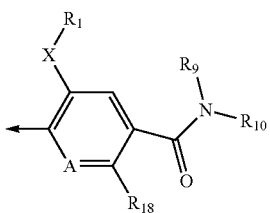

Q3

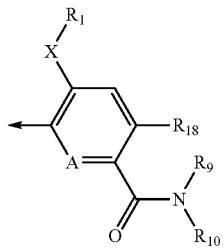

Q4

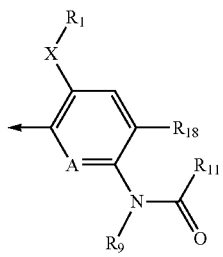

Q5

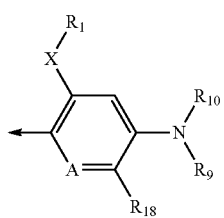

Q6

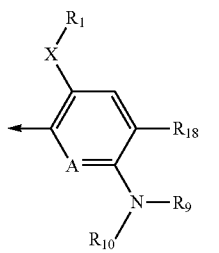

wherein $R_{18}$ is hydrogen; A, $R_9$, $R_{10}$ and $R_{11}$ are as defined under formula I above; X is S, SO or $SO_2$; $R_1$ is methyl, ethyl, n-propyl, i-propyl or cyclopropylmethyl, preferably ethyl; and $R_8$ is as defined above under formula I, preferably methyl, and agrochemically acceptable salts, stereoismers, enantiomers, tautomers and N-oxides of those compounds.

Another preferred group of compounds of formula I is represented by the compounds of formula I-2

(I-2)

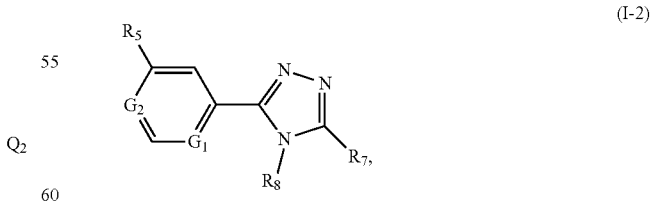

wherein $G_1$, $G_2$, $R_5$, $R_7$ and $R_8$ are as defined under formula I above; and agrochemically acceptable salts, stereoismers, enantiomers, tautomers and N-oxides of those compounds.

Also preferred are compounds of formula I-2, wherein $G_1$, $G_2$, $R_5$ and $R_8$ are as defined under formula I above; $R_7$ is preferably selected from the group Q consisting of $Q_1$ to $Q_6$

Q1

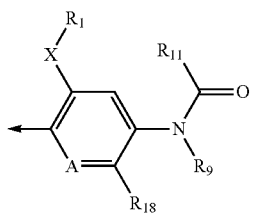

Q2

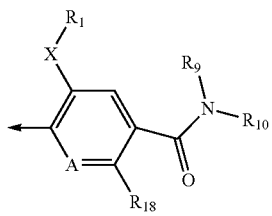

Q3

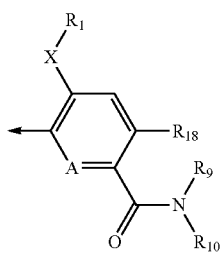

Q4

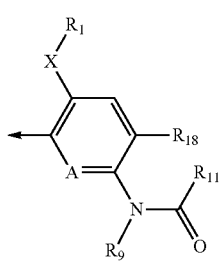

Q5

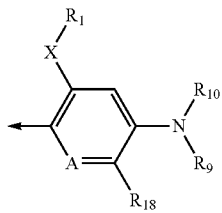

Q6

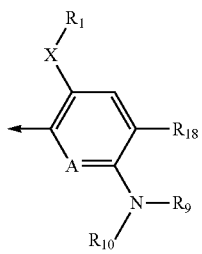

$R_{18}$ is hydrogen; X is S, SO or $SO_2$; and $R_1$ is methyl, ethyl, n-propyl, i-propyl or cyclopropylmethyl, preferably ethyl; and $R_8$ is as defined above under formula I, preferably methyl; and agrochemically acceptable salts, stereoismers, enantiomers, tautomers and N-oxides of those compounds.

A further preferred embodiment of the invention comprises compounds of formula I represented by the compounds of formula I-3

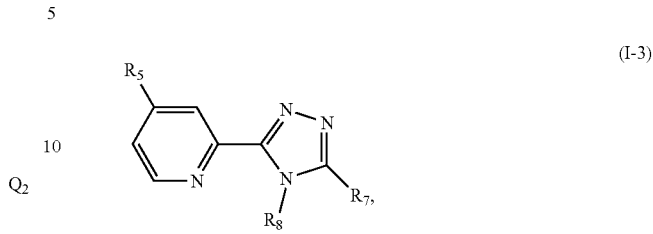

(I-3)

wherein
$R_5$ is $C_1$-$C_4$ haloalkyl, in particular trifluoromethyl;
$R_8$ is $C_1$-$C_4$ alkyl, in particular methyl;
$R_7$ is selected from the group consisting of $Q_1$ to $Q_6$

Q1

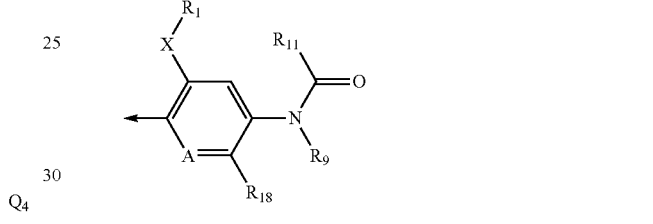

Q2

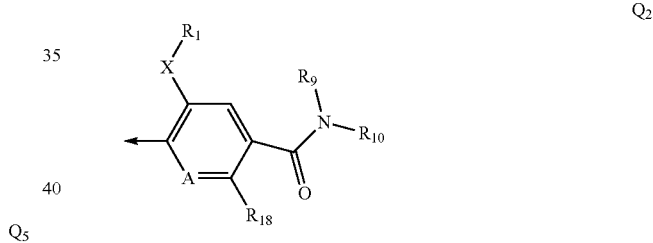

Q3

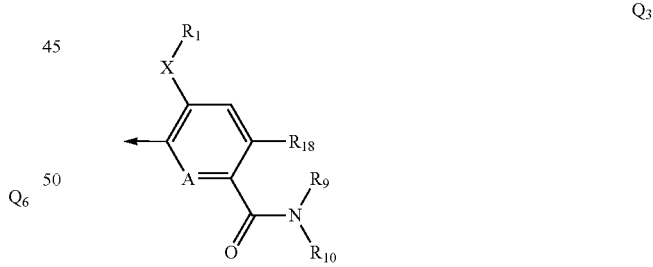

Q4

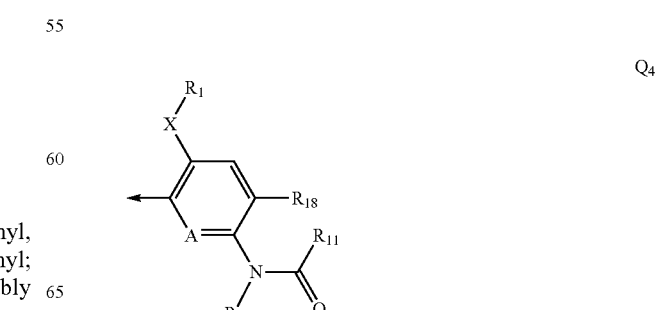

-continued

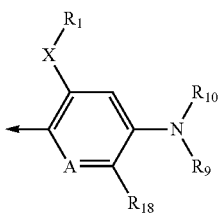

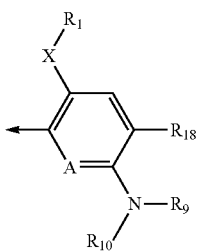

wherein
$R_1$ is $C_1$-$C_4$ alkyl, in particular ethyl;
X is S, SO or $SO_2$, in particular S or $SO_2$;
$R_9$, $R_{10}$ and $R_{11}$ are as defined under formula I in claim 1;
$R_{18}$ is hydrogen; and
A is N or CH; and agrochemically acceptable salts, stereoisomers, enantiomers, tautomers and N-oxides of the compounds of formula I-3.

More preferred are compounds of formula I-3, wherein
A is N or CH;
$R_5$ is $C_1$-$C_4$haloalkyl, in particular trifluoromethyl;
X is S, SO or $SO_2$, in particular S or $SO_2$;
$R_7$ is selected from the group consisting of $Q_1$ to $Q_6$ $Q_1$
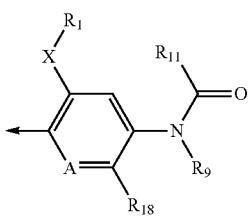

$Q_2$
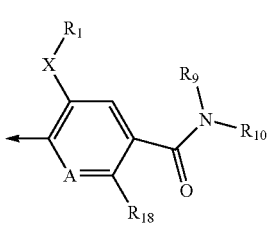

$Q_3$
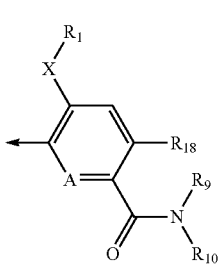

-continued $Q_4$
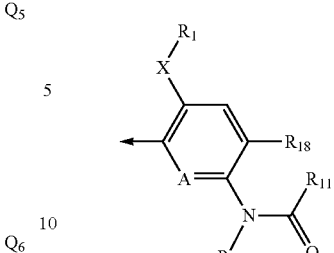

$Q_5$
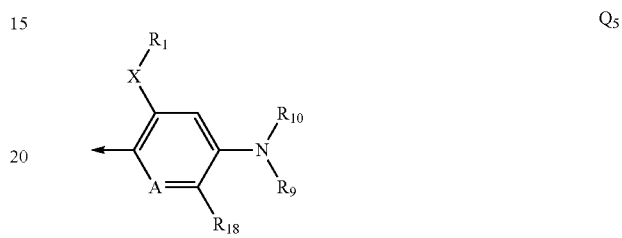

$Q_6$
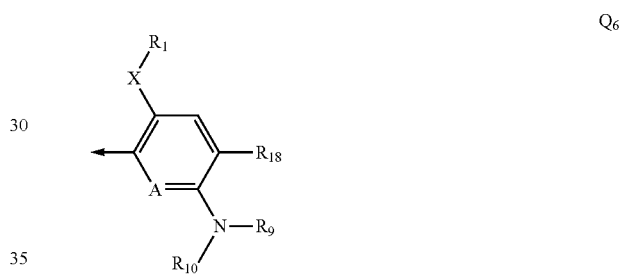

wherein $R_{18}$ is hydrogen; $R_1$ is $C_1$-$C_4$ alkyl, in particular ethyl;

$R_8$ is $C_1$-$C_4$ alkyl, in particular methyl;

$R_9$ is hydrogen or $C_1$-$C_4$alkyl; or $R_9$ is $C_3$-$C_6$cycloalkyl which can be mono—or polysubstituted by substituents selected from the group consisting of halogen, $C_1$-$C_4$haloalkyl, cyano and $C_1$-$C_4$alkyl;

$R_{10}$ is hydrogen, $C_1$-$C_6$alkyl, cyano, N—($C_1$-$C_4$ alkyl)N—($C_3$-$C_6$cycloalkylcarbonyl)amino, N—$C_3$-$C_6$cycloalkylcarbonylamino or —S(O)$_2$R$_{13}$; or $R_{10}$ is $C_1$-$C_4$alkyl mono- or disubstituted by a group selected from cyano and halogen; or $R_{10}$ is phenyl, pyridinyl or pyrazolyl; said phenyl, pyridinyl or pyrazolyl can be mono to polysubstituted by substituents independently selected from $C_1$-$C_4$haloalkyl and halogen;

$R_{13}$ is $C_1$-$C_4$alkyl, N—$C_1$-$C_4$alkylamino or N,N—($C_1$-$C_4$alkyl)$_2$amino;

and agrochemically acceptable salts, stereoisomers, enantiomers, tautomers and N-oxides of the compounds of formula I-3.

Even more preferred compounds of formula I-3, are those, wherein
A is N or CH;
$R_5$ is $C_1$-$C_4$haloalkyl, in particular trifluoromethyl;
X is S, SO or $SO_2$, in particular S or $SO_2$;

$R_7$ is selected from the group consisting of $Q_1$ to $Q_6$

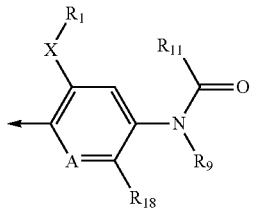
$Q_1$

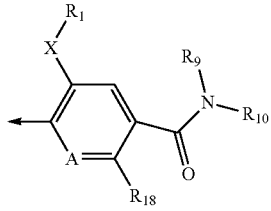
$Q_2$

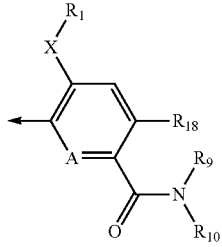
$Q_3$

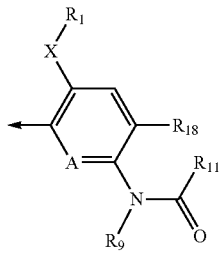
$Q_4$

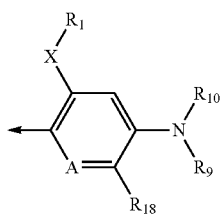
$Q_5$

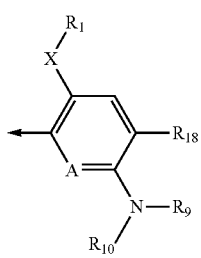
$Q_6$ wherein $R_{18}$ is hydrogen; $R_1$ is $C_1$-$C_4$ alkyl, in particular ethyl;
$R_8$ is $C_1$-$C_4$ alkyl, in particular methyl;
$R_9$ is hydrogen, $C_1$-$C_4$alkyl or $C_3$-$C_6$cycloalkyl, in particular hydrogen, methyl or cyclopropyl;
$R_{10}$ is hydrogen, $C_1$-$C_6$alkyl; in particular hydrogen and methyl;
$R_{11}$ is $C_1$-$C_6$alkyl, $C_3$-$C_6$cycloalkyl which can be mono— or polysubstituted by substituents selected from the group consisting of halogen, $C_1$-$C_4$haloalkyl, cyano and $C_1$-$C_4$alkyl; in particular hydrogen, methyl and cyclopropyl.

In an outstanding group of compounds of formula I, the ring, which is formed by the groups $G_1$ to $G_5$ represents pyridyl, in particular 2-pyridyl, which can be substituted by $C_1$-$C_4$haloalkyl;
$R_7$ is pyridyl, in particular 2-pyridyl, which is substituted by ethylsulfonyl, preferably at the 6-position of the pyridine ring; and which can be further substituted by substituents selected from the group consisting of $C_2$-$C_6$alkenyl, —CHO, $C_1$-$C_6$alkylcarbonyl, $C_3$-$C_6$cycloalkylcarbonylamino and $C_3$-$C_6$cycloalkylamino; and
$R_8$ is $C_1$-$C_4$alkyl, preferably methyl.

Even more preferred are compounds of formula I represented by the compounds of formula I-16

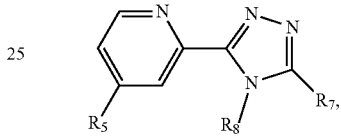
(I-16)

wherein
$R_8$ is $C_1$-$C_3$alkyl;
A is N or CH;
$R_5$ is $C_1$-$C_4$haloalkyl;
$R_7$ is selected from the group consisting of $Q_1$ to $Q_7$, $Q_9$, $Q_{10}$ and $Q_{11}$

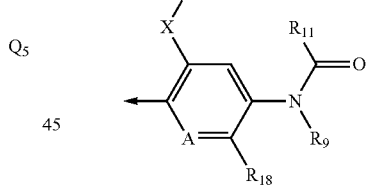
$Q_1$

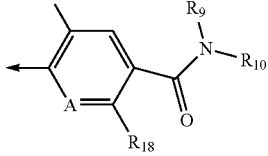
$Q_2$

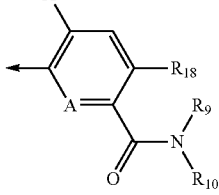
$Q_3$

-continued

Q4 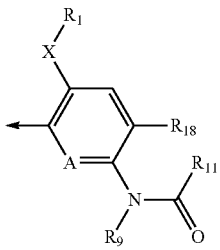

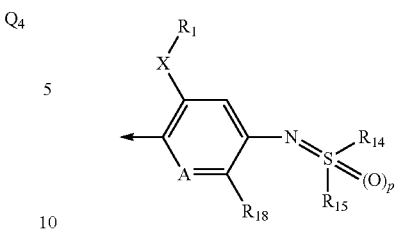

Q5

Q6 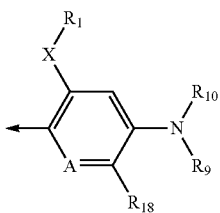

Q7

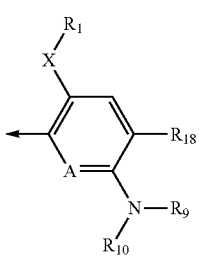

Q9

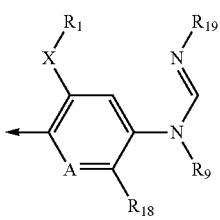

Q10

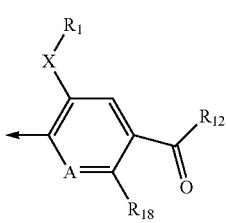

Q11

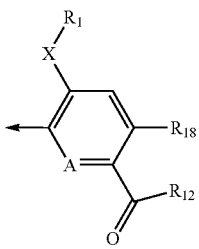

-continued $R_1$ is $C_1$-$C_4$alkyl;

$R_{18}$ is hydrogen or halogen

X is S, SO or $SO_2$, in particular S or $SO_2$;

$R_9$ is hydrogen, $C_1$-$C_4$alkyl, $C_1$-$C_4$haloalkyl, $S(O)mR_{13}$; or $R_9$ is cyclopropyl which can be substituted by cyano;

$R_{10}$ is hydrogen, $C_1$-$C_6$alkyl, amino, N—($C_1$-$C_4$alkyl)N—($C_3$-$C_6$cycloalkylcarbonyl)amino, N—($C_3$-$C_6$cycloalkylcarbonyl)amino or —$S(O)mR_{13}$; or $R_{10}$ is $C_1$-$C_4$alkyl which can be substituted by cyano;

$R_{11}$ is $C_1$-$C_4$alkoxy or cyclopropyl;

$R_{12}$ $C_1$-$C_6$ alkyl or hydroxyl;

$R_{13}$ is $C_1$-$C_4$alkyl or cyclopropyl;

$R_{19}$ is $C_1$-$C_4$alkoxy;

$R_{14}$ is $C_1$-$C_4$ alkyl;

$R_{15}$ is Cyclopropyl;

m is 2 and p is 1.

The process according to the invention for preparing compounds of formula I is carried out by methods known to those skilled in the art. More specifically, the subgroup of compounds of formula I, wherein X is SO (sulfoxide) and/or $SO_2$ (sulfone), may be obtained by means of an oxidation reaction of the corresponding sulfide compounds of formula I, wherein X is S, involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds I to produce the sulfoxide compounds I, and preferably 2 to 2.2 moles of oxidant, relative to 1 mole of of the sulfide compounds I to produce the sulfone compounds I. Such oxidation reactions are disclosed, for example, in WO 2013/018928.

The subgroup of compounds of formula I, wherein X is S (sulfide) and wherein $R_7$, $R_8$, $G_1$, $G_2$, $G_3$, $G_4$, and $G_5$ are as defined above,

Scheme 1

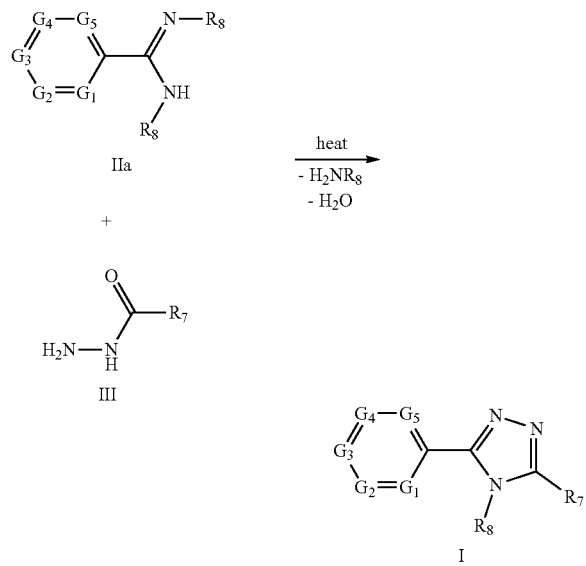

may be prepared by reacting an amidine compound of formula IIa, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, with a hydrazide compound of formula III, or a salt thereof, wherein $R_7$ is as defined above and wherein X is S (sulfide), optionally in presence of a base such as alkali metal carbonates, for example sodium carbonate or potassium carbonate, in a solvent such as methanol, ethanol, isopropanol, acetonitrile, pyridine, acetic acid, N,N-dimethylformamide or N,N-dimethylacetamide, at temperatures between 0 and 200° C., preferably between 50 and 150° C., optionally under microwave irradiation. Such a process may be carried out in analogy to, for example, G. Bonanomi et al., ChemMedChem 2010, 5, 705-715. The compounds of formula IIa may be reacted with any configuration (E or Z, or any mixture thereof) on the carbon-nitrogen double bond.

Alternatively, the subgroup of compounds of formula I, wherein X is S (sulfide) and wherein $R_7$, $R_8$, $G_1$, $G_2$, $G_3$, $G_4$, and $G_5$ are as defined above,

Scheme 2

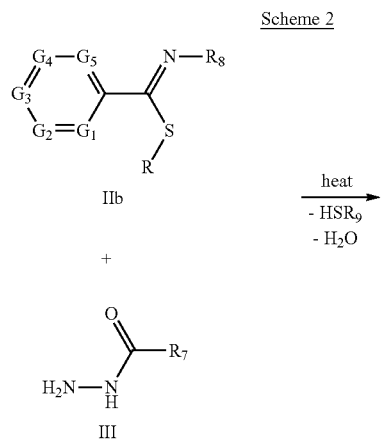

may be prepared by reacting an alkyl carboximidothioate compound of formula IIb, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, and in which R is $C_1$-$C_6$alkyl, with a hydrazide compound of formula III, or a salt thereof, wherein $R_7$ is as defined above and wherein X is S (sulfide), optionally in presence of a base such as alkali metal carbonates, for example sodium carbonate or potassium carbonate, in a solvent such as methanol, ethanol, isopropanol, acetonitrile, pyridine, acetic acid, N,N-dimethylformamide or N,N-dimethyl-acetamide, at temperatures between 0 and 200° C., preferably between 50 and 180° C., optionally under microwave irradiation. Such a process may be carried out in analogy to, for example, M. H. Klingele et al, Eur. J. Org. Chem. 2004, 3422-3434. The compounds of formula IIb may be reacted with any configuration (E or Z, or any mixture thereof) on the carbon-nitrogen double bond.

Compounds of formula IIa, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above,

Scheme 3

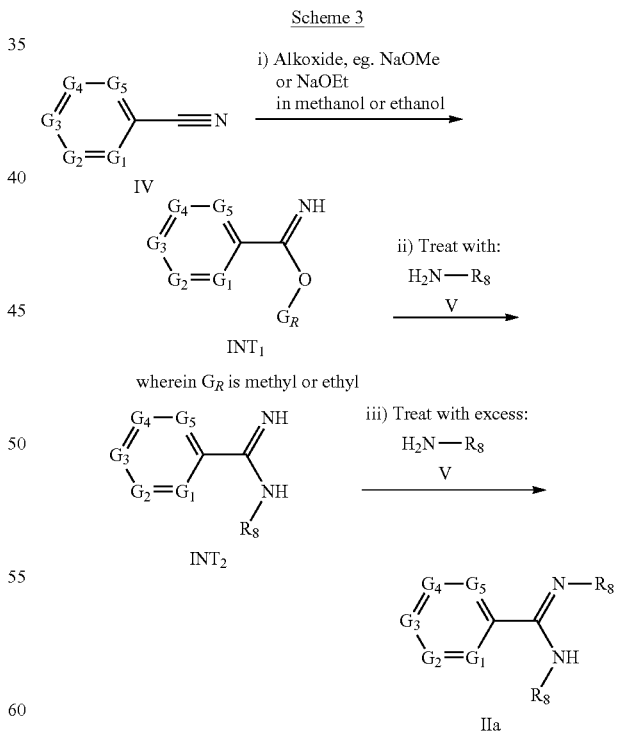

may be prepared by reacting a nitrile compound of formula IV, wherein $G_1$, $G_2$, $G_3$, $G_4$, and $G_5$ are as defined above, sequentially with
i) a catalytic amount (preferably 0.01 to 0.5 equivalent) or an equimolar amount of an alkoxide, preferably sodium methoxide NaOMe or sodium ethoxide NaOEt, in an alcoholic solvent, such as methanol or ethanol, at temperatures between 0 and 100° C., to generate an imidate intermediate of the formula $INT_1$ (or a salt and/or a tautomer thereof); followed by
ii) treatment with an amine reagent of formula V $R_8$—$NH_2$ (V), or a salt thereof (such as a hydrohalide salt, preferably a hydrochloride or a hydrobromide salt, or any other equivalent salt), wherein $R_8$ is as defined above, optionally in the presence of an acid (such as a hydrohalide acid, preferably hydrochloric acid or hydrobromic acid, or any other equivalent acid), at temperatures between 0-180° C., to generate an amidine intermediate of the formula $INT_2$ (or a salt and/or a tautomer thereof); followed by
iii) treatment with an excess of the amine reagent of formula V, or a salt thereof (such as a hydrohalide salt, preferably a hydrochloride or a hydrobromide salt, or any other equivalent salt), wherein $R_8$ is as defined above, preferably in the presence of an acid (such as a hydrohalide acid, preferably hydrochloric acid or hydrobromic acid, or any other equivalent acid), at temperatures between 0-180° C., to form the compound of the formula IIa, or a salt and/or a tautomer thereof. The compounds of formula IIa may be isolated with any configuration (E or Z, or any mixture thereof) on the carbon-nitrogen double bond. Steps ii) and iii) may be combined, for example to allow a direct formation of a compound of formula IIa from a compound of formula $INT_1$. Steps ii) and/or iii) may also be performed under microwave irradiation, each optionally also in a pressurized vessel. Compounds of the formula $INT_1$ may alternatively be prepared under conditions and variants of the Pinner reaction known to a person skilled in the art, typically by treating a compound of the formula IV with a hydrohalide acid, preferably hydrochloric acid, in presence of alcoholic reagents such as methanol or ethanol, preferably in an inert solvent such as diethyl ether, tetrahydrofuran or dioxane, at temperatures between −40 and 50° C., preferably between −20 and 20° C. The described process to prepare compounds of the formula IIa from compounds of the formula IV may include isolation and purification of the intermediates $INT_1$ and/or $INT_2$ (which may be isolated as free bases or as salts (e.g. a hydrohalide salt, more specifically a hydrochloride or hydrobromide salt, or any other equivalent salt)), however this process is advantageously conducted as a one-pot preparation. In the particular situation where $R_8$ is methyl or ethyl, the amine reagent of formula V may be engaged in the above reaction as a gas, as a salt (such as a hydrohalide salt, preferably a hydrochloride or a hydrobromide salt, or any other equivalent salt), or as a solution in solvents such as methanol, ethanol, tetrahydrofuran or water.

Compounds of formula IIb, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, and in which R is $C_1$-$C_6$alkyl, Scheme 4 i) Carboxylic acid activation
ii) Treat with:

$H_2N$—$R_8$
V

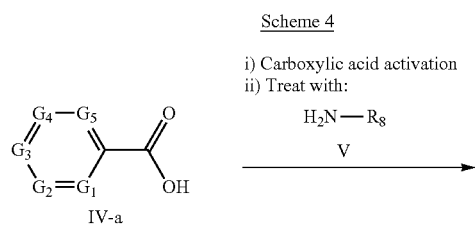

IV-a

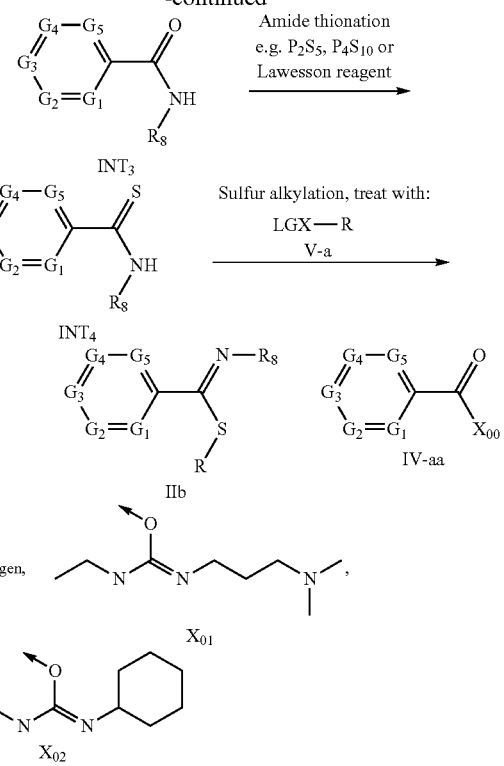

may be prepared by reacting a compound of formula $INT_4$, wherein $R_8$, $G_1$, $G_2$, $G_3$, $G_4$, and $G_5$ are as defined above, with an alkylation reagent of formula V-a, wherein R is $C_1$-$C_6$alkyl, and in which LGX is a leaving group, such as a halogen (especially bromine or iodine), or a leaving group $OSO_2R'$, wherein R' is $C_1$-$C_6$alkyl, $C_1$-$C_6$haloalkyl, or phenyl optionally substituted by nitro or $C_1$-$C_3$alkyl (especially a sulfonate such as mesylate, triflate or tosylate) or a sulfate (forming for example the alkylating agent V-a dimethylsulfate, in the particular situation where R' is methyl), preferably in the presence of a suitable base, such as sodium hydride or sodium, potassium or cesium carbonate, in an inert solvent such as tetrahydrofuran, dioxane, acetonitrile, N,N-dimethylformamide, N,N-dimethylacetamide, N-methyl-2-pyrrolidone or dimethyl sulfoxide. Another advantageous base/solvent combination for this transformation is also, for example, an alkoxide, preferably sodium methoxide NaOMe or sodium ethoxide NaOEt, in an alcoholic solvent, such as methanol or ethanol, at temperatures between 0-100° C., preferably around ambient temperature. The compounds of formula IIb may be isolated with any configuration (E or Z, or any mixture thereof) on the carbon-nitrogen double bond. Such a process may be carried out in analogy to, for example, M. H. Klingele et al, Eur. J. Org. Chem. 2004, 3422-3434.

Compounds of formula $INT_4$, wherein $R_8$, $G_1$, $G_2$, $G_3$, $G_4$, and $G_5$ are as defined above, may be prepared by reacting a compound of formula $INT_3$, wherein $R_8$, $G_1$, $G_2$, $G_3$, $G_4$, and $G_5$ are as defined above, with a thionation agent, such as phosphorus decasulfide $P_4S_{10}$ (also called phosphorus pentasulfide $P_2S_5$), or the Lawesson reagent (2,4-bis(4-methoxyphenyl)-1,3,2,4-dithiadiphosphetane-2,4-dithione), in inert solvents such as toluene, xylene, tetrahydrofuran, dioxane or pyridine, at temperatures between 0-200° C., preferably between 50 and 150° C., optionally under microwave irradiation. Such a process may be carried out in analogy to, for example, T. Ozturk et al., Chem. Rev. 2010, 110, 3419-3478.

Compounds of formula $INT_3$, wherein $R_8$, $G_1$, $G_2$, $G_3$, $G_4$, and $G_5$ are as defined above, may be prepared by
i) activation of a compound of formula IV-a, wherein $G_1$, $G_2$, $G_3$, $G_4$, and $G_5$ are as defined above, by methods known to those skilled in the art and described in, for example, Tetrahedron, 2005, 61 (46), 10827-10852, to form an activated species IV-aa, wherein $G_1$, $G_2$, $G_3$, $G_4$, and $G_5$ are as defined above and wherein $X_{00}$ is halogen, preferably chlorine. For example, compounds IV-aa where $X_{00}$ is halogen, preferably chlorine, are formed by treatment of IV-a with, for example, oxallyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THF at temperatures between 20 to 100° C., preferably 25° C. Alternatively, treatment of compounds of formula IV-a with, for example, 1-ethyl-3-(3-dimethylaminopropyl)carbodiimide EDC or dicyclohexyl carbodiimide DCC will generate an activated species IV-aa, wherein $X_{00}$ is $X_{01}$ or $X_{02}$ respectively, in an inert solvent, such as pyridine or tetrahydrofuran THF, optionally in the presence of a base, such as triethylamine, at temperatures between 50-180° C.; followed by
ii) treatment of the activated species IV-aa with an amine reagent of formula V $$R_8-NH_2 \quad (V),$$

or a salt thereof (such as a hydrohalide salt, preferably a hydrochloride or a hydrobromide salt, or any other equivalent salt), wherein $R_8$ is as defined above, optionally in the presence of a base, such as triethylamine or pyridine, in an inert solvents such as dichloromethane, tetrahydrofuran, dioxane or toluene, at temperatures between 0 and 50° C., to form the compounds of formula $INT_3$. Certain bases, such as pyridine and triethylamine, may be employed successfully as both base and solvent.

Compounds of formula IV and compounds of formula IV-a, wherein $G_1$, $G_2$, $G_3$, $G_4$, and $G_5$ are as defined above, are known compounds or can be prepared by known methods, described in the literature.

Compounds of the formula III, or a salt thereof, wherein $R_7$ is as defined above, Scheme 5

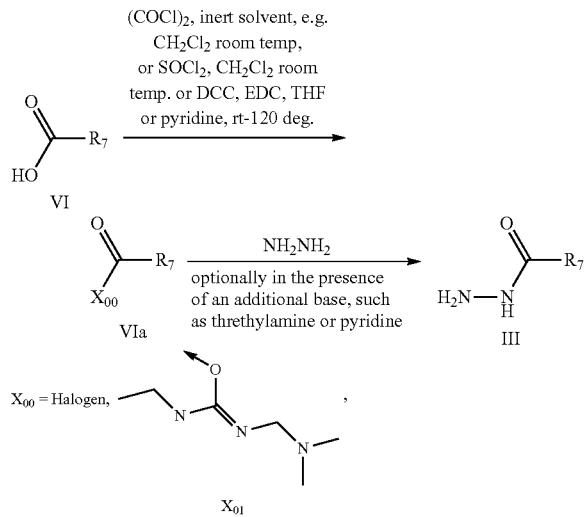

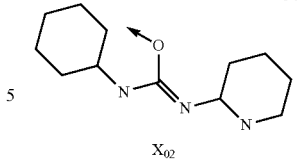

may be prepared by
i) activation of compound of formula VI, wherein $R_7$ is as defined above, by methods known to those skilled in the art and described in, for example, Tetrahedron, 2005, 61 (46), 10827-10852, to form an activated species Via, wherein $R_7$ is as defined above and wherein $X_{00}$ is halogen, preferably chlorine. For example, compounds Via where $X_{00}$ is halogen, preferably chlorine, are formed by treatment of VI with, for example, oxallyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THF at temperatures between 20 to 100° C., preferably 25° C. Alternatively, treatment of compounds of formula VI with, for example, 1-ethyl-3-(3-dimethylaminopropyl)carbodiimide EDC or dicyclohexyl carbodiimide DCC will generate an activated species Via, wherein $X_{00}$ is $X_{01}$ or $X_{02}$ respectively, in an inert solvent, such as pyridine or tetrahydrofuran THF, optionally in the presence of a base, such as triethylamine, at temperatures between 50-180° C.; followed by
ii) Treatment of the activated species Via with hydrazine $NH_2NH_2$ (or a salt thereof), possibly in form of a hydrate, preferably hydrazine monohydrate, optionally in the presence of a base, such as triethylamine or pyridine, in an inert solvents such as dichloromethane, tetrahydrofuran, dioxane or toluene, at temperatures between 0 and 50° C., to form the compounds of formula III.

Alternatively, compounds of the formula III, or a salt thereof, wherein $R_7$ is as defined above, may be prepared by the direct action of hydrazine (or a salt thereof), possibly in form of a hydrate, preferably hydrazine monohydrate, on an ester derivative VIb

(VIb)

of the compound of formula VI, wherein $R_7$ is as defined above and wherein $R_{00}$ is $C_1$-$C_4$alkyl, preferably methyl or ethyl, at temperatures between 20 and 150° C. This reaction is preferably performed in an alcoholic solvent, such as methanol or ethanol. Such a process description may be found, for example, in M. H. Klingele et al, Eur. J. Org. Chem. 2004, 3422-3434.

Compounds of formula VI and VIb, wherein $R_7$ is as defined above, are known compounds or can be prepared by known methods, described in the literature. In particular, ester compounds of formula VIb, wherein $R_7$ is as defined above and wherein $R_{00}$ is $C_1$-$C_4$alkyl, may be prepared from the corresponding carboxylic acid compounds of formula VI, wherein $R_7$ is as defined above, by reaction with an alcohol of formula $R_{00}OH$ (XII), wherein $R_{00}$ is $C_1$-$C_4$alkyl, optionally in the presence of an acid (such as sulfuric acid), or alternatively optionally in presence of an activating agent, such as for example oxalyl chloride (COCl)$_2$. Such esterification methods are well known to a person skilled in the art.

Compounds of formula I, wherein R$_7$, R$_8$, G$_1$, G$_2$, G$_3$, G$_4$, and G$_5$ are as defined in formula I and wherein X is S (sulfide), Scheme 6

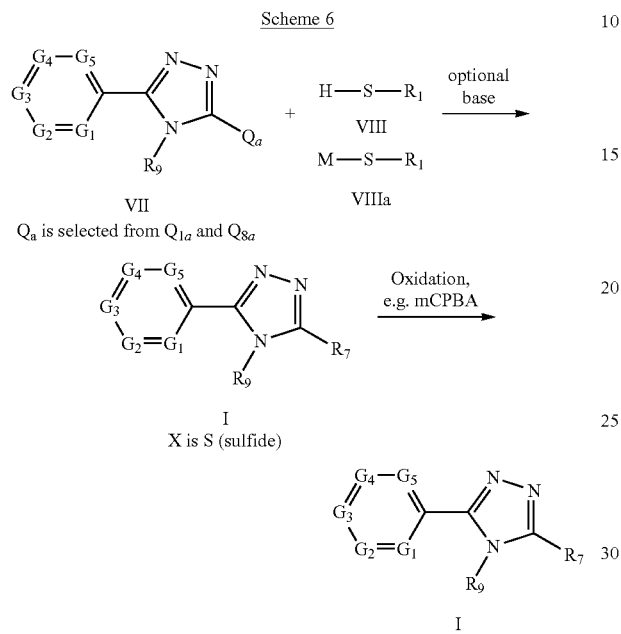

can also be prepared by reacting a compound of formula VII, wherein R$_8$, G$_1$, G$_2$, G$_3$, G$_4$, and G$_5$ are as described in formula I and wherein Q$_a$ is a radical selected from the group consisting of formula Q$_{1a}$ to Q$_{14a}$:

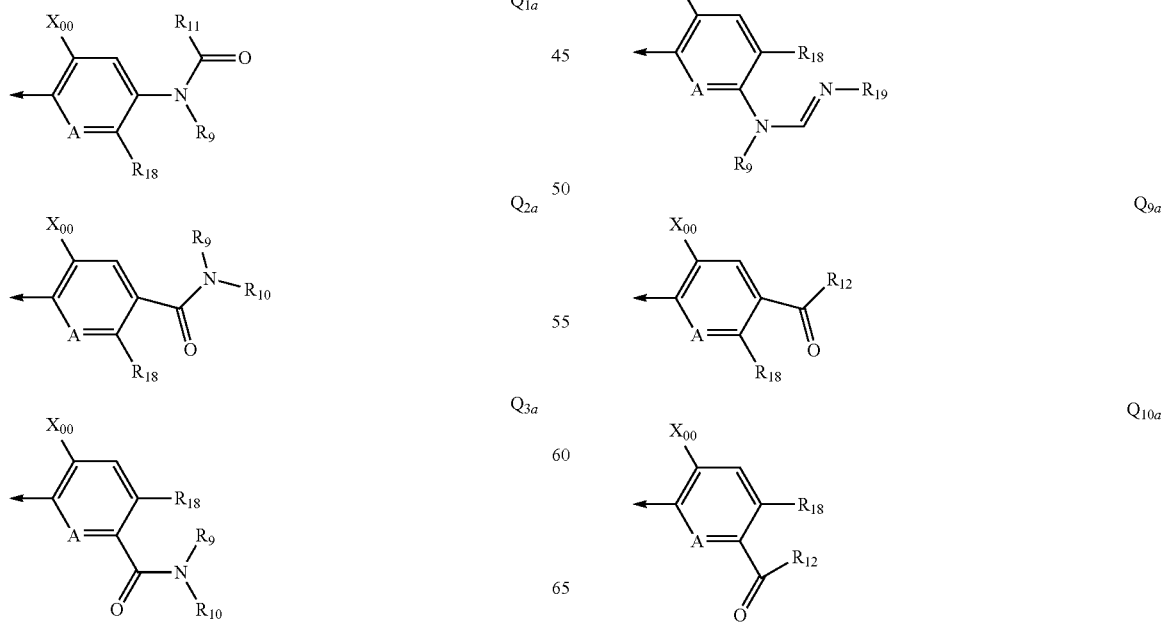

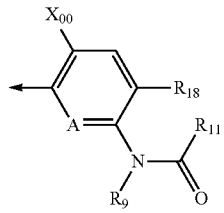

Q$_{4a}$

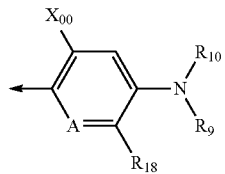

Q$_{5a}$

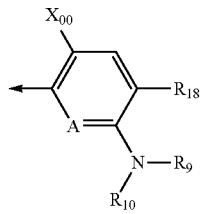

Q$_{6a}$

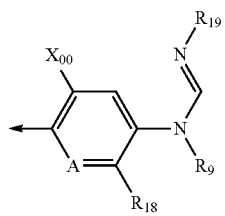

Q$_{7a}$

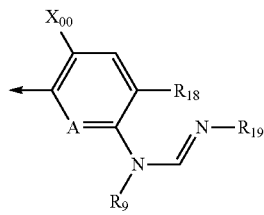

Q$_{8a}$

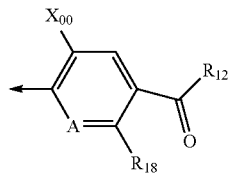

Q$_{9a}$

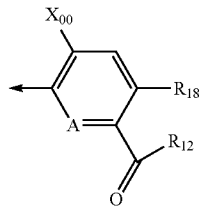

Q$_{10a}$

-continued

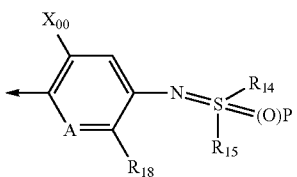
$Q_{11a}$

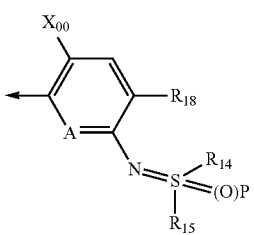
$Q_{12a}$

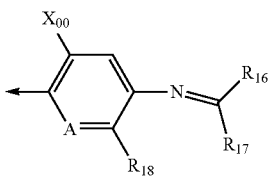
$Q_{13a}$

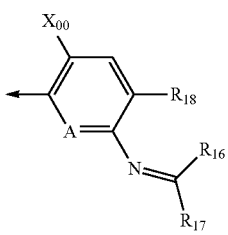
$Q_{14a}$ wherein A, $R_9$, $R_{10}$, $R_{11}$, $R_{12}$, $R_{14}$, $R_{15}$, $R_{16}$, $R_{17}$, $R_{18}$, $R_{19}$ are as defined in formula I, and wherein $X_{00}$ is a halogen (preferably fluorine, chlorine or bromine), with a compound of formula VIII

 $R_1$—SH        (VIII), or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula VIII include compounds of the formula VIIIa

 $R_1$—S-M        (VIIIa), wherein $R_1$ is as defined above and wherein M is, for example, sodium or potassium.

Compounds of formula VII, wherein $R_8$, $G_1$, $G_2$, $G_3$, $G_4$, and $G_5$ are as defined above, and wherein $Q_a$ is a radical selected from the group consisting of formula $Q_{1a}$ to $Q_{14}$a described above,

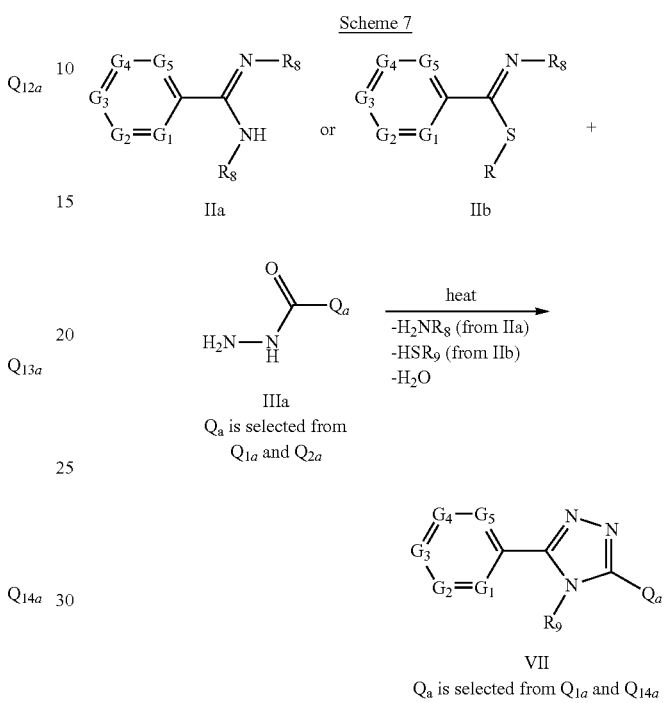

Scheme 7

IIa    IIb

IIIa
$Q_a$ is selected from $Q_{1a}$ and $Q_{2a}$ heat
$-H_2NR_8$ (from IIa)
$-HSR_9$ (from IIb)
$-H_2O$ VII
$Q_a$ is selected from $Q_{1a}$ and $Q_{14a}$ may be prepared by reacting an amidine compound of formula IIa, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above;

or alternatively, by reacting an alkyl carboximidothioate compound of formula IIb, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, and in which R is $C_1$-$C_6$alkyl;

with a hydrazide compound of formula IIIa, or a salt thereof, wherein $Q_a$ is is a radical selected from the group consisting of formula $Q_{1a}$ to $Q_{14a}$ described above, optionally in presence of a base such as alkali metal carbonates, for example sodium carbonate or potassium carbonate, in a solvent such as methanol, ethanol, isopropanol, acetonitrile, pyridine, acetic acid, N,N-dimethylformamide or N,N-dimethylacetamide, at temperatures between 0 and 200° C., preferably between 50 and 180° C., optionally under microwave irradiation. The compounds of formula IIa or IIb may be reacted with any configuration (E or Z, or any mixture thereof) on the carbon-nitrogen double bond.

Compounds of formula IIIa, or a salt thereof, wherein $Q_a$ is as defined above, may be prepared in analogy to processes described above in the context of the preparation of compounds of the formula III as described in scheme 8.

Shceme 8

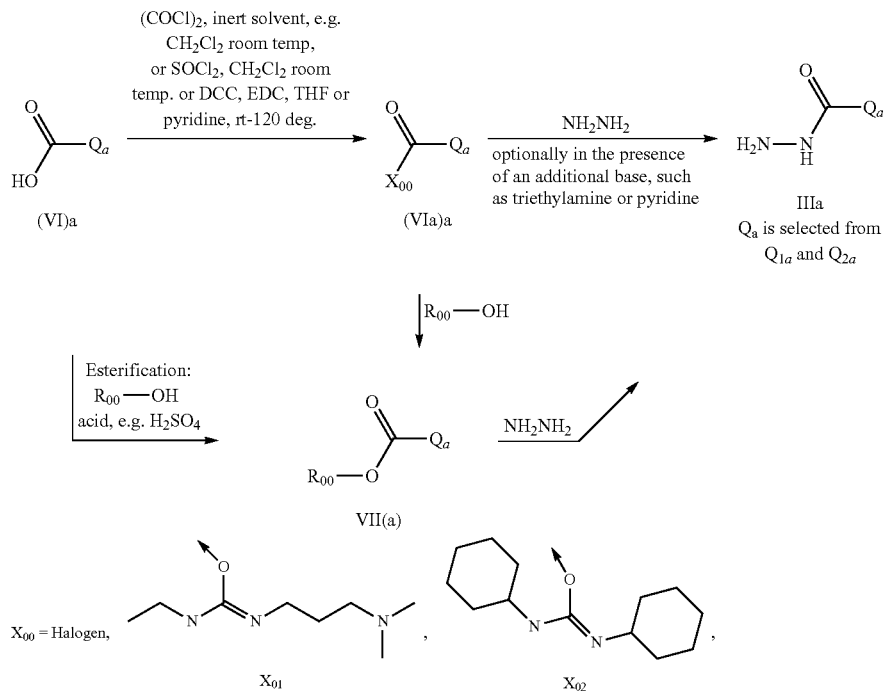

Compounds of formula VI(a) and VIb(a), wherein $Q_a$ and $R_{00}$ are as defined above, are known compounds or can be prepared by known methods, described in the literature.

Alternatively, Compounds of formula IX, wherein X, $R_8$, $G_1$, $G_2$, $G_3$, $G_4$, and $G_5$ are as defined above, and wherein $Q_b$ is a radical selected from the group consisting of formula $Q_{1b}$ to $Q_{4b}$ described above,

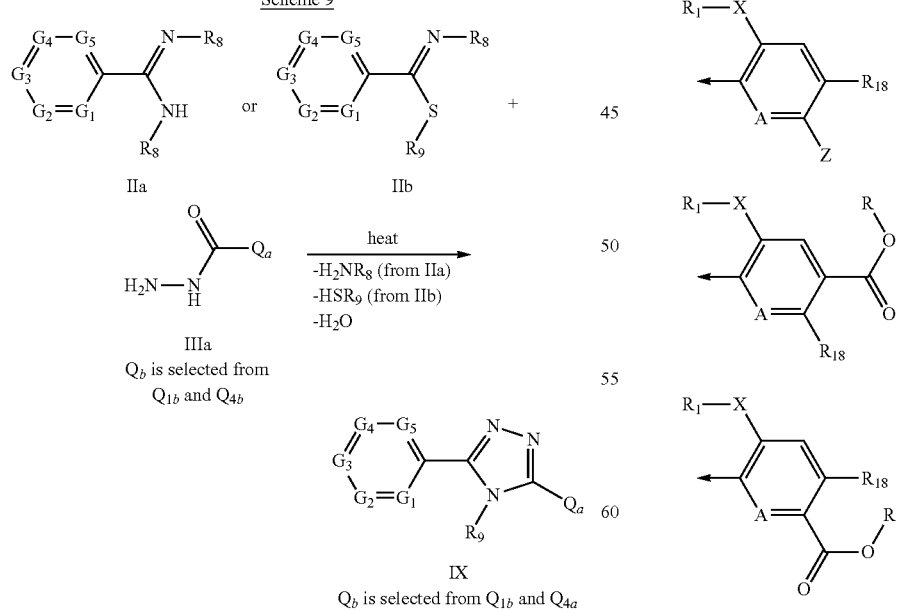

and wherein $Q_b$ is a radical selected from the group consisting of formula $Q_{1b}$ to $Q_{4b}$:

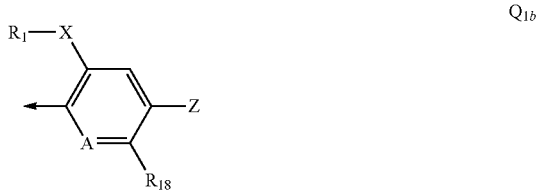

wherein Z is an leaving group such as a halogen, for example a bromide or a amine protected or not, wherein R is hydrogen or a $C_1$-$C_4$ alkyl group and wherein $R_1$ and $R_{18}$ are as defined in formula I above, may be prepared as described before for Qa analogues or $R_7$ analogues.

Compounds of formula I, wherein X, $R_8$, $G_1$, $G_2$, $G_3$, $G_4$, and $G_5$ are as defined in formula I above and $R_7$ is $Q_1$, $Q_2$, $Q_5$ and $Q_6$, can also be prepared by reacting a compound of formula IX, wherein $R_8$, $G_1$, $G_2$, $G_3$, $G_4$, and $G_5$ are as described in formula I and wherein $Q_b$ is a radical $Q_{1b}$ or $Q_{2b}$ by a Buchwald-Hartwig cross coupling, which involves for example, reacting compounds of formula IX, wherein Z is a leaving group, for example, chlorine, bromine or iodine, or an aryl- or alkylsulfonate such as trifluoromethanesulfonate with, for example, compounds of formula Xa or Xb. The reaction can be catalyzed by a palladium based catalyst, for example Palladium acetate, in presence of a base, like cesium carbonate or sodium tert-butoxide, in a solvent or a solvent mixture, like, for example toluene, preferably under inert atmosphere and in presence of chelatine phosphine such as BINAP or Xamtphos. The reaction temperature can preferentially range from ambient temperature to the boiling point of the reaction mixture. Such Buchwald-Hartwig cross coupling are well known to those skilled in the art, many variation are described in literature and have been reviewed, for example in Strategic Applications of Named Reactions in Organic Synthesis (Kurti, Laszlo; Czako, Barbara; Editors. Ed. ELSEVIER) 2005, p 70 and cited references; Modern Tools for the Synthesis of Complex Bioactive Molecules (Chapter 3: Metal-catalyzed C-heteroatom cross-coupling reactions) 2012, p. 77-109.

Alternatively, similar reactions can be carried out in the presence of a copper source such as copper(I) iodide (CuI) or copper(II) trifluoromethanesulfonate and a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-but oxide. The reaction can be carried out in a suitable solvent such as 1,4-dioxane, N,N-dimethylformamide, dimethyl sulfoxide or N-methylpyrolidinone at a temperature between 100 and 180 degrees centigrade for 15 to 60 minutes under microwave irradiation. See for example US 20140142081, Chemical Communications 2011, 47(31), 8976-8978; Advanced Synthesis & Catalysis 2010, 352(18), 3158-3162.

Alternatively, compounds of formula I, wherein $R_7$, X, $R_8$, $G_1$, $G_2$, $G_3$, $G_4$, and $G_5$ are as defined in formula I, can prepared by nucleophile substitution which involves for example, reaction of compounds of formula IX, wherein Z is a leaving group, for example, fluorine with compounds of formula Xa under basic condition such as potassium carbonate in a solvent such as DMF, see for example Bioorganic & Medicinal Chemistry Letters 2013, 23(6), 1720-1726; WO 2010137349. See scheme 10

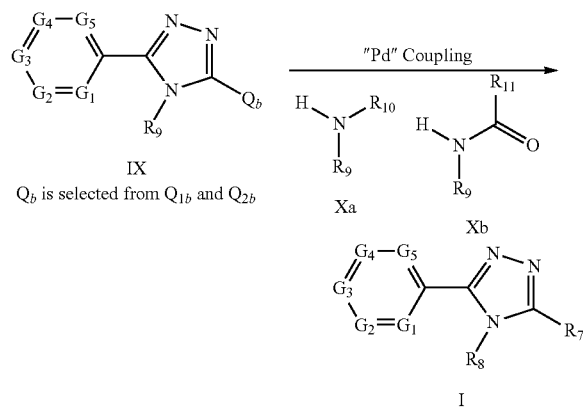

Alternatively, compounds of formula IXb wherein X, $R_1$, $R_8$, $R_{18}$, $G_1$, $G_2$, $G_3$, $G_4$, and $G_5$ are as defined in formula I above, can be prepared starting from compounds of formula IX wherein X, $R_1$, $R_8$, $R_{18}$, $G_1$, $G_2$, $G_3$, $G_4$, and $G_5$ are as defined in formula I above and wherein Z is a leaving group such as chloride or bromide, as shown in scheme 11 by substitution of a leaving group (LG) by a azide group coming, for example from sodium azide in a solvent such as N,N-Dimethylformamide or DMSO in presence or not of catalyst such as copper iodine in presence or a ligand such as proline or DMEDA, followed or not by reduction of the azide group in amine under classical reduction condition (see for example: Synthetic Organic Methodology: Comprehensive Organic Transformations. A Guide to Functional Group Preparations, Larock, R. C. 1989 p 409). These reactions can be performed in various organic or aqueous solvents compatible to these conditions, by temperatures from below 0° C. up to the boiling point of the solvent system. This succession of reaction to realize this transformation is well known to those skilled in the art and for example, similar reactions are described in: Medicinal Chemistry Research, 24(1), 171-181; 2015; Tetrahedron Letters, 53(23), 2922-2924; 2012. Alternatively, this reaction could be done in one step and the azide could be reduce in situ under copper catalyst conditions as described in, for example, Journal of Organic Chemistry (2010), 75(14), 4887-4890 and cited references therein. Alternatively, compounds of formula IXb wherein X, $R_1$, $R_8$, $R_{18}$, $G_1$, $G_2$, $G_3$, $G_4$, and $G_5$ are as defined in formula I above, can be prepared a coupling reaction (type Buchwald-Hartwig cross coupling as described for scheme 10) followed by hydrolysis or deprotection of the amino group. Such transformation is very well known by people skilled in the art and are analogues at the examples find, for example Tetrahedron Letters, 38(36), 6367-6370; 1997 or Journal of Organic Chemistry, 72(21), 8146-8148; 2007 and cited references. See scheme 11

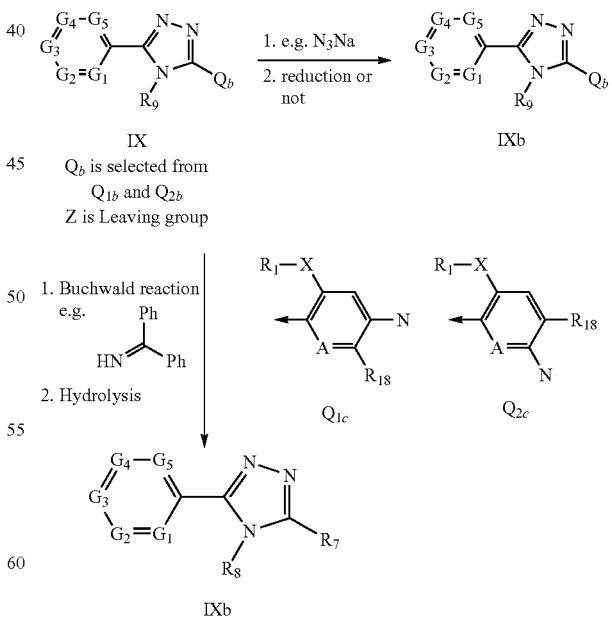

Compounds of formula I wherein X, $R_1$, A, $R_7$, $R_8$, $R_9$, $R_{10}$, $R_{11}$, $R_{18}$, $G_1$, $G_2$, $G_3$, $G_4$, and $G_5$ are as defined in formula I above and wherein $R_7$ is selected from $Q_5$ and $Q_6$, wherein $R_{10}$ is hydrogen, can be made by formation of the N—R$_9$ bond via reductive amination with an aldehyde RxCH(O) or alkylation with R$_9$-XLG$_2$. Reductive amination may be achieved by treatment of the compounds of formula IX with an aldehyde VII and a reducing agent such as sodium cyanoborohydride. Such reactions can be carried out under well-established methods and various conditions could be used, described for example in Synthetic Organic Methodology: Comprehensive Organic Transformations, a Guide to Functional Group Preparations, Larock, R. C. 1989 p 421. Alkylation may be achieved by treatment of the compounds of formula IX with R$_9$-XLG$_2$ wherein XLG$_2$ is chloro, bromo, iodo, mesylate, triflate in presence of a base such as potassium carbonate in a solvent such as dimethylsulfoxide, acetonitrile, tetrahydrofuran, dimethylformamide or toluene could give compounds of formula I wherein X, R$_1$, R$_7$, R$_8$, R$_{18}$, G$_1$, G$_2$, G$_3$, G$_4$, and G$_5$ are as defined in formula I above and wherein R$_7$ is selected from Q$_5$ and Q$_6$ wherein R$_{10}$ is hydrogen. Such reactions can be carried out under well-established methods, described for example, Organic Preparations and Procedures International, 36(4), 347-351; 2004; WO 2004074270 or Tetrahedron, 59(39), 7651-7659; 2003. Compounds of formula I wherein X, R$_7$, R$_8$, R$_{18}$, G$_1$, G$_2$, G$_3$, G$_4$, and G$_5$ are as defined in formula I above and wherein R$_7$ is selected from Q$_1$ and Q$_4$ can be made by reaction of compounds of formula I wherein X, R$_1$, R$_7$, R$_8$, R$_{18}$, G$_1$, G$_2$, G$_3$, G$_4$, and G$_5$ are as defined in formula I above and wherein R$_7$ is selected from Q$_5$ and Q$_6$ wherein R$_{10}$ is hydrogen with a compound of formula XIII wherein XLG$_1$ is OH, C$_1$-C$_6$alkoxy or Cl, F or Br. When XLG$_1$ is OH such reactions are usually carried out in the presence of a coupling reagent, such as dicyclohexyl-carbo-diimide ("DCC"), N-(3-Dimethylaminopropyl)-N'-ethylcarbodiimide hydrochloride ("EDC") or bis(2-oxo-3-oxazolidinyl) phosphonic chloride ("BOP-Cl"), in the presence of a base, and optionally in the presence of a nucleophilic catalyst, such as hydroxybenzo-triazole ("HOBT"). When XLG$_1$ is Cl, such reactions are usually carried out in the presence of a base, and optionally in the presence of a nucleophilic catalyst for example dimethylaminopyridine. Alternatively, it is possible to conduct the reaction in a biphasic system comprising an organic solvent, preferably ethyl acetate, and an aqueous solvent, preferably a solution of sodium hydrogen carbonate. When XLG$_1$ is C$_1$-C$_6$alkoxy it is possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are NN-dimethylacetamide, tetrahydrofuran, dioxane, 1,2-dimethoxyethane, ethyl acetate and toluene. The reaction is carried out at a temperature of from 0 degrees centigrade to 100 degrees centigrade, preferably from 15 degrees centigrade to 30 degrees centigrade, in particular at ambient temperature. Such reactions can be carried out under well-established methods and various conditions could be used, described for example in Synthetic Organic Methodology: Comprehensive Organic Transformations, a Guide to Functional Group Preparations, Larock, R. C. 1989 p 972. Alternatively, the sequence could be reversed and the acetylation could be done first and the alkylation or reductive amination could be done in second to give access to compounds of formula I wherein X, R$_1$, R$_7$, R$_8$, R$_{18}$, G$_1$, G$_2$, G$_3$, G$_4$, and G$_5$ are as defined in formula I above and wherein R$_7$ is selected from Q$_1$ and Q$_4$ wherein R$_9$ is hydrogen, then these compounds could be alkylated to give compounds of formula I wherein X, R$_1$, R$_7$, R$_8$, R$_{18}$, G$_1$, G$_2$, G$_3$, G$_4$, and G$_5$ are as defined in formula I above and wherein R$_7$ is selected from Q$_1$ and Q$_4$. For illustration, see scheme 12.

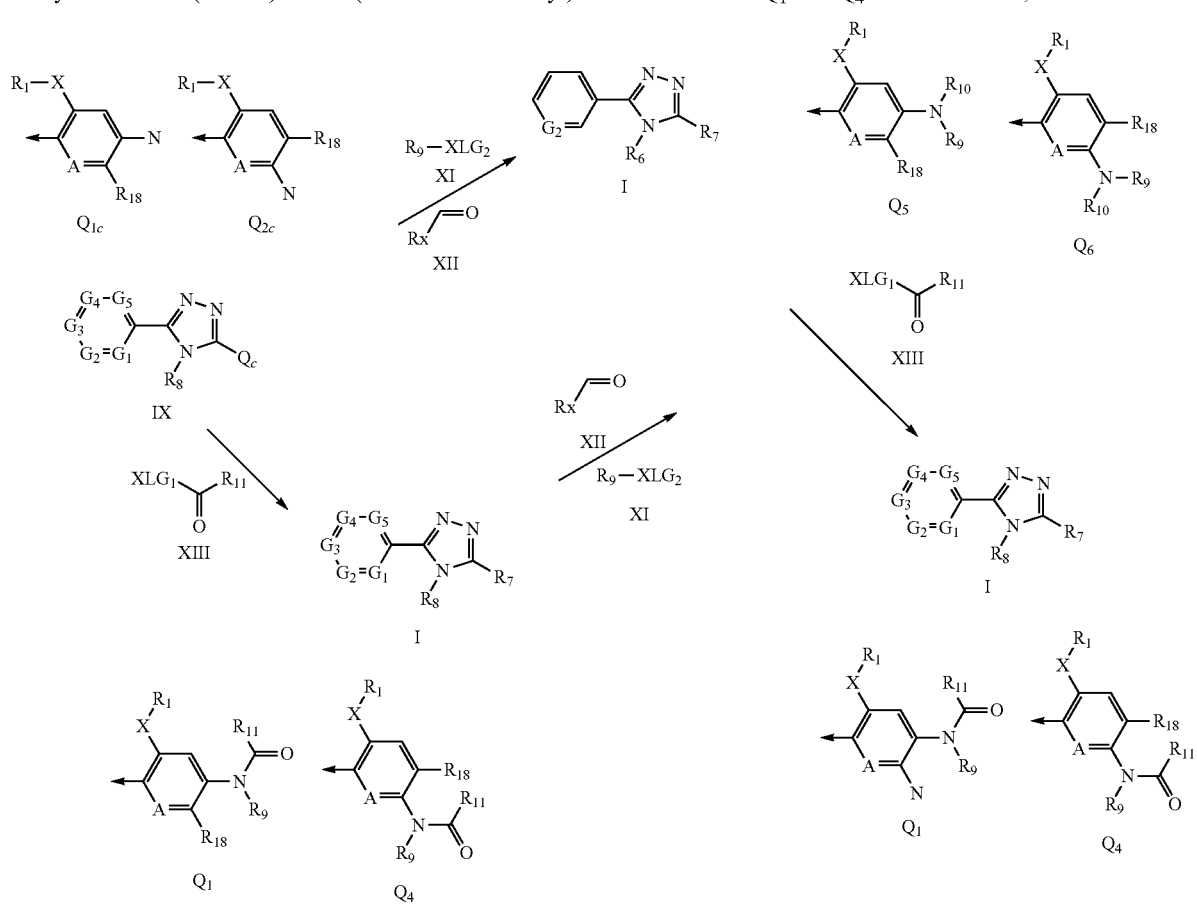

Compounds of formula I, wherein X, $R_1$, A, $R_7$, $R_8$, $R_9$, $R_{10}$, $R_{11}$, $R_{12}$, $R_{18}$, $G_1$, $G_2$, $G_3$, $G_4$, and $G_5$ are as defined in formula I above and wherein $R_7$ is selected from $Q_9$ and $Q_{10}$, can be made by various transformations from compounds of formula I, wherein X, $R_1$, A, $R_7$, $R_8$, $R_9$, $R_{10}$, $R_{11}$, $R_{12}$, $R_{18}$, $G_1$, $G_2$, $G_3$, $G_4$, and $G_5$ are as defined in formula I above, and wherein $R_7$ is selected from $Q_9$ and $Q_{10}$ wherein $R_{12}$ is OH. These transformations are well known for persons skilled in the art and are, for example esterification in presence of an alcohol under acidic conditions (see for example: Synthetic Organic Methodology: Comprehensive Organic Transformations. A Guide to Functional Group Preparations, Larock, R. C. 1989 p 966) or for example via an acid halides such as acyl chloride (see for example: Synthetic Organic Methodology: Comprehensive Organic Transformations. A Guide to Functional Group Preparations, Larock, R. C. 1989 p 963) and then reaction with a nucleophile such as, for example $C_1$-$C_6$alkoxyl substituted or not (see for example: Synthetic Organic Methodology: Comprehensive Organic Transformations. A Guide to Functional Group Preparations, Larock, R. C. 1989 p 978). Alternatively, Compounds of formula I wherein X, $R_1$, A, $R_7$, $R_8$, $R_9$, $R_{10}$, $R_{11}$, $R_{12}$, $R_{18}$, $G_1$, $G_2$, $G_3$, $G_4$, and $G_5$ are as defined in formula I above and wherein $R_7$ is selected from $Q_9$ and $Q_{10}$ wherein $R_{12}$ is an alkoxy group could be obtained directly from compounds of formula IXb wherein X, $R_1$, A, $R_8$, $G_1$, $G_2$, $G_3$, $G_4$, and $G_5$ are as defined in formula I above and wherein $Q_b$ is selected from $Q_{1b}$ and $Q_{2b}$ wherein Z is cyano by esterification in presence of an alcohol under acidic conditions (see for example: Synthetic Organic Methodology: Comprehensive Organic Transformations. A Guide to Functional Group Preparations, Larock, R. C. 1989 p 993).

Compounds of formula I wherein X, $R_1$, A, $R_7$, $R_8$, $R_9$, $R_{10}$, $R_{11}$, $R_{12}$, $R_{18}$, $G_1$, $G_2$, $G_3$, $G_4$, and $G_5$ are as defined in formula I above and wherein $R_7$ is selected from $Q_2$ and $Q_3$, can be made by various transformation from compound of formula I wherein X, $R_1$, A, $R_7$, $R_8$, $R_9$, $R_{10}$, $R_{11}$, $R_{12}$, $R_{18}$, $G_1$, $G_2$, $G_3$, $G_4$, and $G_5$ are as defined in formula I above and wherein $R_7$ is selected from $Q_9$ and $Q_{10}$ wherein $R_{12}$ is OH. These transformations are well known for people skilled in the art and are, for example by coupling reaction with an amine group (see for example: Synthetic Organic Methodology: Comprehensive Organic Transformations; A Guide to Functional Group Preparations, Larock, R. C. 1989 p 972-976) or for example via an acid halides such as acyl chloride (see for example: Synthetic Organic Methodology: Comprehensive Organic Transformations; Aa Guide to Functional Group Preparations, Larock, R. C. 1989 p. 963) and then reaction with a nucleophile such as, for example amino group substituted or not $HNR_9R_{10}$ (see for example: Synthetic Organic Methodology: Comprehensive Organic Transformations, A Guide to Functional Group Preparations, Larock, R. C. 1989 p 979). Alternatively, Compounds of formula I wherein X, $R_1$, A, $R_7$, $R_8$, $R_9$, $R_{10}$, $R_{11}$, $R_{12}$, $R_{18}$, $G_1$, $G_2$, $G_3$, $G_4$, and $G_5$ are as defined in formula I above and wherein $R_7$ is selected from $Q_2$ and $Q_3$ wherein $R_{12}$ is $NR_9R_{10}$ could be obtained directly from compounds of formula IXb wherein X, $R_1$, A, $R_8$, $G_1$, $G_2$, $G_3$, $G_4$, and $G_5$ are as defined in formula I above and wherein $Q_b$ is selected from $Q_{1b}$ and $Q_{2b}$ wherein Z is cyano by reaction in presence of an amine ($HNR_9R_{10}$) under various conditions (see for example: Synthetic Organic Methodology: Comprehensive Organic Transformations, A Guide to Functional Group Preparations, Larock, R. C. 1989 p 994).

Compounds of formula I wherein X, $R_1$, A, $R_7$, $R_8$, $R_9$, $R_{10}$, $R_{11}$, $R_{12}$, $R_{18}$, $G_1$, $G_2$, $G_3$, $G_4$, and $G_5$ are as defined in formula I above and wherein $R_7$ is selected from $Q_9$ and $Q_{10}$ wherein $R_{12}$ is OH can be made by 1) reaction of compounds of formula IX wherein X, $R_1$, A, $R_8$, $G_1$, $G_2$, $G_3$, $G_4$, and $G_5$ are as defined in formula I above and wherein $Q_b$ is selected from $Q_{1b}$ and $Q_{2b}$ wherein Z is a leaving group such as bromide with source of cyanide, such as zinc cyanide under or not metal catalysis such as palladium catalyst (see for example: Med. Chem. Commun., 2010, 1, 309-318). 2) by hydrolysis of the cyano group under acidic or basic conditions (see for example: Synthetic Organic Methodology: Comprehensive Organic Transformations: A Guide to Functional Group Preparations, Larock, R. C. 1989 p 993).

Alternatively, Compounds of formula I wherein X, $R_1$, A, $R_7$, $R_8$, $R_9$, $R_{10}$, $R_{11}$, $R_{12}$, $R_{18}$, $G_1$, $G_2$, $G_3$, $G_4$, and $G_5$ are as defined in formula I above and wherein $R_7$ is selected from $Q_9$ and $Q_{10}$ wherein $R_{12}$ is OH can be made by reaction of compounds of formula I wherein X, $R_1$, A, $R_7$, $R_8$, $R_9$, $R_{10}$, $R_{11}$, $R_{12}$, $R_{18}$, $G_1$, $G_2$, $G_3$, $G_4$, and $G_5$ are as defined in formula I above and wherein $R_7$ is selected from $Q_9$ and $Q_{10}$ wherein $R_{12}$ is $C_1$-$C_6$ alkoxy under acidic or basic conditions such as, for example sodium hydroxide or lithium hydroxide in a mixture of solvent such as water and tetrahydrofuranone. Such are well known for people skilled in the art and are, for example exemplified in Synthetic Organic Methodology: Comprehensive Organic Transformations. A Guide to Functional Group Preparations, Larock, R. C. 1989 p 981.

Alternatively, compounds of formula I wherein X, $R_1$, A, $R_7$, $R_8$, $R_9$, $R_{10}$, $R_{11}$, $R_{12}$, $R_{18}$, $G_1$, $G_2$, $G_3$, $G_4$, and $G_5$ are as defined in formula I above and wherein $R_7$ is selected from $Q_2$ and $Q_3$ can be made from compounds of formula I wherein X, $R_1$, A, $R_7$, $R_8$, $R_9$, $R_{10}$, $R_{11}$, $R_{12}$, $R_{18}$, $G_1$, $G_2$, $G_3$, $G_4$, and $G_5$ are as defined in formula I above and wherein $R_7$ is selected from $Q_9$ and $Q_{10}$ wherein $R_{12}$ is $C_1$-$C_6$ alkoxy by reaction with $HNR_9R_{10}$ under various conditions as described in Synthetic Organic Methodology: Comprehensive Organic Transformations: A Guide to Functional Group Preparations, Larock, R. C. 1989 p 987. See scheme 13.

Scheme 13

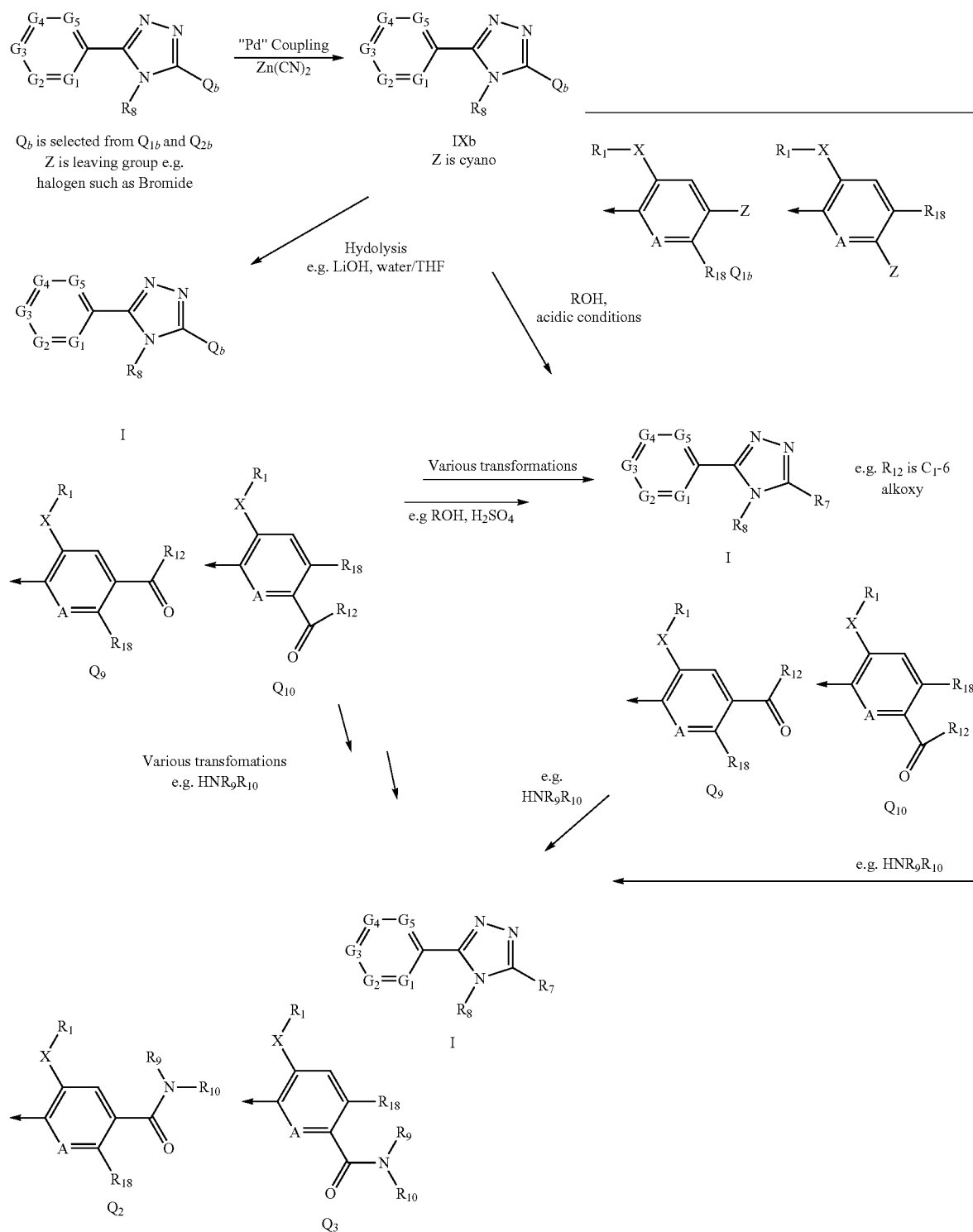

Compounds of formula I, wherein X, $R_1$, A, $R_7$, $R_8$, $R_{12}$, $R_{18}$, $G_1$, $G_2$, $G_3$, $G_4$, and $G_5$ are as defined in formula I above and wherein $R_7$ is selected from $Q_9$ and $Q_{10}$ can be made from compounds of formula IXd wherein X, $R_1$, A, $R_8$, $R_{18}$, $G_1$, $G_2$, $G_3$, $G_4$, and $G_5$ are as defined in formula I above and wherein Qb' is selected from $Q_{1b}$' and $Q_{2b}$' wherein $Z_1$ is a group of formula XIV, by oxidation, for example with sodium periodate in solvent such as water. This oxidative scission of Olefins to carbonyl derivatives, either through their ozonides or diols are well known by people skilled in the art and are used widely in organic synthesis, see for example: Synthetic Organic Methodology: Comprehensive Organic Transformations. A Guide to Functional Group Preparations, Larock, R. C. 1989 p 595; Science of Synthesis 2007, p 17-24. This transformation could be made in two steps, via the same type of diol intermediate by 1) transformation of compounds of formula IXd wherein X, $R_1$, A, $R_8$, $R_{18}$, $G_1$, $G_2$, $G_3$, $G_4$, and $G_5$ are as defined in formula I above and wherein Qb' is selected from $Q_{1b}$' and $Q_{2b}$' wherein $Z_1$ is a group of formula XIV to compounds of formula IXd wherein X, $R_1$, A, $R_8$, $R_{18}$, $G_1$, $G_2$, $G_3$, $G_4$, and $G_5$ are as defined in formula I above and wherein Qb' is selected from $Q_{1b}$' and $Q_{2b}$' wherein $Z_1$ is diol analogues XIVa followed by 2) oxidative scission of diols to Aldehydes or ketone. For step 1, see, for example: Curr. Org. Chem., 2004, 8, 1159; Chem. Rev., 1980, 80, 187; Chem. Rev., 1994, 94, 2483. For step 2, see, for example: Organic Letters, 12(7), 1552-1555; 2010; Synlett, (5), 739-742; 2009; Chemistry Letters, (12), 1951-2; 1982; Science of Synthesis 2007, p 17-24; Synthesis, (1), 64-5; 1989 and cited references. If Rc is $C_1$-$C_4$ Alkoxy, hydrolysis of the vinylester function will give compounds of formula I wherein X, $R_1$, A, $R_7$, $R_8$, $R_{12}$, $R_{18}$, $G_1$, $G_2$, $G_3$, $G_4$, and $G_5$ are as defined in formula I above and wherein $R_7$ is selected from $Q_9$ and $Q_{10}$. This transformation is well known in literature and could be exemplified by: Journal of Organic Chemistry, 55(10), 3114-8; 1990.

Compounds of formula IXd, wherein X, $R_1$, A, $R_8$, $R_{18}$, $G_1$, $G_2$, $G_3$, $G_4$, and $G_5$ are as defined in formula I above and wherein Qb' is selected from $Q_{1b}$' and $Q_{2b}$' wherein $Z_1$ is a group of formula XIV can be made from compounds of formula IX wherein X, $R_1$, A, $R_8$, $R_{18}$, $G_1$, $G_2$, $G_3$, $G_4$, and $G_5$ are as defined in formula I above and wherein Qb is selected from $Q_{1b}$ and $Q_{2b}$ wherein Z is leaving group, for example, chlorine, bromine or iodine (preferably bromine), or an aryl- or alkylsulfonate such as trifluoromethanesulfonate, with bispinacol diborane (Bpin)$_2$ under palladium catalysis and a $Yb_1$—$Z_1$ derivative wherein $Y_{b2}$ can be a boron-derived functional group, as for example B(OH)$_2$ or B(OR$_{b2}$)$_2$ wherein R$_{b2}$ can be a $C_1$-$C_6$alkyl group or the two groups OR$_{b2}$ can form together with the boron atom a five- or six-membered ring, as for example a pinacol boronic ester. The reaction can be catalyzed by a palladium based catalyst, for example tetrakis(triphenylphosphine)-palladium(0), bis(triphenylphosphine) palladium(II) dichloride or (1,1'bis(diphenylphosphino)-ferrocene)dichloropalladium-dichloromethane (1:1 complex), in presence of a base, like sodium carbonate or cesium fluoride, in a solvent (such as 1,2-dimethoxyethane, tetrahydrofuran or dioxane) or a solvent mixture, like, for example a mixture of 1,2-dimethoxyethane and water, or of dioxane and water, preferably under inert atmosphere. The reaction temperature can preferentially range from ambient temperature to the boiling point of the reaction mixture, or alternatively heating may be performed under microwave irradiation. This reaction is known as Suzuki cross-coupling. Such Suzuki reactions are well known to those skilled in the art and have been reviewed, for example J. Orgmet. Chem. 576, 1999, 147-168 or Kurti, Laszlo; Czako, Barbara; (Editors) Strategic Applications of Named Reactions in Organic Synthesis (2005) p 448.

Alternatively, compounds of formula IXd, wherein X, $R_1$, A, $R_8$, $R_{18}$, $G_1$, $G_2$, $G_3$, $G_4$, and $G_5$ are as defined in formula I above and wherein Qb' is selected from $Q_{1b}$' and $Q_{2b}$' wherein $Z_1$ is a group of formula XIV can be prepared by a Stille reaction of compounds of formula $Yb_2$—$Z_1$ derivative wherein $Y_{b2}$ is a trialkyl tin derivative, preferably tri-n-butyl tin, with compounds of formula IX wherein X, $R_1$, A, $R_8$, $R_{18}$, $G_1$, $G_2$, $G_3$, $G_4$, and $G_5$ are as defined in formula I above and wherein Qb is selected from $Q_{1b}$ and $Q_{2b}$ wherein Z is leaving group, for example, chlorine, bromine or iodine (preferably bromine), or an aryl- or alkylsulfonate such as trifluoromethanesulfonate. Such Stille reactions are usually carried out in the presence of a palladium catalyst, for example tetrakis(triphenylphosphine)palladium(0), or (1,1'bis(diphenylphosphino)-ferrocene)dichloropalladium-dichloromethane (1:1 complex), in an inert solvent such as DMF, acetonitrile, or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example J. Org. Chem., 2005, 70, 8601-8604, J. Org. Chem., 2009, 74, 5599-5602, and Angew. Chem. Int. Ed., 2004, 43, 1132-1136. Other alternative are possible such as Heck coupling (see for example: Proceedings (Electrochemical Society) 2006, p 2004-24 or Kurti, Laszlo; Czako, Barbara; (Editors) Strategic Applications of Named Reactions in Organic Synthesis (2005) p 196) or Negishi cross coupling (see for example: or Kurti, Laszlo; Czako, Barbara; (Editors) Strategic Applications of Named Reactions in Organic Synthesis (2005) p 310).

Scheme 14

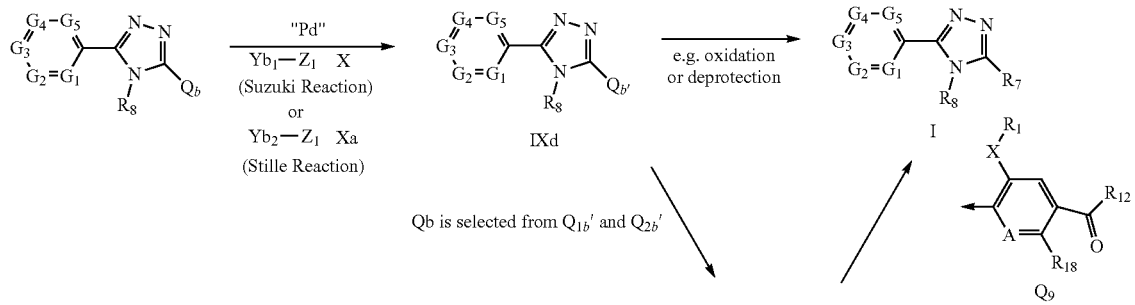

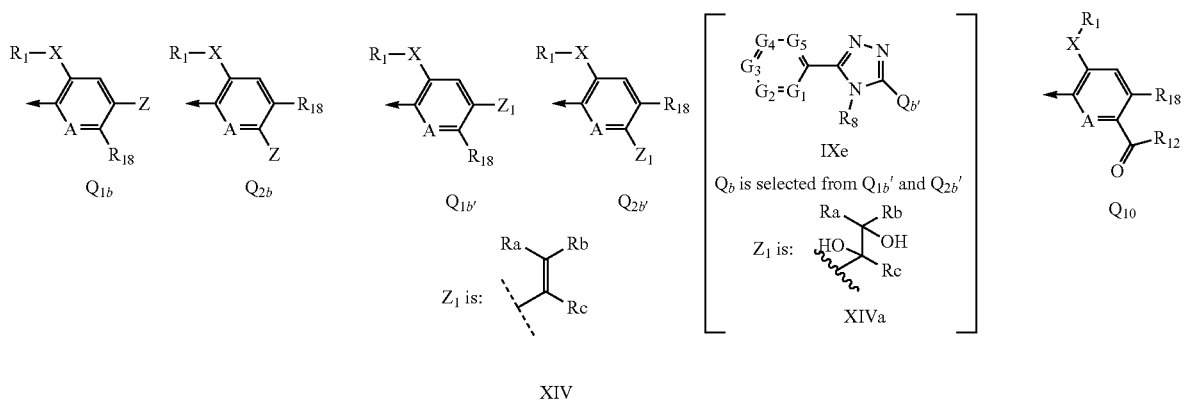

Compounds of formula I wherein X, $R_1$, A, $R_8$, $R_{18}$, $G_1$, $G_2$, $G_3$, $G_4$, and $G_5$ are as defined in formula I above and wherein $R_7$ is selected from $Q_{13}$ and $Q_{14}$, can prepared (as shown in scheme 15) by reaction of compounds of formula IXb wherein X, $R_1$, A, $R_8$, $R_{18}$, $G_1$, $G_2$, $G_3$, $G_4$, and $G_5$ are as defined in formula I and where in $Q_c$ is selected from $Q_1$ and $Q_{2c}$, with a compound of formula XV wherein $R_{16}$ and $R_{17}$ are as defined in formula I. Generally, these reactions are possible using a suitable dehydrating agent such as $TiCl_4$ or method such as distillation azeotropic under heating via refluxing the solvent or microwaves. Such reactions can be carried out under well-established methods, described for example, March's Advanced Organic Chemistry: Reactions, Mechanisms, and Structure, 5th Edition; Smith, Michael B.; March, Jerry p 1185; Tetrahedron: Asymmetry 2008, 19(1), 93-96;

Scheme 15

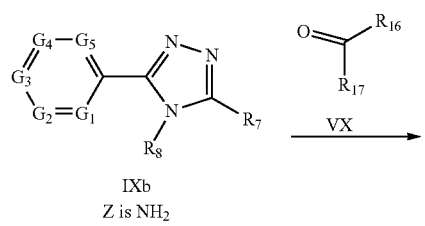

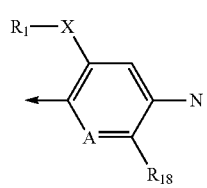

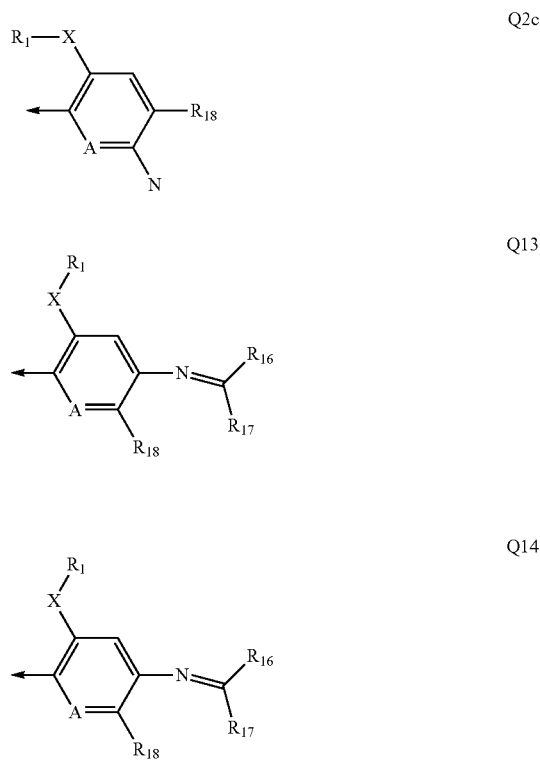

The subgroup of compounds of the formula I wherein G is —N(=$SR_{14}R_{15}$) defined as the sulfilimine I, wherein X, $R_1$, $R_8$, $R_{14}$, $R_{15}$, $R_{18}$, A, $G_1$, $G_2$, $G_3$, $G_4$, and $G_5$ are as defined in formula I, may be prepared by reacting compounds of the compounds of formula IXb wherein X, $R_1$, A, $R_8$, $R_{18}$, $G_1$, $G_2$, $G_3$, $G_4$, and $G_5$ are as defined in formula I and where in $Q_c$ is selected from $Q_1$ and $Q_{2c}$, under imination reaction conditions (step A, Scheme 16). The particular subgroup of compounds of the formula I wherein X is —N=S(O) $R_{14}R_{15}$ defined as the sulfoximine I, may be obtained by oxidation of the sulfilimine compounds of the formula Ib, as defined above (step B). See scheme 16

Scheme 16

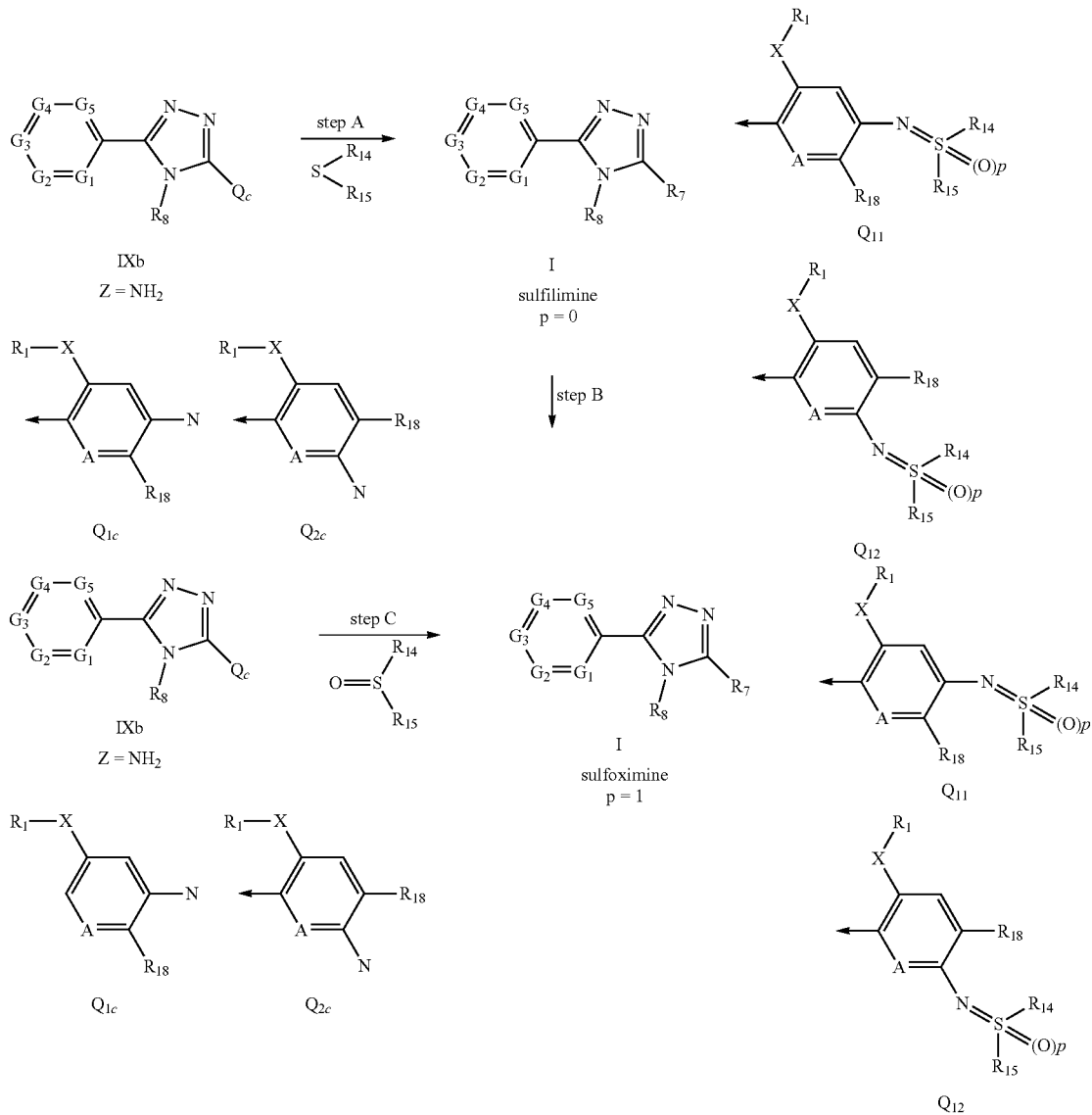

Typical preparation methods and reaction conditions to access the sulfilimines I (step A) or the sulfilimines I (step C), involve $SR_{14}R_{15}$ or $(O)SR_{14}R_{15}$ and an oxidant, for example, PhI(OAc)$_2$ as described in G. Y. Cho, C. Bolm, Tetrahedron Lett. 2005, 46, 8007-8008; or N-bromosuccinimide (NBS) and a base such as sodium or potassium ter-butoxide as described in C. Bolm et al., Synthesis 2010, No 17, 2922-2925. Oxidants such as N-iodosuccinimide (NIS) or iodine may be also used alternatively as described, for example, in O. G. Mancheno, C. Bolm, Org. Lett. 2007, 9, 3809-3811. An example of hypochlorite salts being used as oxidant, such as sodium hypochlorite NaOCl, was described in WO 2008/106006.

Typical preparation methods and reaction conditions to access the sulfoximines I (step B) from compounds of formula I (sulfilimines I), wherein X, $R_1$, A, $R_8$, $R_{14}$, $R_{15}$, $R_{18}$, $G_1$, $G_2$, $G_3$, $G_4$, and $G_5$ are clasical oxidation reagents such as KMnO$_4$, mCPBA, NaIO$_4$/RuO$_2$, H$_2$O$_2$, oxone. Such reactions can be carried out under well-established methods, described for example, in Journal of Organic Chemistry 1979, p 2510; Monatshefte fuer Chemie 1985, 116(10), 1153-64.

Alternatively Sulfoximine I wherein $R_7$ is Q11 or Q12 may be prepared by reacting compounds of the compounds of formula HN=S($R_{14}R_{15}$)=O with compounds of formula IXb wherein Z is a leaving group such as Bromide via a palladium coupling. See for example: Tetrahedron Letters, 39(32), 5731-5734; 1998, Journal of Organic Chemistry, 65(1), 169-175; 2000 or Tetrahedron, 70(37), 6613-6622; 2014.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo [5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 10 below can be prepared according to the methods described above. The examples which follow are intended to illustrate the invention and show preferred compounds of formula I.

Table 1:

This table discloses the 10 compounds 1.001 to 1.010 of the formula I-1a:

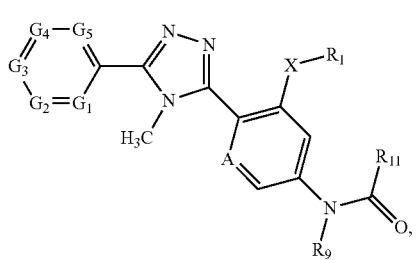 (I-1a)

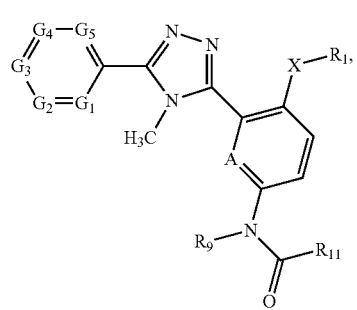 (I-2a)

wherein X is S, and A, $R_1$, $R_{11}$, $R_9$, $G_1$, $G_2$, $G_3$, $G_4$ and $G_5$ are as defined below:

wherein X is S, and A, $R_1$, $R_{11}$, $R_9$, $G_1$, $G_2$, $G_3$, $G_4$ and $G_5$ are as defined below:

TABLE 1

| Comp. No | A | $R_9$ | $R_{11}$ | $R_1$ | $G_1$ | $G_2$ | $G_3$ | $G_4$ | $G_5$ |
|---|---|---|---|---|---|---|---|---|---|
| 1.001 | CH | H | $C_3H_5$ | —$CH_2CH_3$ | N | CH | CH | $C(CF_3)$ | CH |
| 1.002 | CH | $CH_3$ | $C_3H_5$ | —$CH_2CH_3$ | N | CH | CH | $C(CF_3)$ | CH |
| 1.003 | CH | $SO_2CH_3$ | $C_3H_5$ | —$CH_2CH_3$ | N | CH | CH | $C(CF_3)$ | CH |
| 1.004 | CH | $SO_2N(CH_3)_2$ | $C_3H_5$ | —$CH_2CH_3$ | N | CH | CH | $C(CF_3)$ | CH |
| 1.005 | CH | H | $CH_3$ | —$CH_2CH_3$ | N | CH | CH | $C(CF_3)$ | CH |
| 1.006 | N | H | $C_3H_5$ | —$CH_2CH_3$ | N | CH | CH | $C(CF_3)$ | CH |
| 1.007 | N | $CH_3$ | $C_3H_5$ | —$CH_2CH_3$ | N | CH | CH | $C(CF_3)$ | CH |
| 1.008 | N | $SO_2CH_3$ | $C_3H_5$ | —$CH_2CH_3$ | N | CH | CH | $C(CF_3)$ | CH |
| 1.009 | N | $SO_2N(CH_3)_2$ | $C_3H_5$ | —$CH_2CH_3$ | N | CH | CH | $C(CF_3)$ | CH |
| 1.010 | N | H | $CH_3$ | —$CH_2CH_3$ | N | CH | CH | $C(CF_3)$ | CH | and the N-oxides of the compounds of Table 1. $C_3H_5$ is cyclopropyl.

Table 2:

This table discloses the 10 compounds 2.001 to 2.010 of the formula I-1a, wherein X is SO, and A, $R_1$, $R_{11}$, $R_9$, $G_1$, $G_2$, $G_3$, $G_4$ and $G_5$ are as defined in Table 1.

TABLE 4

| Comp. No | A | $R_9$ | $R_{11}$ | $R_1$ | $G_1$ | $G_2$ | $G_3$ | $G_4$ | $G_5$ |
|---|---|---|---|---|---|---|---|---|---|
| 4.001 | CH | H | $C_3H_5$ | —$CH_2CH_3$ | N | CH | CH | $C(CF_3)$ | CH |
| 4.002 | CH | $CH_3$ | $C_3H_5$ | —$CH_2CH_3$ | N | CH | CH | $C(CF_3)$ | CH |
| 4.003 | CH | $SO_2CH_3$ | $C_3H_5$ | —$CH_2CH_3$ | N | CH | CH | $C(CF_3)$ | CH |
| 4.004 | CH | $SO_2N(CH_3)_2$ | $C_3H_5$ | —$CH_2CH_3$ | N | CH | CH | $C(CF_3)$ | CH |
| 4.005 | CH | H | $CH_3$ | —$CH_2CH_3$ | N | CH | CH | $C(CF_3)$ | CH |
| 4.006 | N | H | $C_3H_5$ | —$CH_2CH_3$ | N | CH | CH | $C(CF_3)$ | CH |
| 4.007 | N | $CH_3$ | $C_3H_5$ | —$CH_2CH_3$ | N | CH | CH | $C(CF_3)$ | CH |
| 4.008 | N | $SO_2CH_3$ | $C_3H_5$ | —$CH_2CH_3$ | N | CH | CH | $C(CF_3)$ | CH |
| 4.009 | N | $SO_2N(CH_3)_2$ | $C_3H_5$ | —$CH_2CH_3$ | N | CH | CH | $C(CF_3)$ | CH |
| 4.010 | N | H | $CH_3$ | —$CH_2CH_3$ | N | CH | CH | $C(CF_3)$ | CH | and the N-oxides of the compounds of Table 4. $C_3H_5$ is cyclopropyl.

Table 3:

This table discloses the 10 compounds 3.001 to 3.010 of the formula I-1a, wherein X is $SO_2$, and A, $R_1$, $R_{11}$, $R_9$, $G_1$, $G_2$, $G_3$, $G_4$ and $G_5$ are as defined in Table 1.

Table 4:

This table discloses the 10 compounds 4.001 to 4.010 of the formula I-2a:

Table 5:

This table discloses the 10 compounds 5.001 to 5.010 of the formula I-2a, wherein X is SO, and A, $R_1$, $R_{11}$, $R_9$, $G_1$, $G_2$, $G_3$, $G_4$ and $G_5$ are as defined in Table 4.

Table 6:

This table discloses the 10 compounds 6.001 to 6.019 of the formula I-2a, wherein X is $SO_2$, and A, $R_1$, $R_{11}$, $R_9$, $G_1$, $G_2$, $G_3$, $G_4$ and $G_5$ are as defined in Table 4.

Table 7:

This table discloses the 10 compounds 7.001 to 7.012 of the formula I-3a:

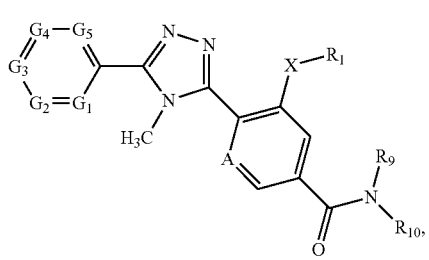
(I-3a)

wherein X is S, and A, $R_1$, $R_{10}$, $R_9$, $G_1$, $G_2$, $G_3$, $G_4$ and $G_5$ are as defined below:

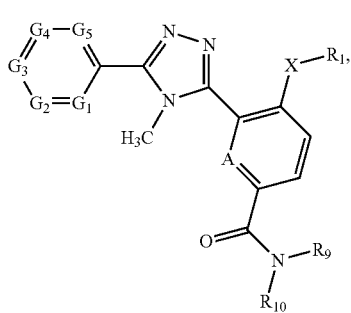
(I-4a)

wherein X is S, and A, $R_1$, $R_{10}$, $R_9$, $G_1$, $G_2$, $G_3$, $G_4$ and $G_5$ are as defined below:

TABLE 7

| Comp. No | A | $R_9$ | $R_{10}$ | $R_1$ | $G_1$ | $G_2$ | $G_3$ | $G_4$ | $G_5$ |
|---|---|---|---|---|---|---|---|---|---|
| 7.001 | CH | H | $C_3H_5$ | —$CH_2CH_3$ | N | CH | CH | $C(CF_3)$ | CH |
| 7.002 | CH | $CH_3$ | $C_3H_5$ | —$CH_2CH_3$ | N | CH | CH | $C(CF_3)$ | CH |
| 7.003 | CH | $SO_2CH_3$ | $C_3H_5$ | —$CH_2CH_3$ | N | CH | CH | $C(CF_3)$ | CH |
| 7.004 | CH | H | $CH_3$ | —$CH_2CH_3$ | N | CH | CH | $C(CF_3)$ | CH |
| 7.005 | CH | $CH_3$ | $CH_3$ | —$CH_2CH_3$ | N | CH | CH | $C(CF_3)$ | CH |
| 7.006 | CH | $SO_2CH_3$ | $CH_3$ | —$CH_2CH_3$ | N | CH | CH | $C(CF_3)$ | CH |
| 7.007 | N | H | $C_3H_5$ | —$CH_2CH_3$ | N | CH | CH | $C(CF_3)$ | CH |
| 7.008 | N | $CH_3$ | $C_3H_5$ | —$CH_2CH_3$ | N | CH | CH | $C(CF_3)$ | CH |
| 7.009 | N | $SO_2CH_3$ | $C_3H_5$ | —$CH_2CH_3$ | N | CH | CH | $C(CF_3)$ | CH |
| 7.010 | N | H | $CH_3$ | —$CH_2CH_3$ | N | CH | CH | $C(CF_3)$ | CH |
| 7.011 | N | $CH_3$ | $CH_3$ | —$CH_2CH_3$ | N | CH | CH | $C(CF_3)$ | CH |
| 7.012 | N | $SO_2CH_3$ | $CH_3$ | —$CH_2CH_3$ | N | CH | CH | $C(CF_3)$ | CH | and the N-oxides of the compounds of Table 7. $C_3H_5$ is cyclopropyl.

Table 8:

This table discloses the 12 compounds 8.001 to 8.012 of the formula I-3a, wherein X is SO, and A, $R_1$, $R_{10}$, $R_9$, $G_1$, $G_2$, $G_3$, $G_4$ and $G_5$ are as defined in Table 7.

Table 9:

This table discloses the 12 compounds 9.001 to 9.012 of the formula I-3a, wherein X is $SO_2$, and A, $R_1$, $R_{10}$, $R_9$, $G_1$, $G_2$, $G_3$, $G_4$ and $G_5$ are as defined in Table 7.

Table 10:

This table discloses the 12 compounds 10.001 to 10.012 of the formula I-4a:

TABLE 10

| Comp. No | A | $R_9$ | $R_{10}$ | $R_1$ | $G_1$ | $G_2$ | $G_3$ | $G_4$ | $G_5$ |
|---|---|---|---|---|---|---|---|---|---|
| 10.001 | CH | H | $C_3H_5$ | —$CH_2CH_3$ | N | CH | CH | $C(CF_3)$ | CH |
| 10.002 | CH | $CH_3$ | $C_3H_5$ | —$CH_2CH_3$ | N | CH | CH | $C(CF_3)$ | CH |
| 10.003 | CH | $SO_2CH_3$ | $C_3H_5$ | —$CH_2CH_3$ | N | CH | CH | $C(CF_3)$ | CH |
| 10.004 | CH | H | $CH_3$ | —$CH_2CH_3$ | N | CH | CH | $C(CF_3)$ | CH |
| 10.005 | CH | $CH_3$ | $CH_3$ | —$CH_2CH_3$ | N | CH | CH | $C(CF_3)$ | CH |
| 10.006 | CH | $SO_2CH_3$ | $CH_3$ | —$CH_2CH_3$ | N | CH | CH | $C(CF_3)$ | CH |
| 10.007 | N | H | $C_3H_5$ | —$CH_2CH_3$ | N | CH | CH | $C(CF_3)$ | CH |
| 10.008 | N | $CH_3$ | $C_3H_5$ | —$CH_2CH_3$ | N | CH | CH | $C(CF_3)$ | CH |
| 10.009 | N | $SO_2CH_3$ | $C_3H_5$ | —$CH_2CH_3$ | N | CH | CH | $C(CF_3)$ | CH |
| 10.010 | N | H | $CH_3$ | —$CH_2CH_3$ | N | CH | CH | $C(CF_3)$ | CH |
| 10.011 | N | $CH_3$ | $CH_3$ | —$CH_2CH_3$ | N | CH | CH | $C(CF_3)$ | CH |
| 10.012 | N | $SO_2CH_3$ | $CH_3$ | —$CH_2CH_3$ | N | CH | CH | $C(CF_3)$ | CH | and the N-oxides of the compounds of Table 10. $C_3H_5$ is cyclopropyl.

Table 11:

This table discloses the 12 compounds 11.001 to 11.012 of the formula I-4a, wherein X is SO, and A, $R_1$, $R_{10}$, $R_9$, $G_1$, $G_2$, $G_3$, $G_4$ and $G_5$ are as defined in Table 10.

Table 12:

This table discloses the 12 compounds 12.001 to 12.012 of the formula I-4a, wherein X is $SO_2$, and A, $R_1$, $R_{10}$, $R_9$, $G_1$, $G_2$, $G_3$, $G_4$ and $G_5$ are as defined in Table 10.

Table 13:

This table discloses the 10 compounds 13.001 to 13.010 of the formula I-5a:

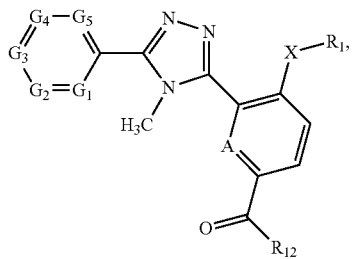

(I-5a)

wherein X is S, and A, $R_1$, $R_{12}$, $G_1$, $G_2$, $G_3$, $G_4$ and $G_5$ are as defined below:

TABLE 13

| Comp. No | A | $R_{12}$ | $R_1$ | $G_1$ | $G_2$ | $G_3$ | $G_4$ | $G_5$ |
|---|---|---|---|---|---|---|---|---|
| 13.001 | CH | OH | —CH$_2$CH$_3$ | N | CH | CH | C(CF$_3$) | CH |
| 13.002 | CH | OCH$_3$ | —CH$_2$CH$_3$ | N | CH | CH | C(CF$_3$) | CH |
| 13.003 | CH | H | —CH$_2$CH$_3$ | N | CH | CH | C(CF$_3$) | CH |
| 13.004 | CH | CH$_3$ | —CH$_2$CH$_3$ | N | CH | CH | C(CF$_3$) | CH |
| 13.005 | CH | OCH$_2$CH$_3$ | —CH$_2$CH$_3$ | N | CH | CH | C(CF$_3$) | CH |
| 13.006 | N | OH | —CH$_2$CH$_3$ | N | CH | CH | C(CF$_3$) | CH |
| 13.007 | N | OCH$_3$ | —CH$_2$CH$_3$ | N | CH | CH | C(CF$_3$) | CH |
| 13.008 | N | H | —CH$_2$CH$_3$ | N | CH | CH | C(CF$_3$) | CH |
| 13.009 | N | CH$_3$ | —CH$_2$CH$_3$ | N | CH | CH | C(CF$_3$) | CH |
| 13.010 | N | OCH$_2$CH$_3$ | —CH$_2$CH$_3$ | N | CH | CH | C(CF$_3$) | CH | and the N-oxides of the compounds of Table 13.

Table 14:

This table discloses the 10 compounds 14.001 to 14.010 of the formula I-5a, wherein X is SO, and A, $R_1$, $R_{12}$, $G_1$, $G_2$, $G_3$, $G_4$ and $G_5$ are as defined in Table 13.

Table 15:

This table discloses the 10 compounds 15.001 to 15.010 of the formula I-5a, wherein X is SO$_2$, and A, $R_1$, $R_{12}$, $G_1$, $G_2$, $G_3$, $G_4$ and $G_5$ are as defined in Table 13.

Table 16:

This table discloses the 10 compounds 16.001 to 16.010 of the formula I-6a:

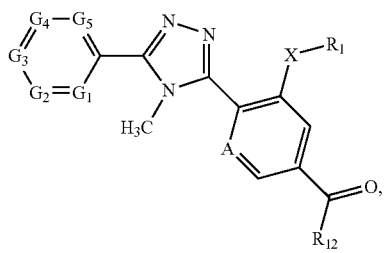

(I-6a)

wherein $X_2$ is S, and A, $R_1$, $R_{12}$, $G_1$, $G_2$, $G_3$, $G_4$ and $G_5$ are as defined below:

TABLE 16

| Comp. No | A | $R_{12}$ | $R_1$ | $G_1$ | $G_2$ | $G_3$ | $G_4$ | $G_5$ |
|---|---|---|---|---|---|---|---|---|
| 16.001 | CH | OH | —CH$_2$CH$_3$ | N | CH | CH | C(CF$_3$) | CH |
| 16.002 | CH | OCH$_3$ | —CH$_2$CH$_3$ | N | CH | CH | C(CF$_3$) | CH |
| 16.003 | CH | H | —CH$_2$CH$_3$ | N | CH | CH | C(CF$_3$) | CH |
| 16.004 | CH | CH$_3$ | —CH$_2$CH$_3$ | N | CH | CH | C(CF$_3$) | CH |
| 16.005 | CH | OCH$_2$CH$_3$ | —CH$_2$CH$_3$ | N | CH | CH | C(CF$_3$) | CH |
| 16.006 | N | OH | —CH$_2$CH$_3$ | N | CH | CH | C(CF$_3$) | CH |
| 16.007 | N | OCH$_3$ | —CH$_2$CH$_3$ | N | CH | CH | C(CF$_3$) | CH |
| 16.008 | N | H | —CH$_2$CH$_3$ | N | CH | CH | C(CF$_3$) | CH |
| 16.009 | N | CH$_3$ | —CH$_2$CH$_3$ | N | CH | CH | C(CF$_3$) | CH |
| 16.010 | N | OCH$_2$CH$_3$ | —CH$_2$CH$_3$ | N | CH | CH | C(CF$_3$) | CH | and the N-oxides of the compounds of Table 16.

Table 17:

This table discloses the 10 compounds 17.001 to 17.010 of the formula I-6a, wherein X is SO, and A, $R_1$, $R_{12}$, $G_1$, $G_2$, $G_3$, $G_4$ and $G_5$ are as defined in Table 16.

Table 18:

This table discloses the 10 compounds 18.001 to 18.010 of the formula I-6a, wherein X is SO$_2$, and A, $R_1$, $R_{12}$, $G_1$, $G_2$, $G_3$, $G_4$ and $G_5$ are as defined in Table 16.

Table 19:

This table discloses the 12 compounds 19.001 to 19.012 of the formula I-7a:

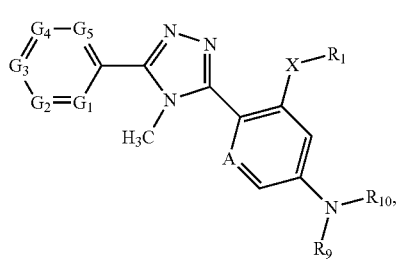

(I-7a)

wherein X is S, and A, $R_1$, $R_{11}$, $R_9$, $G_1$, $G_2$, $G_3$, $G_4$ and $G_5$ are as defined below:

TABLE 19

| Comp. No | A | $R_9$ | $R_{10}$ | $R_1$ | $G_1$ | $G_2$ | $G_3$ | $G_4$ | $G_5$ |
|---|---|---|---|---|---|---|---|---|---|
| 19.001 | CH | H | C$_3$H$_5$ | —CH$_2$CH$_3$ | N | CH | CH | C(CF$_3$) | CH |
| 19.002 | CH | CH$_3$ | C$_3$H$_5$ | —CH$_2$CH$_3$ | N | CH | CH | C(CF$_3$) | CH |
| 19.003 | CH | SO$_2$CH$_3$ | C$_3$H$_5$ | —CH$_2$CH$_3$ | N | CH | CH | C(CF$_3$) | CH |
| 19.004 | N | H | C$_3$H$_5$ | —CH$_2$CH$_3$ | N | CH | CH | C(CF$_3$) | CH |
| 19.005 | N | CH$_3$ | C$_3$H$_5$ | —CH$_2$CH$_3$ | N | CH | CH | C(CF$_3$) | CH |
| 19.006 | N | SO$_2$CH$_3$ | C$_3$H$_5$ | —CH$_2$CH$_3$ | N | CH | CH | C(CF$_3$) | CH |
| 19.007 | CH | H | CH$_3$ | —CH$_2$CH$_3$ | N | CH | CH | C(CF$_3$) | CH |

TABLE 19-continued

| Comp. No | A | R9 | R10 | R1 | G1 | G2 | G3 | G4 | G5 |
|---|---|---|---|---|---|---|---|---|---|
| 19.008 | CH | CH3 | CH3 | —CH2CH3 | N | CH | CH | C(CF3) | CH |
| 19.009 | CH | SO2CH3 | CH3 | —CH2CH3 | N | CH | CH | C(CF3) | CH |
| 19.010 | N | H | CH3 | —CH2CH3 | N | CH | CH | C(CF3) | CH |
| 19.011 | N | CH3 | CH3 | —CH2CH3 | N | CH | CH | C(CF3) | CH |
| 19.012 | N | SO2CH3 | CH3 | —CH2CH3 | N | CH | CH | C(CF3) | CH | and the N-oxides of the compounds of Table 19. $C_3H_5$ is cyclopropyl.

Table 20:
This table discloses the 12 compounds 20.001 to 20.012 of the formula I-7a, wherein X is SO, and A, $R_1$, $R_{11}$, $R_9$, $G_1$, $G_2$, $G_3$, $G_4$ and $G_5$ are as defined in Table 19.

Table 21:
This table discloses the 12 compounds 21.001 to 21.012 of the formula I-7a, wherein X is $SO_2$, and A, $R_1$, $R_{11}$, $R_9$, $G_1$, $G_2$, $G_3$, $G_4$ and $G_5$ are as defined in Table 19.

Table 22:
This table discloses the 12 compounds 22.001 to 22.012 of the formula I-8a:

Table 23:
This table discloses the 12 compounds 23.001 to 23.012 of the formula I-8a, wherein X is SO, and A, $R_1$, $R_{11}$, $R_9$, $G_1$, $G_2$, $G_3$, $G_4$ and $G_5$ are as defined in Table 22.

Table 24:
This table discloses the 12 compounds 24.001 to 24.012 of the formula I-8a, wherein X is $SO_2$, and A, $R_1$, $R_{11}$, $R_9$, $G_1$, $G_2$, $G_3$, $G_4$ and $G_5$ are as defined in Table 22.

Table 25:
This table discloses the 12 compounds 25.001 to 25.012 of the formula I-9a:

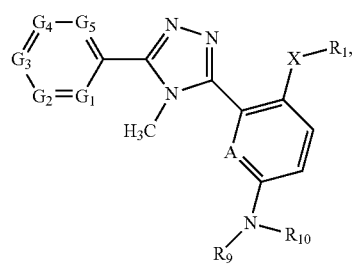

(I-8a)

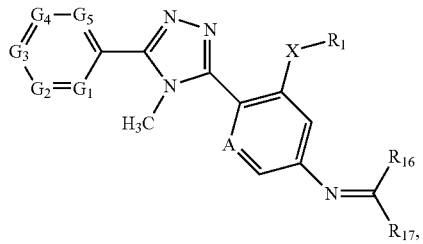

(I-9a)

wherein X is S, and A, $R_1$, $R_{10}$, $R_9$, $G_1$, $G_2$, $G_3$, $G_4$ and $G_5$ are as defined below:

wherein X is S, and A, $R_1$, $R_{16}$, $R_{17}$, $G_1$, $G_2$, $G_3$, $G_4$ and $G_5$ are as defined below:

TABLE 22

| Comp. No | A | R9 | R10 | R1 | G1 | G2 | G3 | G4 | G5 |
|---|---|---|---|---|---|---|---|---|---|
| 22.001 | CH | H | C3H5 | —CH2CH3 | N | CH | CH | C(CF3) | CH |
| 22.002 | CH | CH3 | C3H5 | —CH2CH3 | N | CH | CH | C(CF3) | CH |
| 22.003 | CH | SO2CH3 | C3H5 | —CH2CH3 | N | CH | CH | C(CF3) | CH |
| 22.004 | N | H | C3H5 | —CH2CH3 | N | CH | CH | C(CF3) | CH |
| 22.005 | N | CH3 | C3H5 | —CH2CH3 | N | CH | CH | C(CF3) | CH |
| 22.006 | N | SO2CH3 | C3H5 | —CH2CH3 | N | CH | CH | C(CF3) | CH |
| 22.007 | CH | H | CH3 | —CH2CH3 | N | CH | CH | C(CF3) | CH |
| 22.008 | CH | CH3 | CH3 | —CH2CH3 | N | CH | CH | C(CF3) | CH |
| 22.009 | CH | SO2CH3 | CH3 | —CH2CH3 | N | CH | CH | C(CF3) | CH |
| 22.010 | N | H | CH3 | —CH2CH3 | N | CH | CH | C(CF3) | CH |
| 22.011 | N | CH3 | CH3 | —CH2CH3 | N | CH | CH | C(CF3) | CH |
| 22.012 | N | SO2CH3 | CH3 | —CH2CH3 | N | CH | CH | C(CF3) | CH | and the N-oxides of the compounds of Table 22. $C_3H_5$ is cyclopropyl.

TABLE 25

| Comp. No | A | R16 | R17 | R1 | G1 | G2 | G3 | G4 | G5 |
|---|---|---|---|---|---|---|---|---|---|
| 25.001 | CH | H | C3H5 | —CH2CH3 | N | CH | CH | C(CF3) | CH |
| 25.002 | CH | CH3 | C3H5 | —CH2CH3 | N | CH | CH | C(CF3) | CH |
| 25.003 | CH | H | CH3 | —CH2CH3 | N | CH | CH | C(CF3) | CH |
| 25.004 | CH | CH3 | CH3 | —CH2CH3 | N | CH | CH | C(CF3) | CH |
| 25.005 | CH | H | NHOCH3 | —CH2CH3 | N | CH | CH | C(CF3) | CH |

TABLE 25-continued

| Comp. No | A | $R_{16}$ | $R_{17}$ | $R_1$ | $G_1$ | $G_2$ | $G_3$ | $G_4$ | $G_5$ |
|---|---|---|---|---|---|---|---|---|---|
| 25.006 | CH | $CH_3$ | $NHOCH_3$ | —$CH_2CH_3$ | N | CH | CH | $C(CF_3)$ | CH |
| 25.007 | N | H | $C_3H_5$ | —$CH_2CH_3$ | N | CH | CH | $C(CF_3)$ | CH |
| 25.008 | N | $CH_3$ | $C_3H_5$ | —$CH_2CH_3$ | N | CH | CH | $C(CF_3)$ | CH |
| 25.009 | N | H | $CH_3$ | —$CH_2CH_3$ | N | CH | CH | $C(CF_3)$ | CH |
| 25.010 | N | $CH_3$ | $CH_3$ | —$CH_2CH_3$ | N | CH | CH | $C(CF_3)$ | CH |
| 25.011 | N | H | $NHOCH_3$ | —$CH_2CH_3$ | N | CH | CH | $C(CF_3)$ | CH |
| 25.012 | N | $CH_3$ | $NHOCH_3$ | —$CH_2CH_3$ | N | CH | CH | $C(CF_3)$ | CH | and the N-oxides of the compounds of Table 25. $C_3H_5$ is cyclopropyl.

Table 26:
This table discloses the 12 compounds 26.001 to 26.012 of the formula I-9a, wherein X is SO, and A, $R_1$, $R_{11}$, $R_9$, $G_1$, $G_2$, $G_3$, $G_4$ and $G_5$ are as defined in Table 25.

Table 27:
This table discloses the 12 compounds 27.001 to 27.012 of the formula I-9a, wherein X is $SO_2$, and A, $R_1$, $R_{11}$, $R_9$, $G_1$, $G_2$, $G_3$, $G_4$ and $G_5$ are as defined in Table 25.

Table 28:
This table discloses the 12 compounds 28.001 to 28.012 of the formula I-10a:

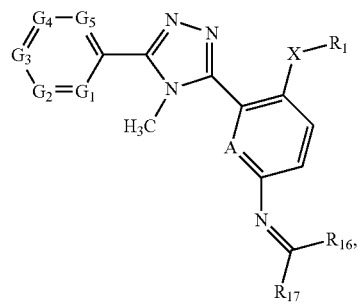

(I-10a)

wherein X is S, and A, $R_1$, $R_{16}$, $R_{17}$, $G_1$, $G_2$, $G_3$, $G_4$ and $G_5$ are as defined below:

Table 29:
This table discloses the 12 compounds 29.001 to 29.012 of the formula I-10a, wherein X is SO, and A, $R_1$, $R_{11}$, $R_9$, $G_1$, $G_2$, $G_3$, $G_4$ and $G_5$ are as defined in Table 28.

Table 30:
This table discloses the 12 compounds 30.001 to 30.012 of the formula I-10a, wherein X is $SO_2$, and A, $R_1$, $R_{11}$, $R_9$, $G_1$, $G_2$, $G_3$, $G_4$ and $G_5$ are as defined in Table 28.

Table 31:
This table discloses the 8 compounds 31.001 to 31.008 of the formula I-11a:

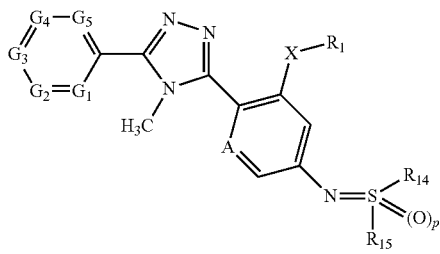

(I-11a)

wherein X is S, and A, $R_1$, $R_{14}$, $R_{15}$, $G_1$, $G_2$, $G_3$, $G_4$ and $G_5$ are as defined below:

TABLE 28

| Comp. No | A | $R_{16}$ | $R_{17}$ | $R_1$ | $G_1$ | $G_2$ | $G_3$ | $G_4$ | $G_5$ |
|---|---|---|---|---|---|---|---|---|---|
| 28.001 | CH | H | $C_3H_5$ | —$CH_2CH_3$ | N | CH | CH | $C(CF_3)$ | CH |
| 28.002 | CH | $CH_3$ | $C_3H_5$ | —$CH_2CH_3$ | N | CH | CH | $C(CF_3)$ | CH |
| 28.003 | CH | H | $CH_3$ | —$CH_2CH_3$ | N | CH | CH | $C(CF_3)$ | CH |
| 28.004 | CH | $CH_3$ | $CH_3$ | —$CH_2CH_3$ | N | CH | CH | $C(CF_3)$ | CH |
| 28.005 | CH | H | $NHOCH_3$ | —$CH_2CH_3$ | N | CH | CH | $C(CF_3)$ | CH |
| 28.006 | CH | $CH_3$ | $NHOCH_3$ | —$CH_2CH_3$ | N | CH | CH | $C(CF_3)$ | CH |
| 28.007 | N | H | $C_3H_5$ | —$CH_2CH_3$ | N | CH | CH | $C(CF_3)$ | CH |
| 28.008 | N | $CH_3$ | $C_3H_5$ | —$CH_2CH_3$ | N | CH | CH | $C(CF_3)$ | CH |
| 28.009 | N | H | $CH_3$ | —$CH_2CH_3$ | N | CH | CH | $C(CF_3)$ | CH |
| 28.010 | N | $CH_3$ | $CH_3$ | —$CH_2CH_3$ | N | CH | CH | $C(CF_3)$ | CH |
| 28.011 | N | H | $NHOCH_3$ | —$CH_2CH_3$ | N | CH | CH | $C(CF_3)$ | CH |
| 28.012 | N | $CH_3$ | $NHOCH_3$ | —$CH_2CH_3$ | N | CH | CH | $C(CF_3)$ | CH | and the N-oxides of the compounds of Table 28. $C_3H_5$ is cyclopropyl.

TABLE 31

| Comp. No | A | $R_{14}$ | $R_{15}$ | p | $R_1$ | $G_1$ | $G_2$ | $G_3$ | $G_4$ | $G_5$ |
|---|---|---|---|---|---|---|---|---|---|---|
| 31.001 | CH | $CH_3$ | $C_3H_5$ | 0 | —$CH_2CH_3$ | N | CH | CH | $C(CF_3)$ | CH |
| 31.002 | CH | $CH_3$ | $CH_3$ | 0 | —$CH_2CH_3$ | N | CH | CH | $C(CF_3)$ | CH |
| 31.003 | CH | $CH_3$ | $C_3H_5$ | 1 | —$CH_2CH_3$ | N | CH | CH | $C(CF_3)$ | CH |
| 31.004 | CH | $CH_3$ | $CH_3$ | 1 | —$CH_2CH_3$ | N | CH | CH | $C(CF_3)$ | CH |

TABLE 31-continued

| Comp. No | A | $R_{14}$ | $R_{15}$ | p | $R_1$ | $G_1$ | $G_2$ | $G_3$ | $G_4$ | $G_5$ |
|---|---|---|---|---|---|---|---|---|---|---|
| 31.005 | N | $CH_3$ | $C_3H_5$ | 0 | —$CH_2CH_3$ | N | CH | CH | $C(CF_3)$ | CH |
| 31.006 | N | $CH_3$ | $CH_3$ | 0 | —$CH_2CH_3$ | N | CH | CH | $C(CF_3)$ | CH |
| 31.007 | N | $CH_3$ | $C_3H_5$ | 1 | —$CH_2CH_3$ | N | CH | CH | $C(CF_3)$ | CH |
| 31.008 | C | $CH_3$ | $CH_3$ | 1 | —$CH_2CH_3$ | N | CH | CH | $C(CF_3)$ | CH | and the N-oxides of the compounds of Table 31. $C_3H_5$ is cyclopropyl.

Table 32:
This table discloses the 8 compounds 32.001 to 32.008 of the formula I-11a, wherein X is SO, and A, $R_1$, $R_{11}$, $R_9$, $G_1$, $G_2$, $G_3$, $G_4$ and $G_5$ are as defined in Table 31.

Table 33:
This table discloses the 8 compounds 33.001 to 33.008 of the formula I-11a, wherein X is $SO_2$, and A, $R_1$, $R_{11}$, $R_9$, $G_1$, $G_2$, $G_3$, $G_4$ and $G_5$ are as defined in Table 31.

Table 34:
This table discloses the 8 compounds 34.001 to 34.008 of the formula I-12a:

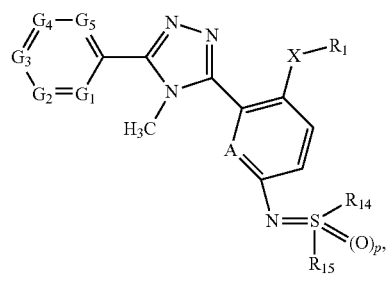

(I-12a)

wherein X is S, and A, $R_1$, $R_{14}$, $R_{15}$, $G_1$, $G_2$, $G_3$, $G_4$ and $G_5$ are as defined below:

TABLE 34

| Comp. No | A | $R_{14}$ | $R_{15}$ | p | $R_1$ | $G_1$ | $G_2$ | $G_3$ | $G_4$ | $G_5$ |
|---|---|---|---|---|---|---|---|---|---|---|
| 34.001 | CH | $CH_3$ | $C_3H_5$ | 0 | —$CH_2CH_3$ | N | CH | CH | $C(CF_3)$ | CH |
| 34.002 | CH | $CH_3$ | $CH_3$ | 0 | —$CH_2CH_3$ | N | CH | CH | $C(CF_3)$ | CH |
| 34.003 | CH | $CH_3$ | $C_3H_5$ | 1 | —$CH_2CH_3$ | N | CH | CH | $C(CF_3)$ | CH |
| 34.004 | CH | $CH_3$ | $CH_3$ | 1 | —$CH_2CH_3$ | N | CH | CH | $C(CF_3)$ | CH |
| 34.005 | N | $CH_3$ | $C_3H_5$ | 0 | —$CH_2CH_3$ | N | CH | CH | $C(CF_3)$ | CH |
| 34.006 | N | $CH_3$ | $CH_3$ | 0 | —$CH_2CH_3$ | N | CH | CH | $C(CF_3)$ | CH |
| 34.007 | N | $CH_3$ | $C_3H_5$ | 1 | —$CH_2CH_3$ | N | CH | CH | $C(CF_3)$ | CH |
| 34.008 | C | $CH_3$ | $CH_3$ | 1 | —$CH_2CH_3$ | N | CH | CH | $C(CF_3)$ | CH | and the N-oxides of the compounds of Table 34. $C_3H_5$ is cyclopropyl.

Table 35:
This table discloses the 8 compounds 35.001 to 35.008 of the formula I-12a, wherein X is SO, and A, $R_1$, $R_{11}$, $R_9$, $G_1$, $G_2$, $G_3$, $G_4$ and $G_5$ are as defined in Table 34.

Table 36:
This table discloses the 8 compounds 36.001 to 36.008 of the formula I-12a, wherein X is $SO_2$, and A, $R_1$, $R_{11}$, $R_9$, $G_1$, $G_2$, $G_3$, $G_4$ and $G_5$ are as defined in Table 34.

Table 37:
This table discloses the 6 compounds 37.001 to 37.006 of the formula I-13a:

(I-13a)

wherein X is S, and A, $R_1$, $R_9$, $R_{19}$, $G_1$, $G_2$, $G_3$, $G_4$ and $G_5$ are as defined below:

TABLE 37

| Comp. No | A | $R_9$ | $R_{19}$ | $R_1$ | $G_1$ | $G_2$ | $G_3$ | $G_4$ | $G_5$ |
|---|---|---|---|---|---|---|---|---|---|
| 37.001 | CH | $CH_3$ | $CH_3$ | —$CH_2CH_3$ | N | CH | CH | $C(CF_3)$ | CH |
| 37.002 | CH | $C_3H_5$ | $CH_3$ | —$CH_2CH_3$ | N | CH | CH | $C(CF_3)$ | CH |
| 37.003 | CH | $CH_3$ | $C_3H_5$ | —$CH_2CH_3$ | N | CH | CH | $C(CF_3)$ | CH |
| 37.004 | N | $CH_3$ | $CH_3$ | —$CH_2CH_3$ | N | CH | CH | $C(CF_3)$ | CH |
| 37.005 | N | $C_3H_5$ | $CH_3$ | —$CH_2CH_3$ | N | CH | CH | $C(CF_3)$ | CH |
| 37.006 | N | $CH_3$ | $C_3H_5$ | —$CH_2CH_3$ | N | CH | CH | $C(CF_3)$ | CH | and the N-oxides of the compounds of Table 37. $C_3H_5$ is cyclopropyl.

Table 38:
This table discloses the 6 compounds 38.001 to 38.006 of the formula I-13a, wherein X is SO, and A, $R_1$, $R_{11}$, $R_9$, $G_1$, $G_2$, $G_3$, $G_4$ and $G_5$ are as defined in Table 37.

Table 39:
This table discloses the 6 compounds 39.001 to 39.006 of the formula I-13a, wherein X is $SO_2$, and A, $R_1$, $R_{11}$, $R_9$, $G_1$, $G_2$, $G_3$, $G_4$ and $G_5$ are as defined in Table 37.

Table 40:
This table discloses the 6 compounds 40.001 to 40.006 of the formula I-14a:

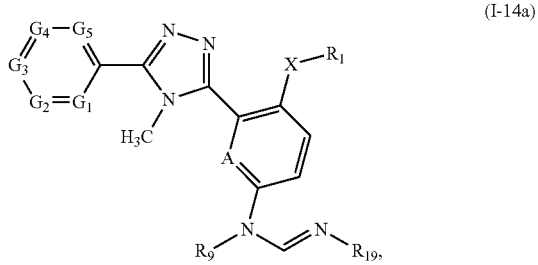

(I-14a)

wherein X is S, and A, $R_1$, $R_{11}$, $R_9$, $G_1$, $G_2$, $G_3$, $G_4$ and $G_5$ are as defined below:

TABLE 40

| Comp. No. | A | $R_9$ | $R_{19}$ | $R_1$ | $G_1$ | $G_2$ | $G_3$ | $G_4$ | $G_5$ |
|---|---|---|---|---|---|---|---|---|---|
| 40.001 | CH | $CH_3$ | $CH_3$ | —$CH_2CH_3$ | N | CH | CH | C($CF_3$) | CH |
| 40.002 | CH | $C_3H_5$ | $CH_3$ | —$CH_2CH_3$ | N | CH | CH | C($CF_3$) | CH |
| 40.003 | CH | $CH_3$ | $C_3H_5$ | —$CH_2CH_3$ | N | CH | CH | C($CF_3$) | CH |
| 40.004 | N | $CH_3$ | $CH_3$ | —$CH_2CH_3$ | N | CH | CH | C($CF_3$) | CH |
| 40.005 | N | $C_3H_5$ | $CH_3$ | —$CH_2CH_3$ | N | CH | CH | C($CF_3$) | CH |
| 40.006 | N | $CH_3$ | $C_3H_5$ | —$CH_2CH_3$ | N | CH | CH | C($CF_3$) | CH | and the N-oxides of the compounds of Table 40. $C_3H_5$ is cyclopropyl.

Table 41:

This table discloses the 6 compounds 41.001 to 41.006 of the formula I-14a, wherein X is SO, and A, $R_1$, $R_{11}$, $R_9$, $G_1$, $G_2$, $G_3$, $G_4$ and $G_5$ are as defined in Table 40.

Table 42:

This table discloses the 6 compounds 42.001 to 42.006 of the formula I-14a, wherein X is $SO_2$, and A, $R_1$, $R_{11}$, $R_9$, $G_1$, $G_2$, $G_3$, $G_4$ and $G_5$ are as defined in Table 40.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. *and Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp., *Rhodnius* spp., *Sahlbergella singularis*, *Scaptocoris castanea*, *Scotinophara* spp., *Thyanta* spp., *Triatoma* spp., *Vatiga illudens*; *Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii Scop.*, *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri Mats*, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada*

*gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;*
from the order Hymenoptera, for example,
*Acromyrmex, Arge* spp, *Atta* spp., *Cephus* spp., *Diprion* spp., *Diprionidae, Gilpinia polytoma, Hoplo-campa* spp., *Lasius* spp., *Monomorium pharaonis, Neodiprion* spp., *Pogonomyrmex* spp, *Slenopsis invicta, Solenopsis* spp. and *Vespa* spp.;
from the order Isoptera, for example,
*Coptotermes* spp, *Corniternes cumulans, Incisitermes* spp, *Macrotermes* spp, *Mastotermes* spp, *Microtermes* spp, *Reticulitermes* spp.; *Solenopsis geminate*
from the order Lepidoptera, for example,
*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp., *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;
from the order Mallophaga, for example,
*Damalinea* spp. and *Trichodectes* spp.;
from the order Orthoptera, for example,
*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;
from the order Psocoptera, for example,
*Liposcelis* spp.;
from the order Siphonaptera, for example,
*Ceratophyllus* spp., *Ctenocephalides* spp. and *Xenopsylla cheopis;*
from the order Thysanoptera, for example,
*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;
from the order Thysanura, for example, *Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubéreux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica,*

*Solanum melongena, Spinacea oleracea, Valerianella* spp. (*V. locusta, V. eriocarpa*) and *Vicia faba*.

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cystforming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species; *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp.,

*Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); *ochlodina; Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides*.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. kurstaki which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, *Sassafras*, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, *Viburnum*, Elm, Sourwood, Blueberry, *Rhododendron*, Azalea, Laurel, Poplar, Willow, Mulberry |
| | *Oncideres cingulata* | Hickory, Pecan, Persimmon, Elm, Sourwood, Basswood, Honeylocust, Dogwood, *Eucalyptus*, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |

TABLE B-continued

Examples of native woodborers of economic importance.

| Family | Species | Host or Crop Infested |
|---|---|---|
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-*stigmata*, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp., Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas* taignus and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| active ingredients | 40% |
|---|---|
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| active ingredients | 40% |
|---|---|
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent.

The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated. Common abbreviations: aq=aqueous, min=minute, h=hour, sat=saturated, $R_T$=retention time, mCPBA=meta-chloroperoxybenzoic acid, MeOH=methanol, EtOH=ethanol, $NaHCO_3$=sodium hydrogen carbonate, $Na_2CO_3$=sodium carbonate, HCl=hydrogen chloride, $CH_2Cl_2$=dichloromethane, $Et_3N$=triethylamine, DMF=N,N-dimethylformamide. Either one of the LCMS and/or GCMS methods below was used to characterize the compounds. The characteristic LCMS values obtained for each compound were the retention time ("Rt", recorded in minutes) and the measured molecular ion $(M+H)^+$.

LCMS and GCMS Methods:

Method 1 (ZCQ 13):

Spectra were recorded on a Mass Spectrometer from Waters (ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: 0 min 0% B, 100% A; 1.2-1.5 min 100% B; Flow (ml/min) 0.85.

Method 2:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH; gradient: 0 min 0% B, 100% A; 2.7-3.0 min 100% B; Flow (ml/min) 0.85.

Method 3:

GCMS analyses were performed on a Thermo Electron instrument where a TRACE GC ULTRA gas chromatograph (equipped with a Zebron Phenomenex ZB-5 ms 15 m, diam: 0.25 mm, 0.25 μm column; H₂ flow 1.2 mL/min; temp injector: 250° C.; temp detector: 220° C.; method: start at 70° C., then 25° C./min until 320° C., hold 2 min at 320° C.) was linked to a DSQ mass spectrometer characterizing the compounds by electron ionisation (EI).

Example P1: Preparation of N-[5-ethylsulfanyl-6-[4-methyl-5-[4-(trifluoromethyl)-2-pyridyl]-1,2,4-triazol-3-yl]-3-pyridyl]cyclopropanecarboxamide A1 and N-[5-ethylsulfonyl-6-[4-methyl-5-[4-(trifluoromethyl)-2-pyridyl]-1,2,4-triazol-3-yl]-3-pyridyl]cyclopropanecarboxamide A2

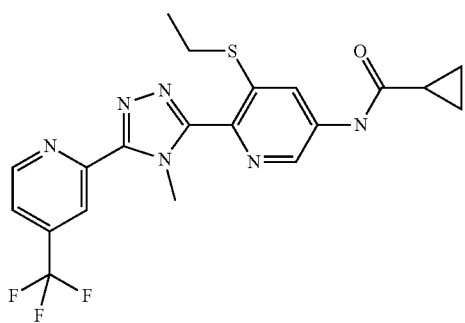

A1

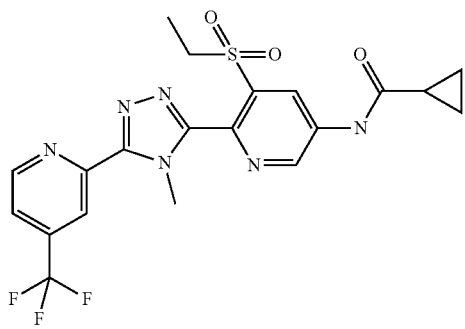

A2

Step A-1: Preparation of N-methyl-4-(trifluoromethyl)pyridine-2-carboxamide

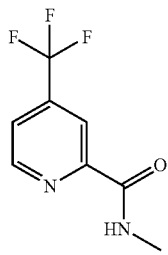

To a solution of 4-(trifluoromethyl)pyridine-2-carboxylic acid (97%, 10.0 g, 50.76 mmol) in dichloromethane (200 ml) was added dropwise N,N-dimethylformamide (0.1 ml) and oxalyl chloride (5.66 ml, 66.00 mmol). The reaction mixture was stirred at ambient temperature for 15 hours, then concentrated to dryness in vacuo to afford 4-(trifluoromethyl)pyridine-2-carbonyl chloride (10.5 g) as a solid.

To methylamine (2M in tetrahydrofuran) (62.6 ml, 125.2 mmol) in tetrahydrofuran (40 ml) at 0-5° C. was added triethylamine (10.4 ml, 75.03 mmol), followed by a solution of 4-(trifluoromethyl)pyridine-2-carbonyl chloride (10.5 g, 50.11 mmol, preparation above) in tetrahydrofuran (60 ml) dropwise. The mixture was allowed to warm to ambient temperature, and stirred for 2 hours. The resulting suspension was filtered, the solid residue washed with t-butyl methyl ether (3×) and the filtrate evaporated under reduced pressure. The residue was dissolved in t-butyl methyl ether, the organic phase washed with water (3×) and brine, dried over sodium sulfate and concentrated in vacuo. The crude material was diluted with t-butyl methyl ether, treated with activated charcoal, the mixture stirred for 15 minutes and filtered. Evaporation of the filtrate in vacuo afforded N-methyl-4-(trifluoromethyl)pyridine-2-carbox-amide as a solid (9.2 g), Mp 60-62° C. This material was used without further purification. LCMS (method 2): 205 (M+H)+; retention time: 0.86 min. ¹H-NMR (CDCl₃) δ ppm 3.07 (d, 3H), 7.66 (d, 1H), 8.01 (br s, 1H), 8.45 (s, 1H), 8.74 (d, 1H).

Step A-2: Preparation of N-methyl-4-(trifluoromethyl)pyridine-2-carbothioamide

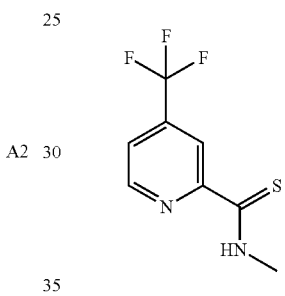

To a solution of N-methyl-4-(trifluoromethyl)pyridine-2-carboxamide (32.5 g, 159.2 mmol) in pyridine (870 ml) was added phosphorus pentasulfide (42.5 g, 95.6 mmol) and the mixture was stirred at reflux temperature for 5 hours. After cooling, the solvent was removed in vacuo, the residue diluted with water and the aqueous phase extracted with diethyl ether (3×). The combined organic layers were washed with a water/brine (1:1) solution (4×), dried over sodium sulfate and concentrated under reduced pressure to afford N-methyl-4-(trifluoromethyl)pyridine-2-carbothioamide as a solid (30.9 g), Mp 69-70° C. This material was used without further purification. LCMS (method 2): 221 (M+H)+; retention time: 1.42 min. ¹H-NMR (CDCl₃) δ ppm 3.43 (d, 3H), 7.66 (d, 1H), 8.68 (d, 1H), 8.96 (s, 1H), 10.14 (br s, 1H).

Step A-3: Preparation of ethyl N-methyl-4-(trifluoromethyl)pyridine-2-carboximidothioate

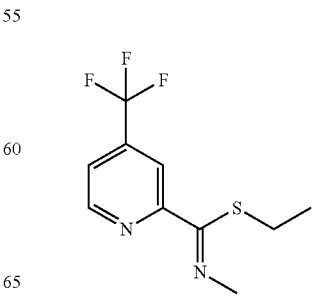

To a solution of N-methyl-4-(trifluoromethyl)pyridine-2-carbothioamide (10.2 g, 46.32 mmol) in ethanol (200 ml) was added sodium ethoxide (21 wt % in EtOH) (15.2 g, 46.3 mmol, 17.3 ml) and the mixture was stirred at ambient temperature for 40 minutes. Iodoethane (14.5 g, 92.68 mmol, 7.49 ml) was added and stirring continued at ambient temperature for 15 hours. The reaction mixture was concentrated in vacuo, diluted with t-butyl methyl ether, the organic phase washed successively with water (3×), a sat. aqueous sodium carbonate solution and brine, dried over sodium sulfate and evaporated under reduced pressure to afford ethyl N-methyl-4-(trifluoromethyl)pyridine-2-carboximidothioate, as a liquid (10.4 g). This material was used without further purification LCMS (method 2): 249 (M+H)+; retention time: 1.20 min. $^1$H-NMR (CDCl$_3$, major isomer) δ ppm 1.15 (t, 3H), 2.87 (q, 2H), 3.53 (s, 3H), 7.55 (d, 1H), 7.91 (s, 1H), 8.84 (d, 1H).

Step B-1: Preparation of
5-bromo-3-ethylsulfanyl-pyridine-2-carbonitrile

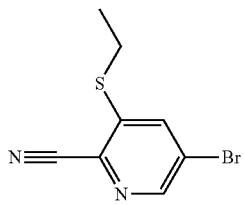

Under nitrogen atmosphere, a solution of 5-bromo-3-fluoro-pyridine-2-carbonitrile (1.005 g, 5.00 mmol) in dry N,N-dimethylformamide (15 ml) was cooled to −50° C. and to this was added dropwise a freshly prepared solution of sodium ethanethiolate (0.429 g, 5.10 mmol) in dry N,N-dimethylformamide (5 ml).

After stirring at −50° C. for 30 minutes, the cooling bath was removed and the mixture was allowed to warm to ambient temperature. Water and brine were added and the aqueous mixture was extracted with ethyl acetate. After separation, the organic layer was washed twice with brine, dried over sodium sulfate and concentrated. The crude product was purified over silica by flash column chromatography (0 to 40% gradient of ethyl acetate in heptane) to afford the title compound (0.93 g) as a solid. GCMS (method 3): 242/244 (M)$^+$, retention time 6.33 min. $^1$H-NMR (CDCl$_3$) d ppm 1.41 (3H), 3.06 (2H), 7.82 (1H), 8.49 (1H).

Alternative preparation method: Under nitrogen atmosphere, a solution of 5-bromo-3-nitro-pyridine-2-carbonitrile (45.35 g, 199 mmol) in dry N,N-dimethylformamide (500 ml) was cooled to −50° C. and to this was added dropwise a freshly prepared solution of sodium ethanethiolate (17.4 g, 207 mmol) in dry N,N-dimethylformamide (200 ml) (not a completely clear solution). After complete addition, stirring was continued at −50° C. for 30 minutes. Water and brine were added and the cooling bath was removed. The aqueous mixture was extracted with ethyl acetate. After separation, the water layer was extracted with ethyl acetate once more. The combined the organic layers were washed twice with brine, dried over sodium sulfate and concentrated. The crude product was purified over silica by flash column chromatography (0 to 25% gradient of ethyl acetate in heptane) to afford the title compound (33.9 g) as a solid. LCMS (method 1): 243/245 (M+H); retention time: 0.95 min.

Step B-2: Preparation of
5-bromo-3-ethylsulfanyl-pyridine-2-carboxylic Acid

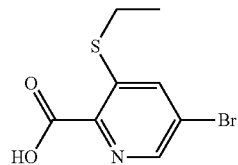

A solution of 5-bromo-3-ethylsulfanyl-pyridine-2-carbonitrile (43 g, 170 mmol, 1.0 eq.) in 800 ml aqueous hydrogen chloride HCl 32% was heated to 60° C. overnight. Dioxane (100 ml) was added and the mixture was further stirred at 60° C. for 48 h. The reaction mixture was cooled to 0-5° C., treated with an aqueous sodium hydroxide solution (NaOH 30%) until pH11 and washed with 2×200 ml tert-butyl methyl ether. The water phase was acidified with HCl 10% back to pH4, the resulting solid was filtrated, washed with water and dried in vacuo. LCMS (method 1): 262, 264 (M+H); retention time: 0.77 min. $^1$H NMR (400 MHz, CDCl$_3$) δ ppm: 8.50 (s, 1H); 8.06 (s, 1H); 3.03 (q, 2H); 1.24 (t, 3H).

Step B-3: Preparation of methyl
5-bromo-3-ethylsulfanyl-pyridine-2-carboxylate

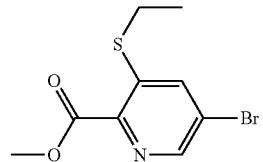

To a suspension of 5-bromo-3-ethylsulfanyl-pyridine-2-carboxylic acid (15.0 g, 57.23 mmol) in methanol (350 ml) was added sulfuric acid (0.5 ml) and the mixture stirred at reflux overnight. After cooling, the solution was concentrated under reduced pressure. The residue was triturated with diethyl ether (200 ml), the suspension filtered, the solid washed with cold diethyl ether and dried in vacuo to afford methyl 5-bromo-3-ethylsulfanyl-pyridine-2-carboxylate (13.9 g) as a solid, Mp 72-74° C. LCMS (method 1): 276/278 (M+H)$^+$, retention time 0.98 min. $^1$H-NMR (CDCl$_3$) d ppm 1.42 (3H), 2.94 (2H), 4.00 (3H), 7.78 (1H), 8.46 (1H).

Step B-4: Preparation of
5-bromo-3-ethylsulfanyl-pyridine-2-carbohydrazide

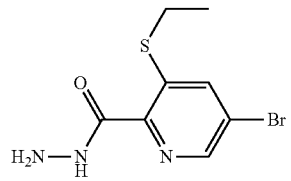

To a solution of methyl 5-bromo-3-ethylsulfanyl-pyridine-2-carboxylate (19.8 g, 71.70 mmol) in methanol (300 ml) was added hydrazine monohydrate (4.62 ml, 93.2 mmol) and the mixture stirred at reflux for 4 hours. After cooling, the reaction mixture was concentrated under reduced pressure, the residue suspended in diethyl ether, filtered and the solid washed with cold diethyl ether and dried in vacuo to afford 5-bromo-3-ethylsulfanyl-pyridine-2-carbohydrazide (17.2 g) as a solid, Mp 136-138° C. LCMS (method 1): 276/278 (M+H)$^+$, retention time 0.75 min. $^1$H-NMR (CDCl$_3$) δ ppm 1.42 (3H), 2.91 (2H), 4.02 (2H), 7.75 (1H), 8.28 (1H), 8.82 (1H).

Step C-1: Preparation of 5-bromo-3-ethylsulfanyl-2-[4-methyl-5-[4-(trifluoromethyl)-2-pyridyl]-1,2,4-triazol-3-yl]pyridine

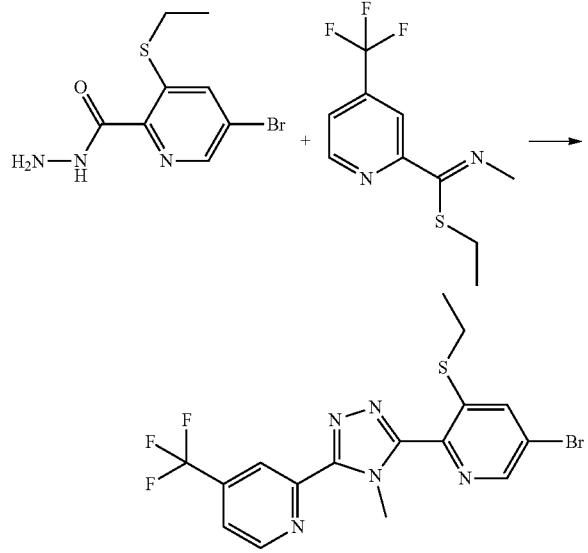

A solution of 5-bromo-3-ethylsulfanyl-pyridine-2-carbohydrazide (556 mg, 2.014 mmol) and ethyl N-methyl-4-(trifluoromethyl)pyridine-2-carboximidothioate (500 mg, 2.014 mmol) in ethanol (5 ml) was heated in the microwave at 150° C. for 30 minutes. After cooling, the reaction mixture was concentrated under reduced pressure and the residue purified over silica by flash column chromatography (0-25% ethyl acetate gradient in cyclohexane) to afford 5-bromo-3-ethylsulfanyl-2-[4-methyl-5-[4-(trifluoro-methyl)-2-pyridyl]-1,2,4-triazol-3-yl]pyridine as a solid (700 mg), Mp 122-123° C. LCMS (method 1): 444/446 (M+H)$^+$, retention time 1.04 min. $^1$H-NMR (CDCl$_3$) δ ppm 1.36 (3H), 2.97 (2H), 4.14 (3H), 7.58 (1H), 7.86 (1H), 8.55 (1H), 8.70 (1H), 8.87 (1H).

Alternative preparation method: To a solution of ethyl N-methyl-4-(trifluoromethyl)pyridine-2-carboximidothioate (3.0 g, estimated 90%, 10.88 mmol) in pyridine (12 ml) which was purged with argon for 10 minutes was added 5-bromo-3-ethylsulfanyl-pyridine-2-carbohydrazide (3.0 g, 10.88 mmol). The mixture was heated in the microwave at 180° C. for 40 minutes. After cooling, the reaction mixture was poured into ice-water, stirred for 10 minutes, the suspension filtered and the solid washed with cold water. This solid was dissolved in dichloromethane, the solution dried over sodium sulfate and concentrated to dryness under reduced pressure to afford 5-bromo-3-ethylsulfanyl-2-[4-methyl-5-[4-(trifluoro-methyl)-2-pyridyl]-1,2,4-triazol-3-yl]pyridine as a solid (4.3 g), which was used without further purification.

Step C-2: Preparation of 5-bromo-3-ethylsulfonyl-2-[4-methyl-5-[4-(trifluoromethyl)-2-pyridyl]-1,2,4-triazol-3-yl]pyridine

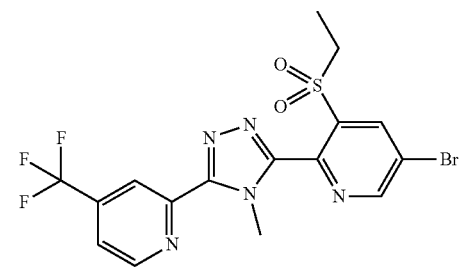 [SMILES: CCS(=O)(=O)c1cc(Br)cnc1-c1nnc(-c2cc(C(F)(F)F)ccn2)n1C]

To a solution of 5-bromo-3-ethylsulfanyl-2-[4-methyl-5-[4-(trifluoromethyl)-2-pyridyl]-1,2,4-triazol-3-yl]pyridine (4.0 g, 9.00 mmol) in dichloromethane (50 ml) at 10° C. was added m-CPBA (75 wt % in water) (4.25 g, 18.46 mmol, 75%) in four portions and the mixture was stirred at 5° C. for 2 hours, then at ambient temperature overnight. The reaction mixture was diluted with tert-butyl methyl ether, washed successively with a saturated aqueous solution of sodium bisulfite solution (2×), saturated aqueous solution of sodium hydrogen carbonate (4×) and brine, dried over sodium sulfate and concentrated under reduced pressure. The residue was triturated with diethyl ether, the suspension filtered, the solid washed with cold diethyl ether and dried in vacuo to afford 5-bromo-3-ethylsulfonyl-2-[4-methyl-5-[4-(trifluoromethyl)-2-pyridyl]-1,2,4-triazol-3-yl]pyridine as a solid (3.6 g), Mp 173-175° C. LCMS (method 1): 476/478 (M+H)$^+$, retention time 1.03 min. $^1$H-NMR (400 MHz, CDCl$_3$) δ ppm 1.39 (t, 3H) 3.85 (m, 2H) 4.07 (s, 3H) 7.60 (m, 1H) 8.66 (d, 1H) 8.69 (s, 1H) 8.87 (d, 1H) 9.06 (d, 1H)

Step D-1: N-[5-ethylsulfanyl-6-[4-methyl-5-[4-(trifluoromethyl)-2-pyridyl]-1,2,4-triazol-3-yl]-3-pyridyl]cyclopropanecarboxamide A1

To a solution of 5-bromo-3-ethylsulfanyl-2-[4-methyl-5-[4-(trifluoromethyl)-2-pyridyl]-1,2,4-triazol-3-yl]pyridine (Prepared as described before, 0.2 g, 0.45 mmol), cyclopropanecarboxamide (38.3 mg, 0.45 mmol), dicesium carbonate (0.51 g, 0.45 mmol) and (5-diphenylphosphanyl-9,9-dimethyl-xanthen-4-yl)-diphenyl-phosphane (13.4 mg, 0.023 mmol) in 1,4-dioxane (3.6 mL) was added (1E,4E)-1,5-diphenylpenta-1,4-dien-3-one; palladium (4.25 mg, 0.0045 mmol) under argon atmosphere at ambient temperature. The mixture heated at 95° C. The reaction mixture was poured to a mixture of water and ethyl acetate. The organic phase was separated and the aqueous phase was extracted 2 times with ethyl acetate. Combinated organic phases were dried on magnesium sulfate and concentrated under vacuum. The crude product was purified over a silica gel cartridge (Rf200), eluting with DCM/MeOH to give the title compound (86% yield). LCMS (method 1): 449 (M+H)$^+$, retention time 0.97 min. $^1$H NMR (400 MHz, CHCl$_3$) δ ppm 0.89 (m, 2H) 1.06 (m, 2H) 1.26-1.31 (m, 3H) 1.79 (m, 1H) 2.90 (m, 2H) 4.04 (s, 3H) 7.59 (d, 1H) 8.16 (d, 1H) 8.35 (d, 1H) 8.66 (s, 1H) 8.81 (m, 1H) 9.59 (s, 1H).

Step D-2: N-[5-ethylsulfonyl-6-[4-methyl-5-[4-(trifluoromethyl)-2-pyridyl]-1,2,4-triazol-3-yl]-3-pyridyl]cyclopropanecarboxamide A2

To a solution of N-[5-ethylsulfanyl-6-[4-methyl-5-[4-(trifluoromethyl)-2-pyridyl]-1,2,4-triazol-3-yl]-3-pyridyl]cyclopropanecarboxamide A1 (0.119 g, 0.26 mmol) in dichloromethane (5.3 ml) at 0° C. was added mCPBA (75 wt % in water) (0.157 g, 0.63 mmol, 75%) and the mixture was stirred at ambient temperature for 2 hours. The reaction mixture was diluted with a mixture of water and dichloromethane, the aqueous phase was extracted 2× with dichloromethane. The combined organic phases were washed successively with a saturated aqueous solution of sodium bisulfite solution (2×), saturated aqueous solution of sodium hydrogen carbonate (10% in water) and with a solution of sodium hydroxide (1N), dried over sodium sulfate and concentrated under reduced pressure. The residue was purified over silica by flash column chromatography (ethyl acetate/cyclohexane) to afford N-[5-ethylsulfonyl-6-[4-methyl-5-[4-(trifluoromethyl)-2-pyridyl]-1,2,4-triazol-3-yl]-3-pyridyl]cyclopropanecarboxamide A2 as a solid (0.11 g, 86.3% yield). LCMS (method 1): 481 (M+H)$^+$, retention time 0.92 min. $^1$H-NMR (CDCl$_3$) δ ppm 9.37 (d, 1H), 8.86 (d, 1H), 8.67 (s, 1H), 8.63 (d, 1H), 8.59 (s, 1H), 7.58 (d, 1H), 4.03 (s, 3H), 3.80 (q, 2H), 1.68 (m, 1H), 1.36 (t, 3H), 0.95 (m, 2H) 1.16 (m, 2H).

Example P2: Preparation of 5-ethylsulfonyl-6-[4-methyl-5-[4-(trifluoromethyl)-2-pyridyl]-1,2,4-triazol-3-yl]pyridine-3-carbaldehyde A3

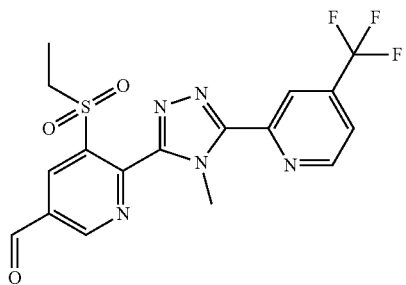

A3

Step A: Preparation of 3-ethylsulfonyl-2-[4-methyl-5-[4-(trifluoromethyl)-2-pyridyl]-1,2,4-triazol-3-yl]-5-vinyl-pyridine

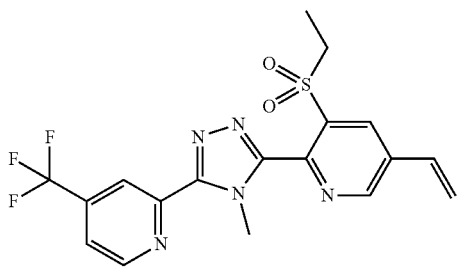 [SMILES: C=Cc1cnc(-c2nnc(-c3cc(C(F)(F)F)ccn3)n2C)c(S(=O)(=O)CC)c1]

Each of two microwave vials were charged with 5-bromo-3-ethylsulfonyl-2-[4-methyl-5-[4-(trifluoro-methyl)-2-pyridyl]-1,2,4-triazol-3-yl]pyridine (Prepared before: example P1, step C-2, 500 mg, 1.050 mmol), dibutoxy(vinyl)borane (0.477 ml, 2.10 mmol) and an aqueous 2M sodium carbonate solution (1.57 ml, 2.0M, 3.14 mmol) in acetonitrile (12 ml). Each mixture was purged with argon for 5 minutes, then chloro(2-dicyclohexylphosphino-2',4',6'-triisopropyl-1,1'-biphenyl)[2-(2'-amino-1,1'-biphenyl)]palladium(II) (82 mg, 0.105 mmol) was added, the vials were capped and stirred in the microwave at 120° C. for 10 minutes. Both reactions were pooled for workup: after dilution with saturated aqueous solution of sodium hydrogen carbonate, the mixture was extracted twice with dichloromethane, the combined organic layers dried over sodium sulfate and concentrated. The residue was purified over silica by flash column chromatography (0-70% ethyl acetate gradient in cyclohexane) to afford 3-ethylsulfonyl-2-[4-methyl-5-[4-(trifluoromethyl)-2-pyridyl]-1,2,4-triazol-3-yl]-5-vinyl-pyridine (title compound P12) as a solid (615 mg), Mp 67-70° C. LCMS (method 1): 424 (M+H)$^+$, retention time 0.97 min. $^1$H-NMR (CDCl$_3$) δ ppm 1.38 (3H), 3.82 (2H), 4.06 (3H), 5.70 (d, 1H), 6.12 (d, 1H), 6.86 (dd, 1H), 7.59 (1H), 8.50 (1H), 8.70 (1H), 8.86 (1H), 8.97 (1H).

Step K: Preparation of 1-[5-ethylsulfonyl-6-[4-methyl-5-[4-(trifluoromethyl)-2-pyridyl]-1,2,4-triazol-3-yl]-3-pyridyl]ethane-1,2-diol

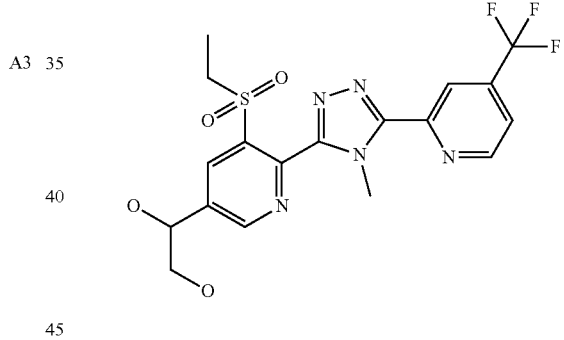

A solution of 3-ethylsulfonyl-2-[4-methyl-5-[4-(trifluoromethyl)-2-pyridyl]-1,2,4-triazol-3-yl]-5-vinyl-pyridine (0.6 g, 1.417 mmol) in tBuOH/water 1:1 (18 mL) (brown suspension), was treated with AD-Mix-Beta™ (2.324 g, 2.834 mmol) at (0° C.). The orange suspension was stirred 30 min at 0° C., and then 2 hours at ambient temperature. The mixture was cooled down to 5° C. and treated with sodium sulfite (2.26 g, 17.01 mmol) was added, and the reaction mixture allowed to warm to ambient temperature and stirred for 2 hours. The mixture was saturated with NaCl and extracted 3× with EtOAc. The combined organic phases were dried over Na2SO4, filtered and concentrated in vacuo. The crude product was used in the next step without further purification. LCMS (method 1): 458 (M+H)$^+$, retention time 0.77 min. $^1$H NMR (400 MHz, CDCl$_3$) δ ppm 1.36 (t, 3H) 2.42 (br. s., 1H) 3.31 (br. s., 1H) 3.68-3.85 (m, 4H) 3.98 (dd, 1H) 4.05 (s, 3H) 5.09 (dd, 1H) 7.60 (d, 1H) 8.53 (d, 1H) 8.70 (s, 1H) 8.87 (d, 1H) 9.02 (d, 1H).

Step L: Preparation of 5-ethylsulfonyl-6-[4-methyl-5-[4-(trifluoromethyl)-2-pyridyl]-1,2,4-triazol-3-yl]pyridine-3-carbaldehyde A3

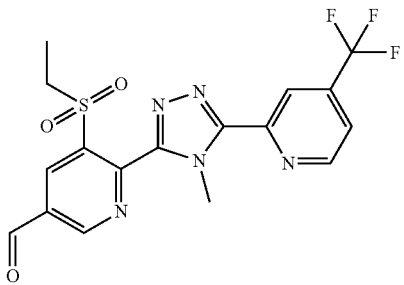

A3

A sample of 1-[5-ethylsulfonyl-6-[4-methyl-5-[4-(trifluoromethyl)-2-pyridyl]-1,2,4-triazol-3-yl]-3-pyridyl]ethane-1,2-diol (0.5 g, 1.093 mmol) dissolved in acetone (115 mL, 203 mmol) and water (15 mL) was treated with sodium periodate (0.4723 g, 2.186 mmol) at ambient temperature. The reaction mixture was stirred for 2 hours by which time TLC analysis showed reaction completion. The reaction mixture was diluted with water and EtOAc, and the organic layer separated. The aqueous phase was back-extracted with EtOAc, washed with sat. NaCl sol., dried over Na2SO4, filtered and concentrated in vacuo. The crude product was purified by combi flash chromatography with a column of 12 g and a gradient of dichloromethane+0-10% methanol, to give the title product. LCMS (method 1): 426 (M+H)$^+$, retention time 0.93 min. $^1$H NMR (400 MHz, CDCl$_3$) δ ppm 1.43 (t, 3H) 3.94 (q, 2H) 4.14 (s, 3H) 7.62 (d, 1H) 8.72 (d, 1H) 8.90 (d, 1H) 8.97 (dl H) 9.44 (d, 1H) 10.32 (s, 1H).

Example P3: Preparation of 1-[5-ethylsulfonyl-6-[4-methyl-5-[4-(trifluoromethyl)-2-pyridyl]-1,2,4-triazol-3-yl]-3-pyridyl]ethanone A4

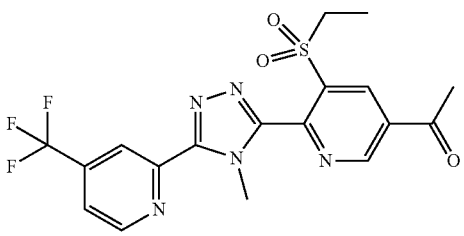

A4

Step A: Preparation of 5-(1-ethoxyvinyl)-3-ethylsulfonyl-2-[4-methyl-5-[4-(trifluoromethyl)-2-pyridyl]-1,2,4-triazol-3-yl]pyridine

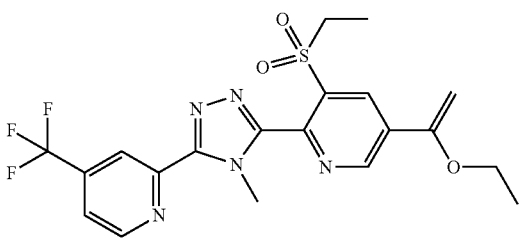 [SMILES: C=C(OCC)c1cnc(-c2nnc(-c3cc(C(F)(F)F)ccn3)n2C)c(S(=O)(=O)CC)c1]

A solution of 5-bromo-3-ethylsulfonyl-2-[4-methyl-5-[4-(trifluoromethyl)-2-pyridyl]-1,2,4-triazol-3-yl]pyridine (0.38 g, 0.80 mmol, step I from example P2) and tributyl(1-ethoxyvinyl)stannane (0.32 g, 0.84 mmol) in 1,4-dioxane (4.0 mL) was degassed with an argon flux for 10 minutes. To this yellow solution was added tetrakis(triphenylphosphine)palladium(0) (0.019 g, 0.016 mmol) at ambient temperature and the reaction mixture then irradiated in the microwave oven for 1 h at 130° C. LCMS analysis showed reaction completion after this time. The reaction mixture was quenched with saturated aqueous solution of NaHCO$_3$ (4 mL) and NaOH 1N (4 ml) at RT, and the mixture was vigorously stirred for 3 h. The mixture was then extracted with EtOAc (×3). The combined organic phases were washed with water and brine, dried over Na$_2$SO$_4$, filtrated and concentrated in vacuo. The crude product was purified over a silica gel cartridge (Rf200), eluting with cyclohexane/EtOAc, to give the title compound as a colourless resin. LCMS (method 1): 468 (M+H)+; retention time: 1.08 min. $^1$H NMR (400 MHz, CDCl$_3$) δ ppm 1.38 (t, 3H) 1.49 (t, 3H) 3.81 (q, 2H) 3.98-4.05 (m, 2H) 4.05 (s, 3H) 4.49-4.58 (m, 1H) 4.96 (d, 1H) 7.58 (d, 1H) 8.66 (d, 1H) 8.70 (s, 1H) 8.86 (d, 1H) 9.20 (d, 1H).

Step B: 1-[5-ethylsulfonyl-6-[4-methyl-5-[4-(trifluoromethyl)-2-pyridyl]-1,2,4-triazol-3-yl]-3-pyridyl]ethanone, A4

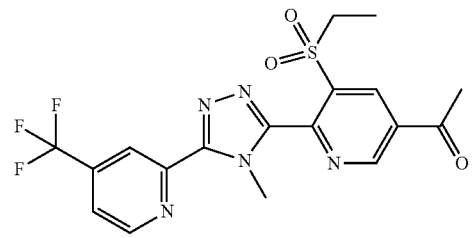

A4

5-(1-ethoxyvinyl)-3-ethylsulfonyl-2-[4-methyl-5-[4-(trifluoromethyl)-2-pyridyl]-1,2,4-triazol-3-yl]pyridine (0.26 g, 0.56 mmol) was dissolved in methanol (5.0 mL) and 10% aqueous HCl (2.8 mL) was added at ambient temperature. The mixture was stirred at ambient temperature for 15 hours. LCMS analysis showed reaction completion after this time. The MeOH was removed on a rotary evaporator, and the residue taken up in EtOAc and washed with saturated aqueous NaHCO$_3$. The water phase was back extracted with EtOAc, and the combined organic phases washed with water and brine, dried over Na$_2$SO$_4$, filtered and concentrated in vacuo to give the title compound as beige solid. LCMS (method 1): 440 (M+H)+; retention time: 0.94 min. $^1$H NMR (400 MHz, CDCl$_3$) δ ppm 1.41 (t, 3H) 2.79 (s, 3H) 3.91 (q, 2H) 4.11 (s, 3H) 7.61 (dd, 1H) 8.71 (s, 1H) 8.89 (d, 1H) 8.98 (d, 1H) 9.49 (d, 1H).

Example P4: Preparation of N-cyclopropyl-5-ethylsulfonyl-6-[4-methyl-5-[4-(trifluoromethyl)-2-pyridyl]-1,2,4-triazol-3-yl]pyridin-2-amine A5

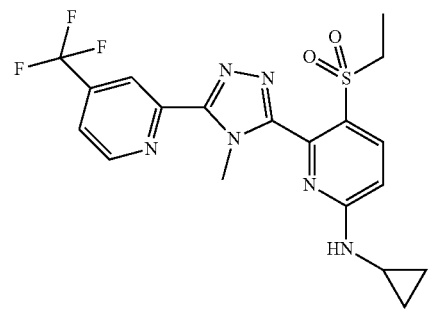

A5

Step A: Preparation of methyl 6-chloro-3-ethylsulfanyl-pyridine-2-carboxylate

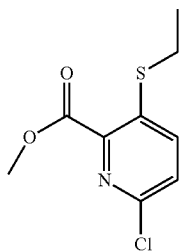

A solution of methyl 3,6-dichloropyridine-2-carboxylate (20 g, 97.073 mmol, commercial compound) in tetrahydrofuran (200 mL) was treated with catalytic quantities of 18-crown-6-ether (ca. 300 mg) followed by sodium ethoxide (9.073 g, 97.073 mmol) in 3 portions. The reaction was then allowed to stir at ambient temperature for 1 hour. LCMS analysis after this time showed consumption of starting materials and the formation of three new products. The reaction mixture was poured on 100 ml saturated ammonium chloride aqueous solution, extracted with 2×100 ml EtOAc, and the combined organic layers washed with 2×50 ml saturated aqueous ammonium chloride aqueous solution, 3×100 ml water, dried over $Na_2SO_4$, filtered and concentrated in vacuo. The crude product was purified by combi flash chromatography with a column of 220 g and a gradient cyclohexane+0-10% EtOAc. This gave as the first eluting product methyl 3,6-bis(ethylsulfanyl)pyridine-2-carboxylate (method 1, retention time 1.04 mins, (MH+)=258). The second product to elute was methyl 3-chloro-6-ethylsulfanyl-pyridine-2-carboxylate (method 1, retention time 0.99 min, (MH+) 232). The final product to elute was the major product and desired title product, as white crystals. $^1$H NMR (400 MHz, $CDCl_3$) δ ppm 1.40 (t, 3H) 2.95 (q, 2H) 4.00 (s, 3H) 7.41 (d, 1H) 7.66 (d, 1H).

Step B: Preparation of methyl 6-chloro-3-ethylsulfonyl-pyridine-2-carboxylate

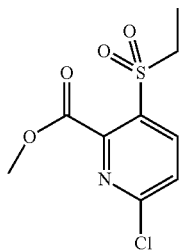 [SMILES: CCS(=O)(=O)c1ccc(Cl)nc1C(=O)OC]

In a three neck flask under argon, methyl 6-chloro-3-ethylsulfanyl-pyridine-2-carboxylate: (4 g, 17.264 mmol) was dissolved in dichloromethane (80 mL), and cooled to 0° C. This solution was then treated, portion wise, with meta-chloroperoxybenzoic acid (8.9374 g, 36.254 mmol) keeping the temperature at 0° C. After completion of the addition the mixture was allowed to warm to ambient temperature and stirred for 15 hours. LC-MS analysis after this time showed reaction completion. The reaction mixture was quenched with NaOH 1 M (50 ml) and sodium thiosulfate sol (20 ml). The aqueous layer was extracted 3 times with dichloromethane. The combined organic layers were washed with aq NaOH 1M (×2), brine, dried over $Na_2SO_4$, filtered and concentrated in vacuo to give the title compound as a colourless oil. LCMS (method 1): 264 (M+H)+; retention time: 0.79 min. $^1$H NMR (400 MHz, $CDCl_3$) δ ppm 1.39 (t, 3H) 2.92 (m, 2H) 4.00 (s, 3H) 7.40 (d, 1H) 7.65 (d, 1H)

Step C: Preparation of Methyl 6-(cyclopropylamino)-3-ethylsulfonyl-pyridine-2-carboxylate

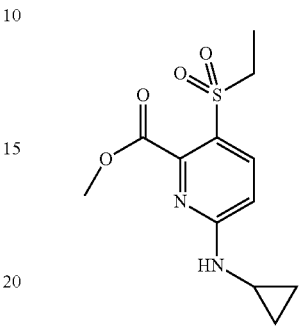

A solution of methyl 6-chloro-3-ethylsulfonyl-pyridine-2-carboxylate (1 g, 3.7922 mmol) in NMP (25 mL) at ambient temperature was treated with cyclopropylamine (0.26513 g, 0.322 mL, 4.5506 mmol) and the resulting mixture stirred for two days at this temp. The reaction mixture was quenched with $NH_4Cl$ sat. solution then the aqueous layer was extracted 3 times with EtOAc. The combined organic layers were washed 3 times with water, dried over $Na_2SO_4$, filtered and concentrated in vacuo The crude product so obtained was purified by combi flash chromatography with a column of 12 g and a gradient cyclohexane+0-80% EtOAc. This gave the title compound as a colourless oil. LCMS (method 1): 285 (M+H)+; retention time: 1.00 min. $^1$H NMR (400 MHz, $CDCl_3$) δ ppm 0.54-0.67 (m, 2H) 0.81-0.98 (m, 2H) 1.33 (t, 3H) 2.51-2.65 (m, 1H) 3.40 (q, 2H) 3.98 (s, 3H) 5.70 (br. s., 1H) 6.88 (d, 1H) 8.03 (d, 1H)

Step D: Preparation of 5-(cyclopropylamino)-3-ethylsulfonyl-pyridine-2-carbohydrazide

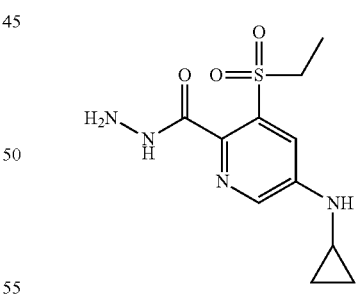

A solution of methyl 6-(cyclopropylamino)-3-ethylsulfonyl-pyridine-2-carboxylate (0.8 g, 2.814 mmol) was dissolved in tetrahydrofuran (16 mL) and hydrazine monohydrate (8.24 g, 8 mL, 163 mmol) was added at ambient temperature. After 5 hrs, the desired mass of the product could be seen, and to prevent further unselective reactions, the reaction was terminated. The reaction mixture was quenched with 20 ml of water (temperature up to 30° C.), and the aqueous layer was extracted 3 times with EtOAc. The combined organic layers were washed with brine, dried over $Na_2SO_4$, filtered and concentrated in vacuo. The crude product was purified by combi flash chromatography with a column of 12 g and a gradient dichloromethane+0-15% methanol, to give the title compound as a white solid, Mp. 75-78° C.

Step E: Preparation of Preparation of N-cyclopropyl-5-ethylsulfonyl-6-[4-methyl-5-[4-(trifluoromethyl)-2-pyridyl]-1,2,4-triazol-3-yl]pyridin-2-amine A5

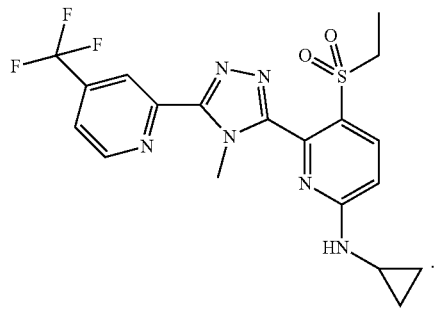

(A5)

A solution of ethyl N-methyl-4-(trifluoromethyl)pyridine-2-carboximidothioate (0.2183 g, 0.88 mmol, prepared as described in Step C example P2) in pyridine (3.75 mL) was purged with argon for 10 min. Then 5-(cyclopropylamino)-3-ethylsulfonyl-pyridine-2-carbohydrazide (0.25 g, 0.8794 mmol) was added, and the pale yellow suspension was heated in the microwave at 80° C. for 40 min. LCMS: showed the desired product was present. The reaction mixture was poured into ice-water and the aqueous layer extracted with dichloromethane (×3). The combined organic layer was washed with water, dried over Na$_2$SO$_4$, filtered and concentrated in vacuo. The crude product was purified by combi flash chromatography with a column of 12 g and a gradient cyclohexane+0-100% EtOAc, to give the title compound as a yellow oil. $^1$H NMR (400 MHz, CDCl$_3$) δ ppm 0.59-0.69 (m, 2H) 0.90-0.98 (m, 2H) 1.32 (t, 3H) 2.55-2.73 (m, 1H) 3.58 (q, 2H) 4.01 (s, 3H) 5.71 (br. s., 1H) 6.95 (d, 1H) 7.51-7.61 (m, 1H) 8.19 (d, 1H) 8.68 (s, 1H) 8.84 (d, 1H).

Example P5: Synthesis of N-[5-ethylsulfonyl-6-[4-methyl-5-[4-(trifluoromethyl)-2-pyridyl]-1,2,4-triazol-3-yl]-2-pyridyl]cyclopropanecarboxamide A6

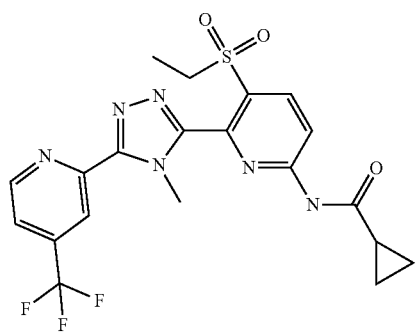

A6

Step A: Preparation of 6-chloro-3-ethylsulfanyl-2-[4-methyl-5-[4-(trifluoromethyl)-2-pyridyl]-1,2,4-triazol-3-yl]pyridine

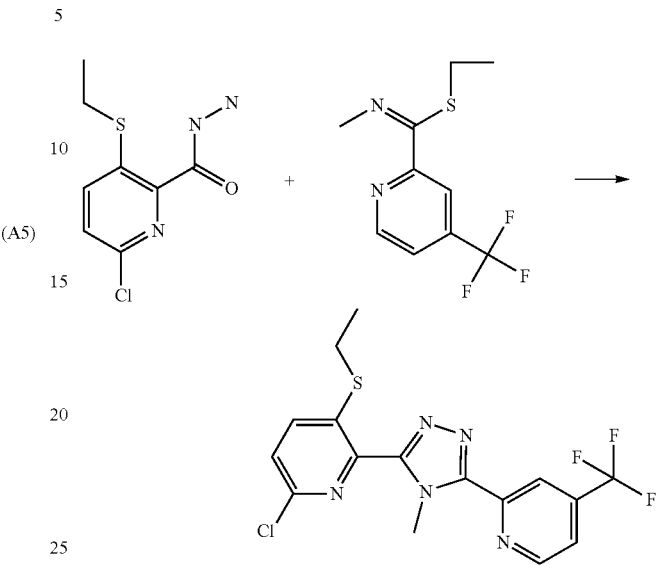

In a microwave vial 6-chloro-3-ethylsulfanyl-pyridine-2-carbohydrazide (150 mg, 0.64739 mmol) was taken and a solution of ethyl (2E)-N-methyl-4-(trifluoromethyl)pyridine-2-carboximidothioate (180 mg, 0.64739 mmol) in pyridine (0.7 ml) was added. The reaction mixture was purged with azote for 5 min was heated in a microwave at 180° C. for 50 min. Reaction mixture turns to black and was poured into ice-water—stirred for 20 min The product was not solidified therefore ethyl acetate was added and extracted in ethyl acetate. Aqueous layer was extracted two times with Ethyl acetate, combined black organic layer was evaporated and crude was purified by CombiFlash column chromatography gradient cyclohexane+0-30% EtOAc to give (135 mg, 52%) as yellow gummy mass.

LCMS (method 1): 399 (M+H)+; retention time: 1.54 min. $^1$H NMR (400 MHz, CDCl$_3$) δ 8.86 (d, 1H), 8.70-8.62 (m, 1H), 7.78-7.70 (m, 1H), 7.59-7.53 (m, 1H), 7.42-7.35 (m, 1H), 4.19-4.12 (m, 3H), 2.99-2.89 (m, 2H), 1.30 (t, 3H).

Step B: Preparation of 6-chloro-3-ethylsulfonyl-2-[4-methyl-5-[4-(trifluoromethyl)-2-pyridyl]-1,2,4-triazol-3-yl]pyridine

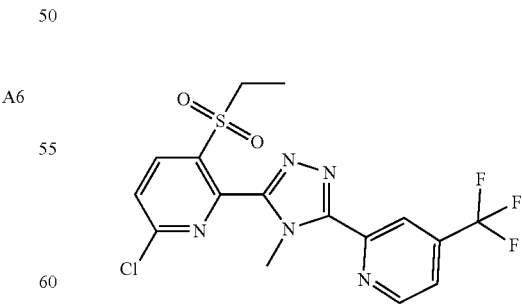

To a solution of 6-chloro-3-ethylsulfanyl-2-[4-methyl-5-[4-(trifluoromethyl)-2-pyridyl]-1,2,4-triazol-3-yl]pyridine (120 mg, 0.3002 mmol) in dichloromethane (2 mL, 31.1 mmol) was added 3-chlorobenzenecarboperoxoic acid (145 mg, 0.6303 mmol). The resulting solution was stirred for 1.5 h at room temperature. After complete conversion, reaction mixture was quenched by aqueous solution of sodium thiosulfate, extraction was done in dichloromethane two times and organic phase was washed with NaHCO₃ aqueous solution two times. It was dried over Na₂SO₄ and concentrated under vacuum to give crude as yellow solid. Crude was purified by column chromatography gradient cyclohexane+0-30% EtOAc to give (109 mg, 84%) solid product. ¹H NMR (400 MHz, CDCl₃) δ ppm 1.37 (t, 3H) 3.77-3.87 (m, 2H) 4.10 (s, 3H) 7.60 (dd, 1H) 7.71 (d, 1H) 8.47 (d, 1H) 8.69 (s, 1H) 8.88 (d, 1H).

Step C: Preparation of tert-butyl N-[5-ethylsulfonyl-6-[4-methyl-5-[4-(trifluoromethyl)-2-pyridyl]-1,2,4-triazol-3-yl]-2-pyridyl]carbamate A37

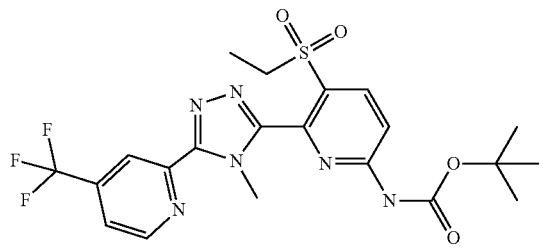 [SMILES: CCS(=O)(=O)c1ccc(NC(=O)OC(C)(C)C)nc1-c1nnc(-c2cc(C(F)(F)F)ccn2)n1C]

6-chloro-3-ethylsulfonyl-2-[4-methyl-5-[4-(trifluoromethyl)-2-pyridyl]-1,2,4-triazol-3-yl]pyridine (80 mg, 0.185 mmol) was dissolved in anhydrous 1,4-dioxane (1 mL) and to it cesium carbonate (85 mg, 0.259 mmol) was added under nitrogen followed by the addition of palladium (II) acetate (2 mg, 0.0056 mmol) and tert-butyl carbamate (27 mg, 0.22 mmol). Reaction mixture was degassed with nitrogen for 15 min then X-PHOS (9 mg. 0.017 mmol) was added and the reaction mixture was heated at 110° C. in a preheated oil bath for 14 hours. The reaction mixture was quenched with 10 ml of water and 15 ml of ethyl acetate, aqueous layer was extracted with 15 ml of ethyl acetate and combined organic layer evaporated and directly subjected to column purification gradient cyclohexane+0-50% EtOAc to give tert-butyl N-[5-ethylsulfonyl-6-[4-methyl-5-[4-(trifluoromethyl)-2-pyridyl]-1,2,4-triazol-3-yl]-2-pyridyl]carbamate (45 mg, 47.4%). ¹H NMR (400 MHz, CDCl₃) δ ppm 1.33 (t, 3H) 1.56 (s, 9H) 3.65 (m, 2H) 4.00 (s, 3H) 7.58 (d, 2H) 8.28-8.33 (m, 1H) 8.38-8.44 (m, 1H) 8.69 (s, 1H) 8.86 (d, 1H) 8.83-8.89 (m, 1H)

Step D: Preparation of 5-ethylsulfonyl-6-[4-methyl-5-[4-(trifluoromethyl)-2-pyridy]-1,2,4-triazol-3-yl]pyridin-2-amine A36

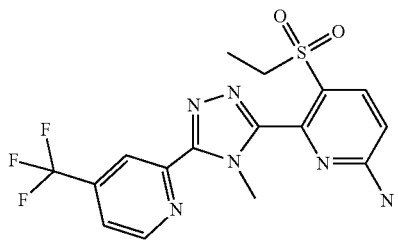 [SMILES: CCS(=O)(=O)c1ccc(N)nc1-c1nnc(-c2cc(C(F)(F)F)ccn2)n1C]

The hydrochloric acid solution (10 mL, 4 M in Dioxane) was added to a solution of tert-butyl N-[5-ethylsulfonyl-6-[4-methyl-5-[4-(trifluoromethyl)-2-pyridyl]-1,2,4-triazol-3-yl]-2-pyridyl]carbamate A37 (2 g, 3.902 mmol) in 1,4-dioxane (10 ml) and the pale yellow solution was then heated at 50° C. for 6 hours. Reaction went to completion and was cooled to 0° C. and quenched with an aq solution of saturated NaHCO₃ solution till basic, diluted with 30 ml water and extracted with ethyl acetate, dried over sodium sulfate, filtered and concentrated under vacuum. The residue was purified by column chromatography gradient cyclohexane+0-80% EtOAc to give 5-ethylsulfonyl-6-[4-methyl-5-[4-(trifluoromethyl)-2-pyridyl]-1,2,4-triazol-3-yl]pyridin-2-amine (850 mg, 53%). Mp=123-125° C. ¹H NMR (400 MHz, CDCl₃) δ ppm 1.32 (t, 3H) 3.57 (m, 2H) 4.02 (s, 3H) 5.18-5.38 (m, 2H) 6.71 (d, 1H) 7.58 (d, 1H) 8.12 (d, 1H) 8.68 (s, 1H) 8.85 (d, 1H).

Step E: Synthesis of N-[5-ethylsulfonyl-6-[4-methyl-5-[4-(trifluoromethyl)-2-pyridyl]-1,2,4-triazol-3-yl]-2-pyridyl]cyclopropanecarboxamide A6

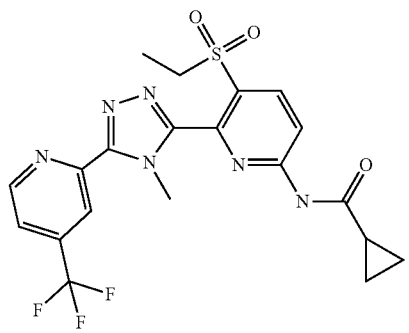

A6

5-ethylsulfonyl-6-[4-methyl-5-[4-(trifluoromethyl)-2-pyridyl]-1,2,4-triazol-3-yl]pyridin-2-amine A36 (0.4 g, 0.97 mmol) dissolved in dichloromethane (5 mL) was added N,N-diethylethanamine (0.295 g, 2.91 mmol) at 0° C. Reaction mixture was stirred for 5 min followed by addition of cyclopropane carbonyl chloride (0.122 g, 1.16 mmol) at 0° C. Reaction mixture was then warmed to room temperature and left stirring for additional 24 h. The reaction was quenched with 10 mL water and extracted with 15 mL dichloromethane. The organic phase was washed with brine, dried over sodium sulfate and concentrated under vacuum. The crude was purified by reverse phase preparative HPLC to give N-[5-ethylsulfonyl-6-[4-methyl-5-[4-(trifluoromethyl)-2-pyridyl]-1,2,4-triazol-3-yl]-2-pyridyl]cyclopropanecarboxamide (78 mg, 17%). Mp 249-251° C. ¹H NMR (400 MHz, CDCl₃) δ ppm 0.99 (m, 2H) 1.18 (m, 2H) 1.31 (t, 3H) 1.74 (m, 1H) 3.61 (m, 2H) 3.94 (s, 3H) 7.60 (d, 1H) 8.40 (d, 1H) 8.53 (d, 1H) 8.66 (s, 1H) 8.86 (d, 1H) 8.92 (s, 1H).

Example P6: Preparation of N-[5-ethylsulfonyl-6-[4-methyl-5-[4-(trifluoromethyl)-2-pyridyl]-1,2,4-triazol-3-yl]-3-pyridyl]-N-methyl-cyclopropanecarboxamide A7

Step A: 5-bromo-3-ethylsulfanyl-2-[4-methyl-5-[4-(trifluoromethyl)-2-pyridyl]-1,2,4-triazol-3-yl]pyridine

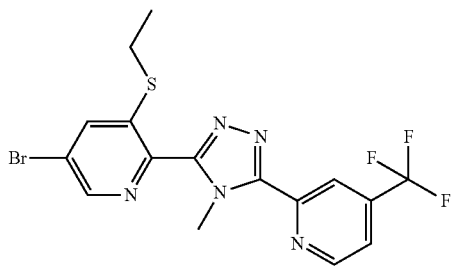 [SMILES: CCSc1cc(Br)cnc1-c1nnc(-c2cc(C(F)(F)F)ccn2)n1C]

In a microwave vial, ethyl (2E)-N-methyl-4-(trifluoromethyl)pyridine-2-carboximidothioate (1 g, 3.63 mmol) was dissolved in pyridine (4 mL). The resultant clear yellow solution was purged with argon for 10 min and is followed by addition of 5-bromo-3-ethylsulfanyl-pyridine-2-carbohydrazide (1 g, 3.6251 mmol). The reaction mixture was heated in a microwave at 180° C. for 50 min and the dark yellow solution was poured onto 10 ml ice-water and stirred for 10 min. The pale brown suspension was filtered washed with cold water, dissolved in dichloromethane, dried over sodium sulfate and reduced under vacuum to dryness. The crude yellow solid was stirred in cold diisopropyl ether, filtered, washed with cold diisopropylether, and dried in vacuum to give 5-bromo-3-ethylsulfanyl-2-[4-methyl-5-[4-(trifluoromethyl)-2-pyridyl]-1,2,4-triazol-3-yl]pyridine (0.99 g, 61%) as a yellow solid product.
$^1$H NMR (400 MHz, CDCl$_3$) δ ppm 1.31-1.40 (m, 3H) 2.97 (m, 2H) 4.14 (s, 3H) 7.58 (d, 1H) 7.87 (d, 1H) 8.55 (d, 1H) 8.70 (s, 1H) 8.86 (d, 1H).

Step B: Preparation of 5-bromo-3-ethylsulfonyl-2-[4-methyl-5-[4-(trifluoromethyl)-2-pyridyl]-1,2,4-triazol-3-yl]pyridine

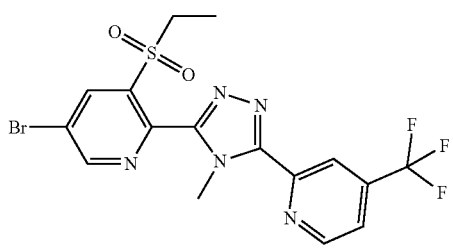 [SMILES: CCS(=O)(=O)c1cc(Br)cnc1-c1nnc(-c2cc(C(F)(F)F)ccn2)n1C]

To a solution of 5-bromo-3-ethylsulfanyl-2-[4-methyl-5-[4-(trifluoromethyl)-2-pyridyl]-1,2,4-triazol-3-yl]pyridine (3 g, 6.752 mmol) in dichloromethane (92.75 g, 1090 mmol) was added 3-chlorobenzenecarboperoxoic acid (3.185 g, 13.84 mmol). The resulting solution was stirred for an overnight at room temperature. Reaction went to completion and was quenched by aqueous solution of sodium thiosulfate. Extraction was done in DCM two times. Organic phase was washed with NaHCO$_3$ aqueous solution two times, was dried over Na$_2$SO$_4$ and concentrated under vacuum to give crude as yellow solid. Crude product was purified by column purification to give 5-bromo-3-ethylsulfonyl-2-[4-methyl-5-[4-(trifluoromethyl)-2-pyridyl]-1,2,4-triazol-3-yl]pyridine (2.3 g, 72%). $^1$H NMR (400 MHz, CDCl$_3$) δ ppm 1.34-1.44 (m, 3H) 3.85 (m, 2H) 4.07 (s, 3H) 7.60 (d, 1H) 8.63-8.72 (m, 2H) 8.87 (d, 1H) 9.06 (d, 1H).

Step C: Preparation of tert-butyl N-[5-ethylsulfonyl-6-[4-methyl-5-[4-(trifluoromethyl)-2-pyridyl]-1,2,4-triazol-3-yl]-3-pyridyl]carbamate A40

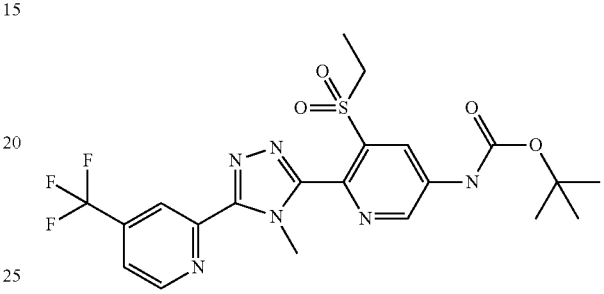

5-bromo-3-ethylsulfonyl-2-[4-methyl-5-[4-(trifluoromethyl)-2-pyridyl]-1,2,4-triazol-3-yl]pyridine (0.1 g, 0.2100 mmol) was dissolved in anhydrous 1,4-dioxane (1 mL) and to it cesium carbonate (0.096 g, 0.2939 mmol) was added under nitrogen followed by the addition of palladium (II) acetate (0.0014 g, 0.0063 mmol) and tert-butyl carbamate (0.0295 g, 0.252 mmol). Reaction mixture was degassed with nitrogen for 15 mins. X-PHOS (0.0092 g, 0.019 mmol) was added and the reaction mixture was heated at 110° C. in a preheated oil bath for 14 hours. The mixture was filtered through celite bed and the bed was washed with EtOAc (20 ml). Organic layer was evaporated and directly subjected to column chromatography gradient cyclohexane+0-60% EtOAc to give tert-butyl N-[5-ethylsulfonyl-6-[4-methyl-5-[4-(trifluoromethyl)-2-pyridyl]-1,2,4-triazol-3-yl]-3-pyridyl]carbamate (0.078 g, 72%). $^1$H NMR (400 MHz, CDCl$_3$) δ ppm 1.37 (t, 3H) 1.57 (s, 9H) 3.78 (q, 2H) 4.02 (s, 3H) 7.14 (s, 1H) 7.58 (d, 1H) 8.59 (d, 1H) 8.69 (s, 1H) 8.86 (d, 1H) 9.04 (d, 1H).

Step D: Preparation of Tert-Butyl N-[5-ethylsulfonyl-6-[4-methyl-5-[4-(trifluoromethyl)-2-pyridyl]-1,2,4-triazol-3-yl]-3-pyridyl]-N-methyl-carbamate A39

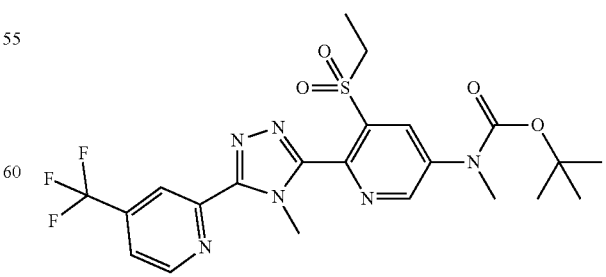

To a 0° C. cooled solution of sodium hydride (350 mg, 8.8 mmol) in THF (10 ml) was added a solution of tert-butyl N-[5-ethylsulfonyl-6-[4-methyl-5-[4-(trifluoromethyl)-2-pyridyl]-1,2,4-triazol-3-yl]-3-pyridyl]carbamate (3.0 g, 5.9 mmol) in THF (20 ml). Reaction was stirred for 30 mins. To this was then added iodomethane (1.1 ml, 18 mmol). The reaction was allowed to warm to room temperature over 2-3 hours, monitored by TLC. The reaction was neutralized using 1N HCl solution (10 ml). Aqueous layer was extracted with ethyl acetate and combined organic layer was dried over sodium sulfate, concentrated under reduced pressure. The crude product was purified by column chromatography gradient cyclohexane+0-20% EtOAc to give tert-butyl N-[5-ethylsulfonyl-6-[4-methyl-5-[4-(trifluoromethyl)-2-pyridyl]-1,2,4-triazol-3-yl]-3-pyridyl]-N-methyl-carbamate (1.5 g, 49%). H NMR (400 MHz, CDCl$_3$) δ 9.01 (d, 1H), 8.87 (d, 1H), 8.70 (s, 1H), 8.43 (d, 1H), 7.59 (m, 1H), 4.10-4.02 (m, 3H), 3.90-3.71 (m, 2H), 3.45 (s, 3H), 1.59-1.54 (m, 9H), 1.45-1.35 (m, 3H).

Step E: Preparation of 5-ethylsulfonyl-N-methyl-6-[4-methyl-5-[4-(trifluoromethyl)-2-pyridyl]-1,2,4-triazol-3-yl]pyridin-3-amine

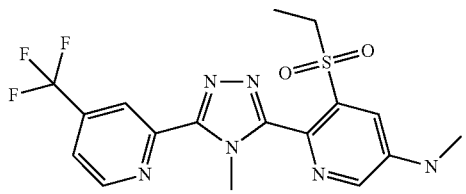 [SMILES: CCS(=O)(=O)c1cc(NC)cnc1-c1nnc(-c2cc(C(F)(F)F)ccn2)n1C]

To a solution of tert-butyl N-[5-ethylsulfonyl-6-[4-methyl-5-[4-(trifluoromethyl)-2-pyridyl]-1,2,4-triazol-3-yl]-3-pyridyl]-N-methyl-carbamate (1.5 g, 2.8 mmol) in 1,4-dioxane (15 mL) was added hydrogen chloride in dioxane (15 mL, 4 mol/L). The reaction was stirred at 50° C. for 8 hours and then neutralized with saturated sodium bicarbonate solution (10 ml). Aqueous layer was extracted with ethyl acetate. Organic layer was dried over sodium sulfate, filtered and concentrated under reduced pressure to give 5-ethylsulfonyl-N-methyl-6-[4-methyl-5-[4-(trifluoromethyl)-2-pyridyl]-1,2,4-triazol-3-yl]pyridin-3-amine (1.1 g, 91%). $^1$H NMR (400 MHz, CDCl$_3$) δ 8.84 (d, 1H), 8.66 (s, 1H), 8.29 (d, 1H), 7.56 (m, 1H), 7.50 (d, 1H), 3.97 (s, 3H), 3.73-3.66 (m, 3H), 3.02-2.91 (m, 3H), 1.38-1.28 (m, 3H).

Step F: N-[5-ethylsulfonyl-6-[4-methyl-5-[4-(trifluoromethyl)-2-pyridyl]-1,2,4-triazol-3-yl]-3-pyridyl]-N-methyl-cyclopropanecarboxamide A7

A7

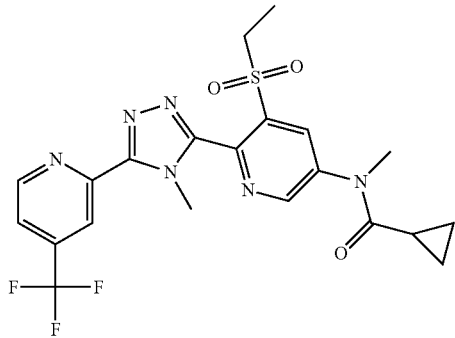

To a 0° C. cooled solution of 5-ethylsulfonyl-N-methyl-6-[4-methyl-5-[4-(trifluoromethyl)-2-pyridyl]-1,2,4-triazol-3-yl]pyridin-3-amine (300 mg, 0.7036 mmol) and N,N-diethylethanamine (0.20 ml, 1.407 mmol) in dichloromethane (3 mL) was slowly added cyclopropane carbonyl chloride (0.095 ml, 1.05 mmol). The reaction was slowly allowed to warm to room temperature and stirred for 1 hour.

Reaction mass quenched with water (10 ml) and extracted with ethyl acetate. The combined organic layers were washed successively with water and brine, dried over Na$_2$SO$_4$ and concentrated in vacuo. The crude product was purified by column chromatography gradient cyclohexane+0-30% EtOAc to give N-[5-ethylsulfonyl-6-[4-methyl-5-[4-(trifluoromethyl)-2-pyridyl]-1,2,4-triazol-3-yl]-3-pyridyl]-N-methyl-cyclopropanecarboxamide (250 mg, 71%). $^1$H NMR (400 MHz, CDCl$_3$) δ 9.00 (d, 1H), 8.88 (d, 1H), 8.71 (s, 1H), 8.45 (d, 1H), 7.61 (m, 1H), 4.10 (s, 3H), 3.86 (q, 2H), 3.54 (s, 3H), 1.58 (br. s., 1H), 1.40 (t, 3H), 1.23-1.16 (m, 2H), 0.95-0.85 (m, 2H).

Example P6b: N-[5-ethylsulfonyl-6-[4-methyl-5-[4-(trifluoromethyl)-2-pyridyl]-1,2,4-triazol-3-yl]-2-pyridyl]-N-methyl-cyclopropanecarboxamide A8

A8

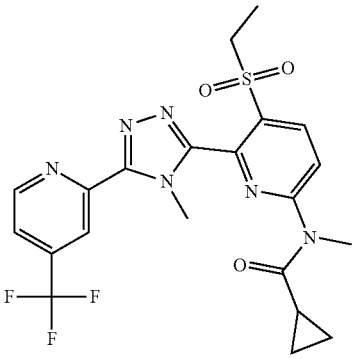

Step A: Tert-Butyl N-[5-ethylsulfonyl-6-[4-methyl-5-[4-(trifluoromethyl)-2-pyridyl]-1,2,4-triazol-3-yl]-2-pyridyl]-N-methyl-carbamate A38

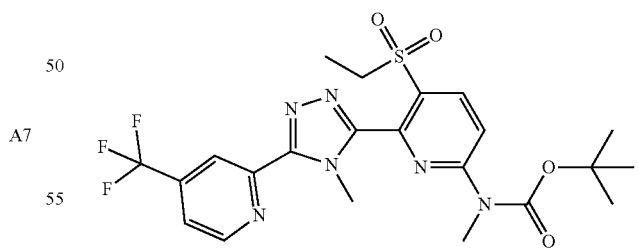

In a 25 ml round flask, to a 0° C. cooled solution of sodium hydride (93.6 mg 2.341 mmol) in tetrahydrofuran (2 mL) was added dropwise a clear solution of tert-butyl N-[5-ethylsulfonyl-6-[4-methyl-5-[4-(trifluoromethyl)-2-pyridyl]-1,2,4-triazol-3-yl]-2-pyridyl]carbamate A37 (800 mg, 1.561 mmol) in tetrahydrofuran (6 ml). To this N,N-dimethylformamide (1.5 mL) was added and reaction was stirred at 0° C. for 30 mins. Iodomethane (664 mg, 4.683 mmol) was then added and reaction was allowed to warm to room temperature over 3 hours. Reaction went to completion and was neutralized with 2N HCl (till just acidic), diluted with 10 ml of water extracted with ethyl acetate. Combined organic layer was dried over sodium sulfate, filtered and concentrated under reduced pressure. The crude product was purified by CombiFlash column chromatography gradient cyclohexane+0-30% EtOAc to give tert-butyl N-[5-ethylsulfonyl-6-[4-methyl-5-[4-(trifluoromethyl)-2-pyridyl]-1,2,4-triazol-3-yl]-2-pyridyl]-N-methyl-carbamate (750 mg, 91%). Mp=179-181° C. $^1$H NMR (400 MHz, CDCl$_3$) δ ppm 1.35 (t, 3H) 3.47 (s, 3H) 3.71 (q, 2H) 4.05 (s, 3H) 7.59 (dd, 1H) 8.34 (s, 2H) 8.68-8.73 (m, 1H) 8.87 (d, 1H).

Step C: 5-ethylsulfonyl-N-methyl-6-[4-methyl-5-[4-(trifluoromethyl)-2-pyridyl]-1,2,4-triazol-3-yl]pyridin-2-amine A41

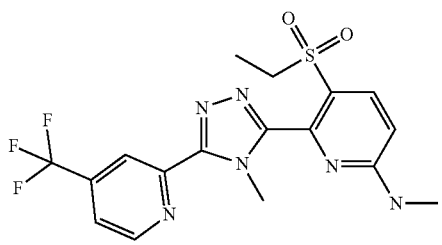 [SMILES: CCS(=O)(=O)c1ccc(NC)nc1-c1nnc(-c2cc(C(F)(F)F)ccn2)n1C]

The hydrochloric acid (4M in Dioxane) (6.5 mL) was added to a solution of tert-butyl N-[5-ethylsulfonyl-6-[4-methyl-5-[4-(trifluoromethyl)-2-pyridyl]-1,2,4-triazol-3-yl]-2-pyridyl]-N-methyl-carbamate A38 (650 mg, 1.235 mmol) in 1,4-dioxane (7 ml) and the colourless clear solution was then heated at 50° C. for 9 hour. A saturated aq solution of NaHCO$_3$ was added dropwise in the reaction at 0° C. and the aqueous phase was extracted with 15 ml ethyl acetate (3×). Combined organic layer was evaporated under vacuum and the solid was dried to give 5-ethylsulfonyl-N-methyl-6-[4-methyl-5-[4-(trifluoromethyl)-2-pyridyl]-1,2,4-triazol-3-yl]pyridin-2-amine (500 mg, 95%). Mp=209-211° C. $^1$H NMR (400 MHz, CDCl$_3$) δ ppm 1.31 (t, 3H) 3.01 (d, 3H) 3.59 (q, 2H) 4.03 (s, 3H) 5.47 (br. s., 1H) 6.58 (d, 1H) 7.57 (m, 1H) 8.07 (d, 1H) 8.68 (s, 1H) 8.85 (d, 1H).

Step D: N-[5-ethylsulfonyl-6-[4-methyl-5-[4-(trifluoromethyl)-2-pyridyl]-1,2,4-triazol-3-yl]-2-pyridyl]-N-methyl-cyclopropanecarboxamide A8

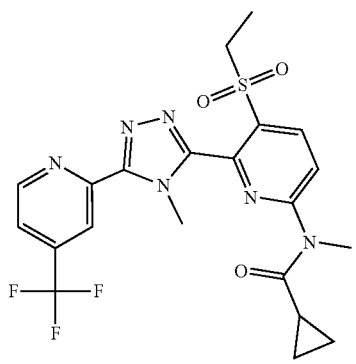

In a one neck flask, 5-ethylsulfonyl-N-methyl-6-[4-methyl-5-[4-(trifluoromethyl)-2-pyridyl]-1,2,4-triazol-3-yl]pyridin-2-amine (0.435 g, 1.02 mmol) dissolved in dichloromethane (5 mL) was added N,N-diethylethanamine (0.2065 g, 2.04 mmol). The reaction mixture was stirred for 5 min and cyclopropane carbonyl chloride (0.16 g, 1.53 mmol) was added dropwise under ice bath. N,N-dimethylformamide (1 ml) was added to the reaction mixture and stirred for 5 hours at room temperature, then heated at 50° C. under water condenser for 24 hours. The reaction mixture was quenched with 15 ml of water, extracted with 20 ml of dichloromethane, organic layer washed with brine, concentrated under reduced pressure to provide crude product. The crude product was purified by CombiFlash column chromatography gradient cyclohexane+0-50% EtOAc to give N-[5-ethylsulfonyl-6-[4-methyl-5-[4-(trifluoromethyl)-2-pyridyl]-1,2,4-triazol-3-yl]-2-pyridyl]-N-methyl-cyclopropanecarboxamide (126 mg, 25%). Mp=75-77° C. $^1$H NMR (400 MHz, CDCl$_3$) δ ppm 0.99 (m, 2H) 1.22 (m, 2H) 1.36 (t, 3H) 1.94-2.02 (m, 1H) 3.67 (s, 3H) 3.73 (m, 2H) 4.07 (s, 3H) 7.60 (d, 1H) 8.12 (d, 1H) 8.40 (d, 1H) 8.71 (s, 1H) 8.87 (d, 1H).

Example P7: Preparation of N-cyclopropyl-5-ethylsulfonyl-6-[4-methyl-5-[4-(trifluoromethyl)-2-pyridyl]-1,2,4-triazol-3-yl]pyridin-3-amine A9

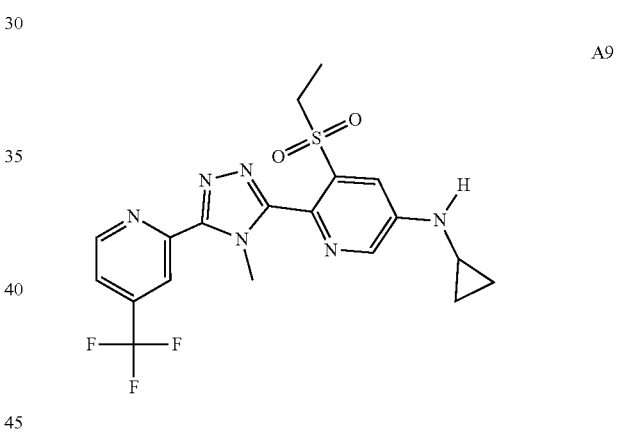

5-bromo-3-ethylsulfonyl-2-[4-methyl-5-[4-(trifluoromethyl)-2-pyridyl]-1,2,4-triazol-3-yl]pyridine (Prepared as descripted in Example P6 Step A and Step B) (0.5 g, 1.050 mmol) was dissolved in anhydrous toluene (5 mL) and to it cesium carbonate (0.514 g, 1.575 mmol) was added under nitrogen. Reaction mixture was degassed with nitrogen for 15 mins, Tris(dibenzylideneacetone)dipalladium (0) (0.01942 g, 0.021 mmol), (+/−)-BINAP (26.96 mg, 0.04199 mmol) and cyclopropylamine (0.07192 g, 1.260 mmol) was added and the reaction mixture heated at 110° C. for 16 hours. Solution became dark brown and reaction mixture was filtered through celite bed and washed with ethyl acetate (20 ml). Organic layer was evaporated and directly subjected to column chromatography gradient cyclohexane+0-40% EtOAc to give N-cyclopropyl-5-ethylsulfonyl-6-[4-methyl-5-[4-(trifluoromethyl)-2-pyridyl]-1,2,4-triazol-3-yl]pyridin-3-amine (0.25 g, 52%). Mp: 134-136° C. $^1$H NMR (400 MHz, CDCl$_3$) δ ppm 0.61-0.68 (m, 2H) 0.90-0.99 (m, 2H) 1.35 (t, 3H) 2.61 (m, 1H) 3.73 (q, 2H) 4.00 (s, 3H) 4.89 (br. s., 1H) 7.56 (d, 1H) 7.76 (d, 1H) 8.43 (d, 1H) 8.69 (s, 1H) 8.85 (d, 1H).

Example P8: Preparation of N-cyclopropyl-5-ethyl-sulfonyl-N-methyl-6-[4-methyl-5-[4-(trifluoromethyl)-2-pyridyl]-1,2,4-triazol-3-yl]pyridin-3-amine A10

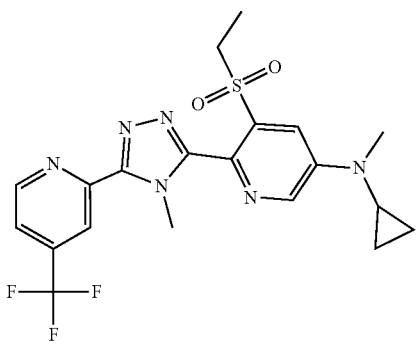

N-cyclopropyl-5-ethylsulfonyl-6-[4-methyl-5-[4-(trifluoromethyl)-2-pyridyl]-1,2,4-triazol-3-yl]pyridin-3-amine (A9) (0.05 g, 0.1105 mmol) was dissolved in dry N,N-dimethylformamide (0.5 mL) and to it sodium hydride (0.005747 mg, 0.1437 mmol) was added under nitrogen at 0° C. Reaction mixture was stirred at 0° C. for 10 mins followed by addition of iodomethane (0.01726 g, 0.1216 mmol). The reaction mixture was left stirring for 2 hours at room temperature and then quenched by addition of water and then diluted with ethyl acetate (10 ml). Organic layer was separated and aqueous layer was further extracted with ethyl acetate (2×10 ml). Combined organic layers were washed with brine, dried over sodium sulfate and concentrated under vacuum to get crude product. Column chromatography gradient cyclohexane+0-30% EtOAc gave N-cyclopropyl-5-ethylsulfonyl-N-methyl-6-[4-methyl-5-[4-(trifluoromethyl)-2-pyridyl]-1,2,4-triazol-3-yl]pyridin-3-amine (0.033 g, 64%). $^1$H NMR (400 MHz, CDCl$_3$) δ ppm 0.72-0.79 (m, 2H) 1.01-1.09 (m, 2H) 1.36 (t, 3H) 2.70 (m, 1H) 3.17 (s, 3H), 3.74 (q, 2H) 4.00 (s, 3H) 7.56 (d, 1H) 7.84 (d, 1H) 8.63 (d, 1H) 8.70 (s, 1H) 8.85 (d, 1H).

Example P9: Preparation of N-cyclopropyl-5-ethyl-sulfonyl-N-methyl-6-[4-methyl-5-[4-(trifluoromethyl)-2-pyridyl]-1,2,4-triazol-3-yl]pyridin-2-amine (A11)

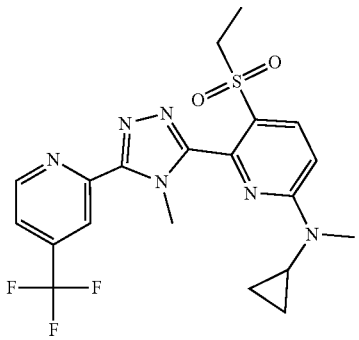

6-Chloro-3-ethylsulfonyl-2-[4-methyl-5-[4-(trifluoromethyl)-2-pyridyl]-1,2,4-triazol-3-yl]pyridine (as described in Example P5 Step A and Step B) (450 mg, 1.042 mmol), N-methylcyclopropyl amine (296 mg, 4.169 mmol) and N,N-dimethylformamide (7 mL, 90.1 mmol) were charged in a microwave vial. The reaction mixture was stirred under microwave irradiation at 100° C. for 4 hours. Completion of the reaction was monitored by TLC, and reaction mixture was diluted with ethyl acetate (20 ml) and water, organic layer was separated, dried with sodium sulfate and evaporated off under reduced pressure. Compound was purified by column chromatography gradient cyclohexane+0-100% EtOAc to give N-cyclopropyl-5-ethylsulfonyl-N-methyl-6-[4-methyl-5-[4-(trifluoromethyl)-2-pyridyl]-1,2,4-triazol-3-yl]pyridin-2-amine (0.16 mg, 32%) as a white solid. Mp: 180-182° C. $^1$H NMR (400 MHz, CDCl$_3$) δ ppm 0.61-0.82 (m, 2H) 0.94-1.07 (m, 2H) 1.33 (t, 3H) 1.43 (s, 2H) 2.62-2.79 (m, 1H) 3.10-3.29 (m, 3H) 3.63 (q, 2H) 4.05 (s, 3H) 7.15 (d, 1H) 7.57 (d, 1H) 8.02-8.23 (m, 1H) 8.71 (s, 1H) 8.85 (d, 1H).

Example P10: Preparation of N-[5-ethylsulfonyl-6-[4-methyl-5-[4-(trifluoromethyl)-2-pyridyl]-1,2,4-triazol-3-yl]-3-pyridyl]-N-methyl-methanesulfonamide A12

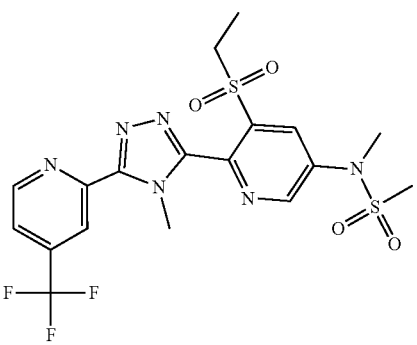

Step A: Preparation of N-[5-ethylsulfonyl-6-[4-methyl-5-[4-(trifluoromethyl)-2-pyridyl]-1,2,4-triazol-3-yl]-3-pyridyl]-N-methylsulfonyl-methanesulfonamide

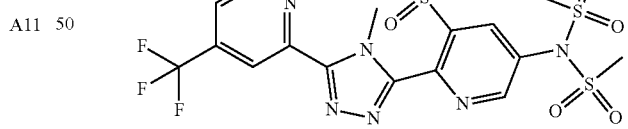

To a dichloromethane (15 mL) solution of 5-ethylsulfonyl-6-[4-methyl-5-[4-(trifluoromethyl)-2-pyridyl]-1,2,4-triazol-3-yl]pyridin-3-amine (A35) (1 g, 2.425 mmol) was added triethylamine (0.7 ml, 4.850 mmol) followed by methane sulfonyl chloride (0.5 ml, 4.850 mmol) and the reaction was stirred at room temperature for 1 hour. Reaction was quenched by addition of aq sodium bicarbonate solution and dichloromethane, organic layer was separated, concentrated to get crude product which was purified by column chromatography gradient cyclohexane+0-70% EtOAc to give N-[5-ethylsulfonyl-6-[4-methyl-5-[4-(trifluoromethyl)-2-pyridyl]-1,2,4-triazol-3-yl]-3-pyridyl]-N-methylsulfonylmethanesulfonamide (450 mg, 32%). Mp: 253-255° C. LCMS (method 1): 1.02 min [M+1] 469. ¹H NMR (400 MHz, CDCl₃) δ ppm 1.28-1.39 (m, 3H) 3.43 (s, 6H) 3.82 (q, 2H) 4.05 (s, 3H) 7.43-7.61 (m, 1H) 8.44 (d, 1H) 8.60-8.67 (m, 1H) 8.77-8.86 (m, 1H) 8.89 (d, 1H).

Step B: Preparation of N-[5-ethylsulfonyl-6-[4-methyl-5-[4-(trifluoromethyl)-2-pyridyl]-1,2,4-triazol-3-yl]-3-pyridyl]methanesulfonamide

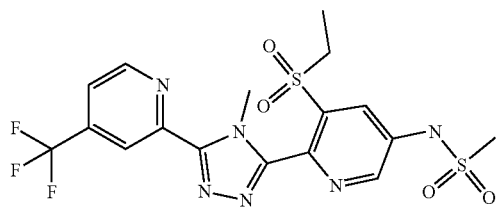 [SMILES: CCS(=O)(=O)c1cc(NS(C)(=O)=O)cnc1-c1nnc(-c2cc(C(F)(F)F)ccn2)n1C]

Sodium hydroxide (50 mg, 0.7035 mmol) dissolved in 2 ml of water was added to a methanol (10 ml) solution of N-[5-ethylsulfonyl-6-[4-methyl-5-[4-(trifluoromethyl)-2-pyridyl]-1,2,4-triazol-3-yl]-3-pyridyl]-N-methylsulfonyl-methanesulfonamide (400 mg, 0.7035 mmol) and reaction was stirred at room temperature for 1 hour. Reaction was then quenched by adding hydrochloric acid (2 N aq. solution) and product was extracted with ethyl acetate. Organic layer was concentrated and purified on CombiFlash column chromatography gradient cyclohexane+0-70% EtOAc to give N-[5-ethylsulfonyl-6-[4-methyl-5-[4-(trifluoromethyl)-2-pyridyl]-1,2,4-triazol-3-yl]-3-pyridyl]-N-methylsulfonyl-methanesulfonamide (300 mg, 87%). Mp: 228-230° C. ¹H NMR (400 MHz, DMSO) δ ppm 1.22 (t, 3H) 3.30 (s, 3H) 3.68-3.82 (m, 2H) 3.88 (s, 3H) 7.97 (m, 1H) 8.29 (d, 1H) 8.50 (s, 1H) 8.86 (d, 1H) 9.05 (d, 1H) 10.93 (br. s., 1H).

Step C: Preparation of N-[5-ethylsulfonyl-6-[4-methyl-5-[4-(trifluoromethyl)-2-pyridyl]-1,2,4-triazol-3-yl]-3-pyridyl]-N-methyl-methanesulfonamide A12

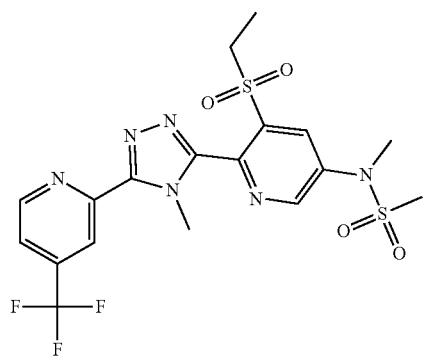

To a N,N-dimethylacetamide (161 mmol, 14.1 g) solution of N-[5-ethylsulfonyl-6-[4-methyl-5-[4-(trifluoromethyl)-2-pyridyl]-1,2,4-triazol-3-yl]-3-pyridyl]methanesulfonamide (0.5 g, 1.0194 mmol) at room temperature was added sodium hydride (81,5449 mg, 2.0388 mmol) followed by methyl iodide (0.291 g, 2.0388 mmol). Reaction was stirred at room temperature for 12 hours and then quenched by addition of water (50 ml). The reaction mixture was extracted with ethyl acetate. Organic layer was separated, concentrated to get crude product (400 mg) and purified by CombiFlash column chromatography gradient cyclohexane+0-50% EtOAc to give N-[5-ethylsulfonyl-6-[4-methyl-5-[4-(trifluoromethyl)-2-pyridyl]-1,2,4-triazol-3-yl]-3-pyridyl]-N-methyl-methanesulfonamide A12 (70 mg, 14%). Mp: 228-230° C. ¹H NMR (400 MHz, CDCl₃) δ ppm 1.41 (t, 3H) 3.05 (s, 3H) 3.17 (s, 1H) 3.53 (s, 3H) 3.88 (q, 2H) 4.11 (s, 3H) 7.62 (d, 1H) 8.45 (d, 1H) 8.72 (s, 1H) 8.90 (d, 1H) 9.03-9.21 (m, 1H).

Example P11: Preparation of N-[5-ethylsulfonyl-6-[4-methyl-5-[4-(trifluoromethyl)-2-pyridyl]-1,2,4-triazol-3-yl]-2-pyridyl]-N-methyl-methanesulfonamide A13

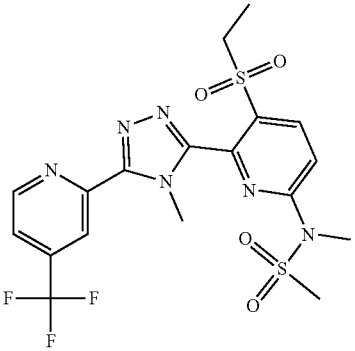

Step A: Preparation of N-[5-ethylsulfonyl-6-[4-methyl-5-[4-(trifluoromethyl)-2-pyridyl]-1,2,4-triazol-3-yl]-2-pyridyl]methanesulfonamide

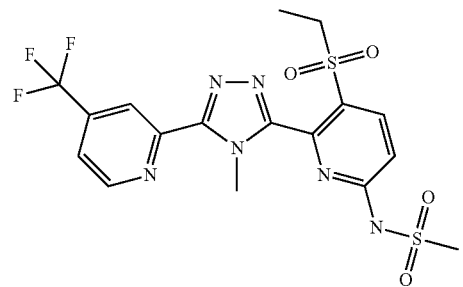 [SMILES: CCS(=O)(=O)c1ccc(NS(C)(=O)=O)nc1-c1nnc(-c2cc(C(F)(F)F)ccn2)n1C]

In a microwave vial was sequentially added 6-chloro-3-ethylsulfonyl-2-[4-methyl-5-[4-(trifluoromethyl)-2-pyridyl]-1,2,4-triazol-3-yl]pyridine (Prepared as descripted in Example P5, Step A and Step B) (670 mg, 1.552 mmol), dipotassium carbonic acid (0.4351 g, 3.103 mmol), methane sulfonamide (0.2214 g, 2.327 mmol) and N,N-dimethylformamide (7 mL). The reaction was heated in microwave at 150° C. for 1 hour and then diluted with water (10 ml), extracted with ethyl acetate. Combined organic layers were washed successively with water and brine, dried over Na₂SO₄ and concentrated in vacuo. The crude product was purified by CombiFlash column chromatography gradient cyclohexane+0-50% EtOAc to give N-[5-ethylsulfonyl-6-[4-methyl-5-[4-(trifluoromethyl)-2-pyridyl]-1,2,4-triazol-3-yl]-2-pyridyl]methanesulfonamide (500 mg, 65%). LCMS (method 1): 1.32 min, [M+1] 490. ¹H NMR (400 MHz, CDCl₃) δ 8.89 (d, 1H), 8.69 (s, 1H), 8.44 (d, 2H), 7.62 (d, 1H), 7.39 (d, 1H), 4.08 (s, 3H), 3.74 (q, 2H), 3.33 (s, 3H), 1.37 (t, 3H).

Step B: Preparation of N-[5-ethylsulfonyl-6-[4-methyl-5-[4-(trifluoromethyl)-2-pyridyl]-1,2,4-triazol-3-yl]-2-pyridyl]-N-methyl-methanesulfonamide A13

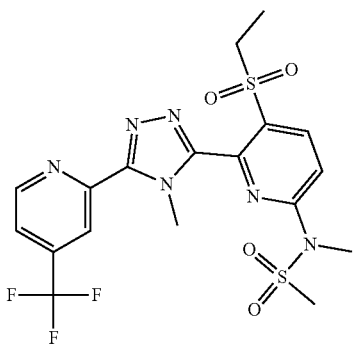

A13

To a solution of sodium hydride (34.25 mg, 0.8563 mmol) in tetrahydrofuran (2 ml) was added a solution of N-[5-ethylsulfonyl-6-[4-methyl-5-[4-(trifluoromethyl)-2-pyridyl]-1,2,4-triazol-3-yl]-2-pyridyl]methanesulfonamide (1280 mg, 0.5708 mmol) in tetrahydrofuran (3 ml). Reaction was stirred at room temperature for 30 mins. To this was then added iodomethane (0.2431 g, 1.713 mmol) and reaction mixture was stirred at 50° C. for 5 hours. The reaction was neutralized with 2N HCl (10 ml), aqueous layer extracted with ethyl acetate, combined organic layer was dried over sodium sulfate, concentrated under reduced pressure. Crude product was purified by flash column chromatography gradient cyclohexane+0-50% EtOAc to give N-[5-ethylsulfonyl-6-[4-methyl-5-[4-(trifluoromethyl)-2-pyridyl]-1,2,4-triazol-3-yl]-2-pyridyl]-N-methyl-methanesulfonamide A13 (130 mg, 45%) $^1$H NMR (400 MHz, CDCl$_3$) δ 8.88 (d, 1H), 8.71 (s, 1H), 8.46 (d, 1H), 7.67 (d, 1H), 7.61 (d, 1H), 4.10 (s, 3H), 3.81-3.71 (m, 2H), 3.54 (s, 3H), 3.22 (s, 3H), 1.42-1.34 (m, 3H).

Example P12: Preparation of N-[5-ethylsulfonyl-6-[4-methyl-5-[4-(trifluoromethyl)-2-pyridyl]-1,2,4-triazol-3-yl]-3-pyridyl]methanesulfonamide A14

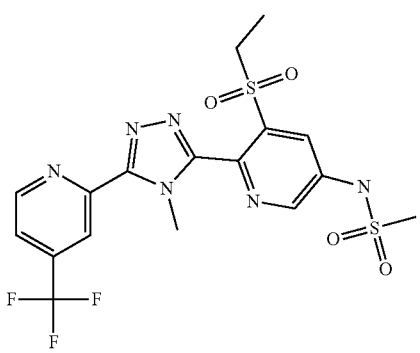

A14

In a stirring solution of N-[5-ethylsulfonyl-6-[4-methyl-5-[4-(trifluoromethyl)-2-pyridyl]-1,2,4-triazol-3-yl]-3-pyridyl]-N-methylsulfonyl-methanesulfonamide (Prepared in Example P10 Step A) (400 mg, 0.7035 mmol) in methanol (10 ml) was added aqueous sodium hydroxide (50 mg, 0.7035 mmol, dissolved in 2 ml of water) and reaction was stirred at room temperature for 1 hour. After complete conversion of starting material, acidic work up was done using 2 N HCl and product was extracted using ethyl acetate.

Organic phase was dried on magnesium sulfate and concentrated on vacuum to give N-[5-ethylsulfonyl-6-[4-methyl-5-[4-(trifluoromethyl)-2-pyridyl]-1,2,4-triazol-3-yl]-3-pyridyl]methanesulfonamide (300 mg, 86%). Mp: 228-230° C. $^1$H NMR (400 MHz, DMSO) δ ppm 1.22 (t, 3H) 3.30 (s, 3H) 3.68-3.82 (m, 2H) 3.88 (s, 3H) 7.97 (m, 1H) 8.29 (d, 1H) 8.50 (s, 1H) 8.86 (d, 1H) 9.05 (d, 1H) 10.93 (br. s., 1H).

Example P13: Preparation of N-[5-ethylsulfonyl-6-[4-methyl-5-[4-(trifluoromethyl)-2-pyridyl]-1,2,4-triazol-3-yl]-2-pyridyl]-N-methyl-methanesulfonamide A15

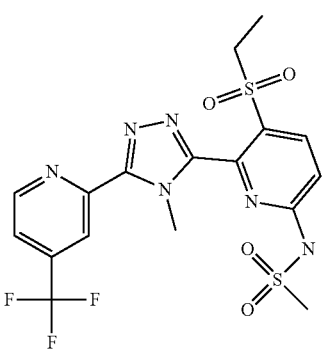

A15

In a microwave vial was sequentially added 6-chloro-3-ethylsulfonyl-2-[4-methyl-5-[4-(trifluoromethyl)-2-pyridyl]-1,2,4-triazol-3-yl]pyridine (prepared as descripted in Example P5 Step A and Step B) (670 mg, 1.552 mmol), dipotassium carbonic acid (0.4351 g, 3.103 mmol), methane sulfonamide (0.2214 g, 2.327 mmol) and N,N-dimethylformamide (7 mL). The reaction mixture was heated in microwave at 150° C. for 1 hour and then diluted with water (10 ml), extracted with ethyl acetate. Combined organic layers were washed successively with water and brine, dried over Na$_2$SO$_4$ and concentrated in vacuum. The title compound was purified by CombiFlash (silica gel, 50% EtOAc-cyclohexane). $^1$H NMR (400 MHz, CDCl$_3$) δ 8.89 (d, 1H), 8.69 (s, 1H), 8.44 (d, 2H), 7.62 (d, 1H), 7.39 (d, 1H), 4.08 (s, 3H), 3.74 (q, 2H), 3.33 (s, 3H), 1.37 (t, 3H).

Example P14: Preparation of N-cyclopropyl-5-ethylsulfonyl-N-methyl-6-[4-methyl-5-[4-(trifluoromethyl)-2-pyridyl]-1,2,4-triazol-3-yl]pyridine-3-carboxamide A16

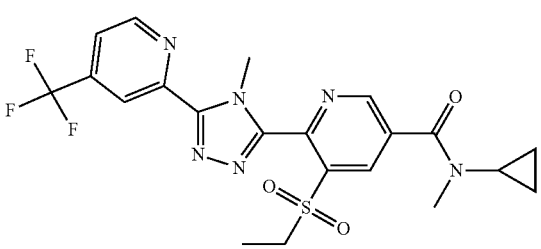

A16

Step A: Preparation of 5-ethylsulfonyl-6-[4-methyl-5-[4-(trifluoromethyl)-2-pyridyl]-1,2,4-triazol-3-yl]pyridine-3-carbonyl chloride

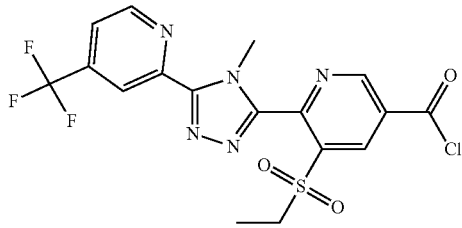 [SMILES: CCS(=O)(=O)c1cc(C(=O)Cl)cnc1-c1nnc(-c2cc(C(F)(F)F)ccn2)n1C]

In a stirring solution of 5-ethylsulfonyl-6-[4-methyl-5-[4-(trifluoromethyl)-2-pyridyl]-1,2,4-triazol-3-yl]pyridine-3-carboxylic acid A33 (1.5 g, 3.4 mmol) in dichloromethane (15 mL) was added oxalyl chloride (0.7 ml, 6.8 mmol)) and N,N-dimethylformamide (0.05 g, 0.6 mmol). Reaction mixture was stirred at 0° C. for 2 hours and then concentrated under vacuum to get 1.5 g crude acid chloride and used directly in next step.

Step B: Preparation of N-cyclopropyl-5-ethylsulfonyl-N-methyl-6-[4-methyl-5-[4-(trifluoromethyl)-2-pyridyl]-1,2,4-triazol-3-yl]pyridine-3-carboxamide A16

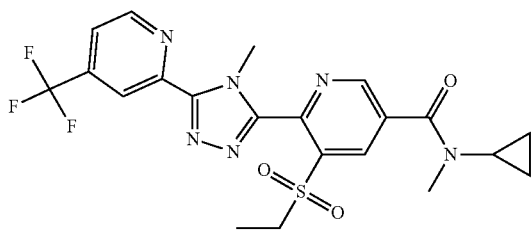

In a stirring solution of N-methylcyclopropyl amine (2.175 mmol, 0.1547 g) (HCL salt was used) in dichloromethane (10 mL) was added N,N-diethylethanamine (0.3301 g, 3.262 mmol) and 10 ml dichloromethane solution of 5-ethylsulfonyl-6-[4-methyl-5-[4-(trifluoromethyl)-2-pyridyl]-1,2,4-triazol-3-yl]pyridine-3-carbonyl chloride (0.5 g, 1.087 mmol). Reaction mixture was stirred at room temperature for 12 hours and then quenched by addition of aq. sodium carbonate solution (50 ml) and dichloromethane (20 ml). Organic layer was separated and concentrated to get crude product. It was purified by CombiFlash column chromatography gradient cyclohexane+0-70% EtOAc to give N-cyclopropyl-5-ethylsulfonyl-N-methyl-6-[4-methyl-5-[4-(trifluoromethyl)-2-pyridyl]-1,2,4-triazol-3-yl]pyridine-3-carboxamide (100 mg, 16%). Mp: 235-237° C. $^1$H NMR (400 MHz, CDCl$_3$) δ ppm 0.58 (br. s., 2H) 0.79 (br. s., 2H) 1.39 (t, 3H) 2.88-3.02 (m, 1H) 3.22 (br. s., 3H) 3.88 (t, 2H) 4.10 (s, 3H) 7.60 (d, 1H) 8.64-8.77 (m, 2H) 8.89 (d, 1H) 9.17 (s, 1H).

Example P15: Preparation of N-cyclopropyl-5-ethylsulfonyl-N-methyl-6-[4-methyl-5-[4-(trifluoromethyl)-2-pyridyl]-1,2,4-triazol-3-yl]pyridine-2-carboxamide A17

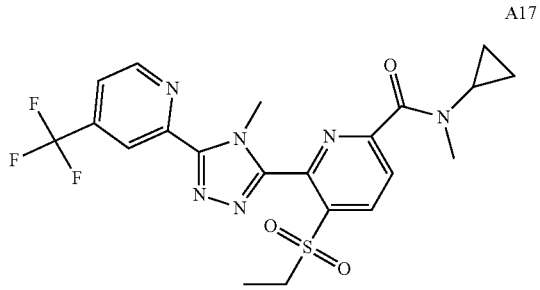 [SMILES: CCS(=O)(=O)c1ccc(C(=O)N(C)C2CC2)nc1-c1nnc(-c2cc(C(F)(F)F)ccn2)n1C]

Step A: Preparation of 5-ethylsulfonyl-6-[4-methyl-5-[4-(trifluoromethyl)-2-pyridyl]-1,2,4-triazol-3-yl]pyridine-2-carbonyl chloride

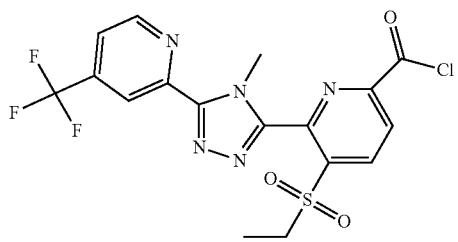 [SMILES: CCS(=O)(=O)c1ccc(C(=O)Cl)nc1-c1nnc(-c2cc(C(F)(F)F)ccn2)n1C]

To an ice cold solution of 5-ethylsulfonyl-6-[4-methyl-5-[4-(trifluoromethyl)-2-pyridyl]-1,2,4-triazol-3-yl]pyridine-2-carboxylic acid (300 mg, 0.6797 mmol) in dichloromethane (10 mL) was added oxalyl chloride (0.1725 g, 1.359 mmol) under nitrogen atmosphere. Reaction was then allowed to warm to room temperature. Reaction mixture was concentrated under vacuum and directly used for next step amide coupling.

Step B: Preparation of N-cyclopropyl-5-ethylsulfonyl-N-methyl-6-[4-methyl-5-[4-(trifluoromethyl)-2-pyridyl]-1,2,4-triazol-3-yl]pyridine-2-carboxamide A17

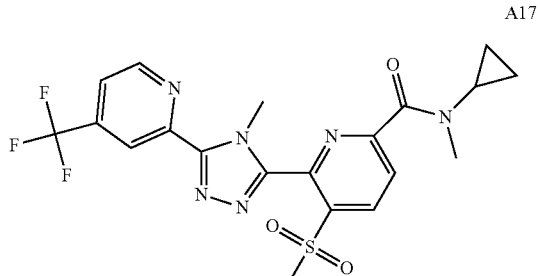

In an ice cold stirring suspension of N-methylcyclopropyl amine hydrochloride (87.60 mg, 0.8143 mmol) in dichloromethane (20 mL) was sequentially added N,N-diethylethanamine (0.2747 g, 0.364 mL) and 5-ethylsulfonyl-6-[4-methyl-5-[4-(trifluoromethyl)-2-pyridyl]-1,2,4-triazol-3-yl]pyridine-2-carbonyl chloride (312 mg, 0.678 mmol). The reaction mixture was stirred at room temperature for 12 hours under nitrogen atmosphere. The reaction mixture was then poured onto water and extracted with dichloromethane, the combined extracts were washed with brine, dried over magnesium sulfate, filtered and concentrated under reduced pressure. The crude product was purified via CombiFlash column chromatography gradient cyclohexane+0-40% EtOAc to give N-cyclopropyl-5-ethylsulfonyl-N-methyl-6-[4-methyl-5-[4-(trifluoromethyl)-2-pyridyl]-1,2,4-triazol-3-yl]pyridine-2-carboxamide (180 mg, 53.6%). ¹H NMR (400 MHz, CDCl₃) δ ppm 0.41-0.51 (m, 2H) 0.55-0.66 (m, 2H) 1.33 (t, 3H) 2.93-3.03 (m, 1H) 3.18 (s, 3H) 3.73-3.87 (m, 2H) 4.05 (s, 3H) 7.58 (d, 1H) 7.90 (d, 1H) 8.62 (d, 1H) 8.71 (s, 1H) 8.87 (d, 1H).

Example P16: Preparation of N-cyclopropyl-5-ethylsulfonyl-6-[4-methyl-5-[4-(trifluoromethyl)-2-pyridyl]-1,2,4-triazol-3-yl]pyridine-3-carboxamide A18

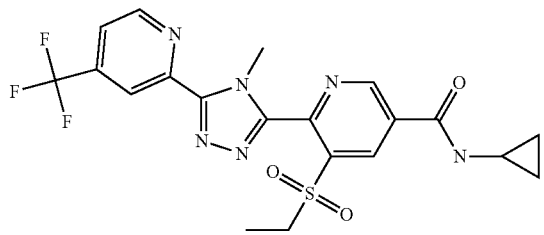

In a stirring solution of 5-ethylsulfonyl-6-[4-methyl-5-[4-(trifluoromethyl)-2-pyridyl]-1,2,4-triazol-3-yl]pyridine-3-carboxylic acid A33 (500 mg, 1.133 mmol) in dichloromethane (20 mL) was added oxalyl chloride (0.25 ml, 0.26 mmol) and one drop of DMF. The reaction mixture was stirred at room temperature for 1 hour and then concentrated under reduced pressure to get crude acid chloride. In another round bottom flask was taken cyclopropyl amine (97 mg, 1.7 mmol) in dichloromethane (20 mL) and then was added N,N-diethylethanamine (3.398 mmol, 0.6 ml) followed by addition of dichloromethane solution of acid chloride (prepared as above). The reaction was stirred at room temperature for overnight and then quenched by addition of aq. sodium carbonate. Dichloromethane layer was separated, concentrated to get crude product and purified by CombiFlash column chromatography gradient cyclohexane+0-70% EtOAc to give N-cyclopropyl-5-ethylsulfonyl-6-[4-methyl-5-[4-(trifluoromethyl)-2-pyridyl]-1,2,4-triazol-3-yl]pyridine-3-carboxamide (360 mg, 66%). Mp: 196-198° C. ¹H NMR (400 MHz, CDCl₃) δ ppm 0.67-0.80 (m, 2H) 0.94-1.03 (m, 2H) 1.41 (t, 3H) 3.02 (m, 1H) 3.90 (q, 2H) 4.10 (s, 3H) 6.60 (br. s., 1H) 7.62 (d, 1H) 8.72 (s, 1H) 8.75 (d, 1H) 8.89 (d, 1H) 9.41 (d, 1H).

Example P17: Preparation of N-cyclopropyl-5-ethylsulfonyl-6-[4-methyl-5-[4-(trifluoromethyl)-2-pyridyl]-1,2,4-triazol-3-yl]pyridine-2-carboxamide A19

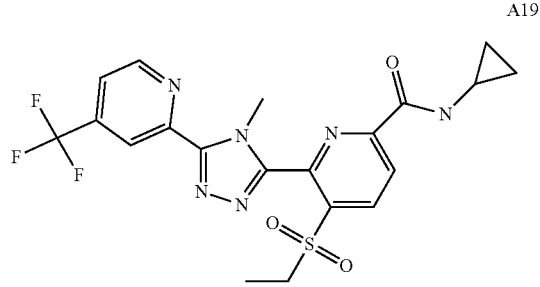 [SMILES: CCS(=O)(=O)c1ccc(C(=O)NC2CC2)nc1-c1nnc(-c2cc(C(F)(F)F)ccn2)n1C]

In an ice cold stirring solution of cyclopropyl amine (46.49 mg, 0.8143 mmol) in dichloromethane (10 mL) was added N,N-diethylethanamine (0.364 mL, 0.2747 g) followed by 5-ethylsulfonyl-6-[4-methyl-5-[4-(trifluoromethyl)-2-pyridyl]-1,2,4-triazol-3-yl]pyridine-2-carbonyl chloride (as prepared in Example P15 step A) (312 mg, 0.6786 mmol) and reaction was stirred at room temperature for 12 hours. The reaction mixture was then poured onto water and extracted with dichloromethane (3×). The combined extracts were washed with brine, dried sodium sulfate and evaporated under reduced pressure. The crude product was purified by column chromatography gradient cyclohexane+0-40% EtOAc to give N-cyclopropyl-5-ethylsulfonyl-6-[4-methyl-5-[4-(trifluoromethyl)-2-pyridyl]-1,2,4-triazol-3-yl]pyridine-2-carboxamide (160 mg, 49.07%). ¹H NMR (400 MHz, CDCl₃) δ ppm 0.66-0.72 (m, 2H) 0.88-0.98 (m, 2H) 1.36 (t, 3H) 2.98 (m, 1H) 3.71 (q, 2H) 4.01 (s, 3H) 7.64 (m, 1H) 7.81-7.89 (m, 1H) 8.56-8.62 (m, 1H) 8.66-8.74 (m, 2H) 8.87-8.93 (m, 1H).

Example P18: N-[5-ethylsulfonyl-6-[4-methyl-5-[4-(trifluoromethyl)-2-pyridyl]-1,2,4-triazol-3-yl]-3-pyridyl]-N-methylsulfonyl-cyclopropanecarboxamide A20

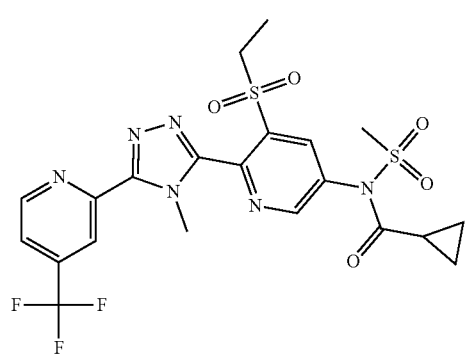

In a stirring solution of N-[5-ethylsulfonyl-6-[4-methyl-5-[4-(trifluoromethyl)-2-pyridyl]-1,2,4-triazol-3-yl]-3-pyridyl]methanesulfonamide A14 (170 g, 346.6 mmol) in dichloromethane (10 mL) was added N,N-diethylethanamine (0.11 ml) followed by cyclopropyl carbonyl chloride (0.07 ml). The reaction was stirred at room temperature for 2 hours and then quenched by adding saturated aq. sodium bicarbonate solution. Organic layer was separated, concentrated under reduced pressure and purified by column chromatography gradient cyclohexane+0-70% EtOAc to give N-[5-ethylsulfonyl-6-[4-methyl-5-[4-(trifluoromethyl)-2-pyridyl]-1,2,4-triazol-3-yl]-3-pyridyl]-N-methylsulfonyl-cyclopropanecarboxamide (110 mg, 57%). Mp: 229-231° C. $^1$H NMR (400 MHz, CDCl$_3$) δ ppm 1.00-1.08 (m, 2H) 1.34 (m, 2H) 1.42 (t, 4H) 3.57 (s, 3H) 3.93 (q, 2H) 4.16 (s, 3H) 7.64 (d, 1H) 8.53 (d, 1H) 8.74 (s, 1H) 8.92 (d, 1H) 9.01 (d, 1H).

Example P20: N'-[5-ethylsulfonyl-6-[4-methyl-5-[4-(trifluoromethyl)-2-pyridyl]-1,2,4-triazol-3-yl]-3-pyridyl]-N,N'-dimethyl-cyclopropanecarbohydrazide A21

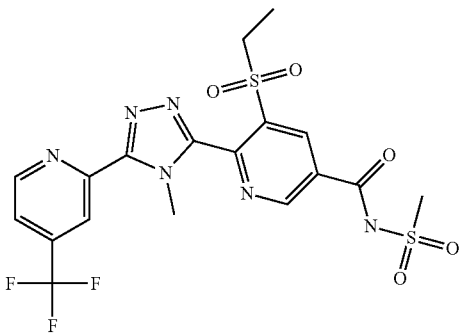

A21

To a stirring solution of 5-ethylsulfonyl-6-[4-methyl-5-[4-(trifluoromethyl)-2-pyridyl]-1,2,4-triazol-3-yl]pyridine-3-carboxylic acid A33 (1.4 g, 2.2 mmol) in dichloromethane (20 ml) was added one drop N,N-dimethylformamide followed by addition of oxalyl chloride (0.34 g, 2.7 mmol) over period of 20 min. The reaction mixture was stirred at room temperature for 25 min. After completion of reaction, reaction mass was evaporated off under reduced pressure. Obtained reaction mass was diluted with dichloromethane (20 ml) and added to a stirring solution of methane sulfonamide (0.25 g, 2.7 mmol) and N,N-diethylethanamine (0.90 g, 8.9 mmol) in dichloromethane (30 ml) at 0° C. over period of 20 min. Completion of reaction was monitored by TLC. After completion of reaction, reaction mass was diluted with dichloromethane (40 ml) and washed with water, dried over sodium sulfate, filtered and evaporated off under reduced pressure. Thus obtained solid compounds was dissolved in methanol (30 mL) stirred for 5 min, filtered and washed with acetone (30 ml) and dried under vacuum to give N'-[5-ethylsulfonyl-6-[4-methyl-5-[4-(trifluoromethyl)-2-pyridyl]-1,2,4-triazol-3-yl]-3-pyridyl]-N,N'-dimethyl-cyclopropanecarbohydrazide (230 mg, 20%). Mp: 286-288° C. $^1$H NMR (400 MHz, METHANOL-d4) δ ppm 1.36 (t, 3H) 3.44 (s, 3H) 3.76 (q, 2H) 4.04 (s, 3H) 7.80 (br. s., 1H) 8.55 (s, 1H) 9.00 (d, 2H) 9.48 (d, 1H).

Example P21: 1-[[5-ethylsulfonyl-6-[4-methyl-5-[4-(trifluoromethyl)-2-pyridyl]-1,2,4-triazol-3-yl]-3-pyridyl]amino]cyclopropanecarbonitrile A22

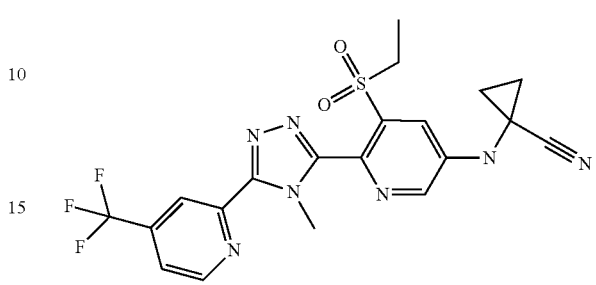

A22

In a 10 ml vial tube, 5-bromo-3-ethylsulfonyl-2-[4-methyl-5-[4-(trifluoromethyl)-2-pyridyl]-1,2,4-triazol-3-yl]pyridine (Prepared as descripted in Example P6, Step A and Step B) (300 mg, 0.6299 mmol) was dissolved in anhydrous 1,4-dioxane (2.5 mL) and to it cesium carbonate (1.386 mmol, 0.452 g) was added under nitrogen followed by the addition of palladium (II) acetate (0.03779 mmol, 0.008489 g) and (1-cyanocyclopropyl)ammonium chloride (0.8188 mmol, 0.09708 g). Reaction mixture was degassed with nitrogen for 15-20 mins, X-PHOS (0.1134 mmol, 0.05515 g) was then added and the reaction mixture was heated at 110° C. in a preheated oil bath for 24 hours in a sealed tube. In order to complete the reaction cesium carbonate (1.8 eq.=360 mg) was again added to reaction mixture and reaction mixture was further heated at 110° C. for another 30 hours. Reaction mixture was quenched with water (15 ml) and extracted with ethyl acetate (2×20 ml). Organic layer was separated, washed with brine, dried over sodium sulfate and concentrated to get crude product. Column purification gradient cyclohexane+0-30% EtOAc was performed to provide 1-[[5-ethylsulfonyl-6-[4-methyl-5-[4-(trifluoromethyl)-2-pyridyl]-1,2,4-triazol-3-yl]-3-pyridyl]amino]cyclopropanecarbonitrile (120 mg, 39%). Mp: 202-204° C. $^1$H NMR (400 MHz, CDCl$_3$) δ ppm 1.34-1.40 (t, 3H) 1.40-1.44 (m, 2H) 1.70-1.77 (m, 2H) 3.72-3.83 (m, 2H) 4.03 (s, 3H) 5.47 (s, 1H) 7.59 (d, 1H) 7.88 (d, 1H) 8.56 (d, 1H) 8.69 (s, 1H) 8.87 (d, 1H).

Example P22: N-(1-cyanocyclopropyl)-5-ethylsulfonyl-6-[4-methyl-5-[4-(trifluoromethyl)-2-pyridyl]-1,2,4-triazol-3-yl]pyridine-3-carboxamide A23

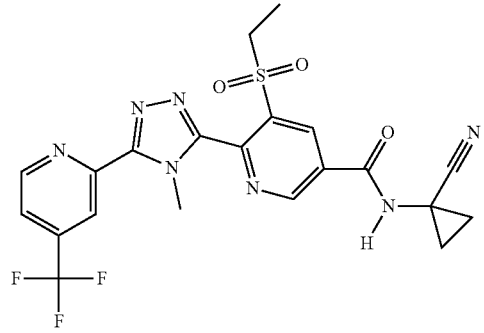

A23

In a stirring solution of 1-aminocyclopropanecarbonitrile hydrochloride (0.4785 mmol, 0.05673 g) in dichloromethane (10 mL) was added N,N-diethylethanamine (1.305 mmol, 0.1320 g) followed by 5-ethylsulfonyl-6-[4-methyl-5-[4-(trifluoromethyl)-2-pyridyl]-1,2,4-triazol-3-yl]pyridine-3-carbonyl chloride (Prepared as described in Example P14 Step A) (0.4350 mmol, 0.2 g, dissolved in 10 ml of dichloromethane) and reaction was stirred at room temperature for 12 hour. Reaction mixture was washed with sodium bicarbonate solution (100 ml) and dichloromethane layer (100 ml) was separated and concentrated to get crude product and purified by flash column chromatography gradient cyclohexane+0-70% EtOAc to give N-(1-cyanocyclopropyl)-5-ethylsulfonyl-6-[4-methyl-5-[4-(trifluoromethyl)-2-pyridyl]-1,2,4-triazol-3-yl]pyridine-3-carboxamide A23 (60 mg, 27%). Mp: 211-213° C. $^1$H NMR (400 MHz, CDCl$_3$) δ ppm 1.38 (t, 3H) 1.47-1.54 (m, 2H) 1.69-1.76 (m, 2H) 3.85 (q, 2H) 4.09 (s, 3H) 7.64 (d, 1H) 8.21 (s, 1H) 8.69 (s, 1H) 8.86 (d, 1H) 8.90 (d, 1H) 9.46 (d, 1H).

Example P23: N-[5-ethylsulfonyl-6-[4-methyl-5-[4-(trifluoromethyl)-2-pyridyl]-1,2,4-triazol-3-yl]-3-pyridyl]-N'-methoxy-formamidine A24

A24

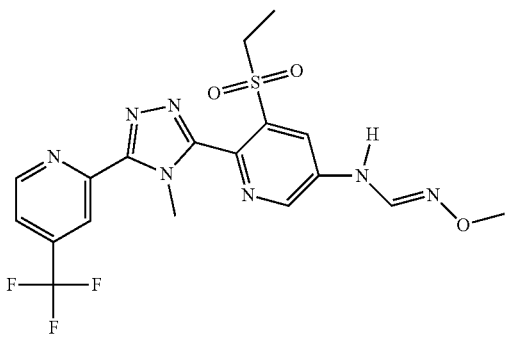

A solution of 5-ethylsulfonyl-6-[4-methyl-5-[4-(trifluoromethyl)-2-pyridyl]-1,2,4-triazol-3-yl]pyridin-3-amine A35 (400 mg, 0.9699 mmol), 1,1-dimethoxy-N,N-dimethyl-methanamine (1.164 mmol, 100 mass %) in acetonitrile (5 mL, 100 mass %) was refluxed for 1 hr. The reaction was concentrated under reduced pressure to obtain N'-[5-ethylsulfonyl-6-[4-methyl-5-[4-(trifluoromethyl)-2-pyridyl]-1,2,4-triazol-3-yl]-3-pyridyl]-N,N-dimethyl-formamidine (400 mg, 88.21%).

To a solution of N'-[5-ethylsulfonyl-6-[4-methyl-5-[4-(trifluoromethyl)-2-pyridyl]-1,2,4-triazol-3-yl]-3-pyridyl]-N,N-dimethyl-formamidine (400 mg, 0.8556 mmol) in methanol (5 mL) was added O-methyl hydroxylamine hydrochloride (1.2 equiv., 1.027 mmol). Reaction mixture was refluxed for 1 hour and monitored by TLC. The reaction was quenched with water (5 ml), extracted with ethyl acetate and combined organic layer was dried over sodium sulfate, filtered, concentrated under reduced pressure, and purified by CombiFlash column chromatography gradient cyclohexane+0-100% EtOAc to give N-[5-ethylsulfonyl-6-[4-methyl-5-[4-(trifluoromethyl)-2-pyridyl]-1,2,4-triazol-3-yl]-3-pyridyl]-N'-methoxy-formamidine A24 (200 mg, 49%). $^1$H NMR (400 MHz, CDCl$_3$) δ 8.87 (d, 1H), 8.70 (s, 1H), 8.62 (d, 1H), 7.98 (d, 1H), 7.58 (d, 2H), 7.41 (d, 1H), 4.03 (s, 3H), 3.96 (s, 3H), 3.87-3.76 (m, 2H), 1.38 (t, 3H)

Example P24: N-[5-ethylsulfonyl-6-[4-methyl-5-[4-(trifluoromethyl)-2-pyridyl]-1,2,4-triazol-3-yl]-3-pyridyl]-N'-methoxy-N-methyl-formamidine A25

A25

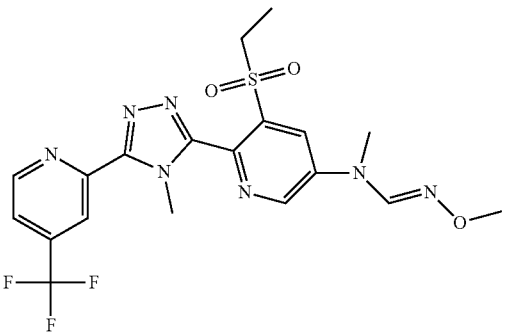

To a solution of N-[5-ethylsulfonyl-6-[4-methyl-5-[4-(trifluoromethyl)-2-pyridyl]-1,2,4-triazol-3-yl]-3-pyridyl]-N'-methoxy-formamidine (300 mg, 0.6391 mmol) in N,N-dimethylformamide (4 mL) was added dipotassium carbonate (134 mg, 0.958 mmol) followed by iodomethane (0.062 ml, 0.958 mmol). The reaction was stirred at room temperature for overnight and then neutralized with 2N HCl (5 ml), diluted with water (10 ml), extracted with ethyl acetate. The combined organic layers were washed successively with water and brine, dried over Na$_2$SO$_4$ and concentrated in vacuo. The residue was purified by CombiFlash column chromatography gradient cyclohexane+0-50% EtOAc to give N-[5-ethylsulfonyl-6-[4-methyl-5-[4-(trifluoromethyl)-2-pyridyl]-1,2,4-triazol-3-yl]-3-pyridyl]-N'-methoxy-N-methyl-formamidine A25 (120 mg, 38%). $^1$H NMR (400 MHz, CDCl$_3$) δ 8.86 (d, 1H), 8.77-8.66 (m, 2H), 8.46 (s, 1H), 8.07 (d, 1H), 7.58 (d, 1H), 4.03 (s, 3H), 3.86 (s, 3H), 3.80 (m, 2H), 3.46 (s, 3H), 1.37 (t, 3H).

Example 25: Preparation of N-(cyanomethyl)-5-ethylsulfonyl-6-[4-methyl-5-[4-(trifluoromethyl)-2-pyridyl]-1,2,4-triazol-3-yl]pyridine-3-carboxamide A26

A26

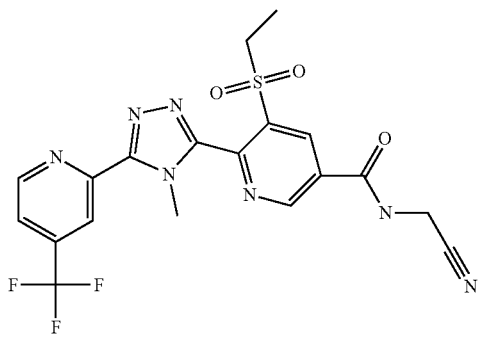

In an ice cold stirring solution of 5-ethylsulfonyl-6-[4-methyl-5-[4-(trifluoromethyl)-2-pyridyl]-1,2,4-triazol-3-yl]

pyridine-3-carboxylic acid (0.7929 mmol, 0.35 g) in dichloromethane (10 mL) was added oxalyl chloride (0.9515 mmol, 0.1232 g) and the reaction mixture was stirred at room temperature for 2 hour. Acid chloride formation was monitored by TLC. The reaction mixture was concentrated under vacuum at 50° C. to remove excess acid chloride. In another flask was taken HCl salt of 2-aminoacetonitrile (0.8722 mmol, 0.04890 g) in dichloromethane (10 mL) and to this was added above acid chloride after dissolving in dichloromethane (10 ml). Reaction was stirred at room temperature for 12 hour. Reaction was washed by sodium bicarbonate solution (100 ml) and product was extracted with dichloromethane. Organic layer was concentrated to get crude product, it was purified by CombiFlash column chromatography gradient cyclohexane+0-50% EtOAc to give N-(cyanomethyl)-5-ethylsulfonyl-6-[4-methyl-5-[4-(trifluoromethyl)-2-pyridyl]-1,2,4-triazol-3-yl]pyridine-3-carboxamide A26 (70 mg, 18%). Mp: 219-221° C. $^1$H NMR (400 MHz, CDCl$_3$) δ ppm 1.31 (t, 3H) 3.83 (q, 2H) 4.02 (s, 3H) 4.38 (d, 2H) 7.54 (d, 1H) 7.97 (m, 1H), 8.61 (s, 1H) 8.81 (m, 2H), 9.41 (s, 1H).

Example P26: Preparation of N-[5-ethylsulfonyl-6-[4-methyl-5-[4-(trifluoromethyl)-2-pyridyl]-1,2,4-triazol-3-yl]-3-pyridyl]-N-methylsulfonyl-methanesulfonamide A27

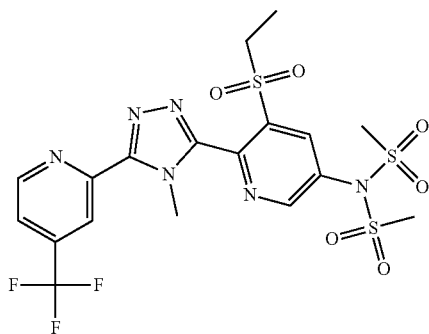

A27

In a stirring solution of 5-ethylsulfonyl-6-[4-methyl-5-[4-(trifluoromethyl)-2-pyridyl]-1,2,4-triazol-3-yl]pyridin-3-amine A35 (1 g, 2.425 mmol) in dichloromethane (15 mL) was added triethylamine (0.7 ml) followed by methane sulfonyl chloride (4.850 mmol) (0.5 ml). The reaction mixture was stirred at room temperature for 1 hour and then washed by sodium bicarbonate solution. Organic layer was concentrated to get crude product and purified on CombiFlash column chromatography gradient cyclohexane+0-70% EtOAc to give N-[5-ethylsulfonyl-6-[4-methyl-5-[4-(trifluoromethyl)-2-pyridyl]-1,2,4-triazol-3-yl]-3-pyridyl]-N-methylsulfonyl-methanesulfonamide A27 (450 mg, 32%). Mp: 253-255° C. $^1$H NMR (400 MHz, CDCl$_3$) δ ppm 1.31 (t, 3H) 3.43 (s, 6H) 3.82 (q, 2H) 4.05 (s, 3H) 7.43 (m, 1H) 8.44 (d, 1H) 8.60-8.67 (m, 1H) 8.77-8.86 (m, 1H) 8.89 (d, 1H).

Example P27: Preparation of 5-ethylsulfonyl-N-methyl-6-[4-methyl-5-[4-(trifluoromethyl)-2-pyridyl]-1,2,4-triazol-3-yl]-N-(2,2,2-trifluoroethyl) pyridin-2-amine A28

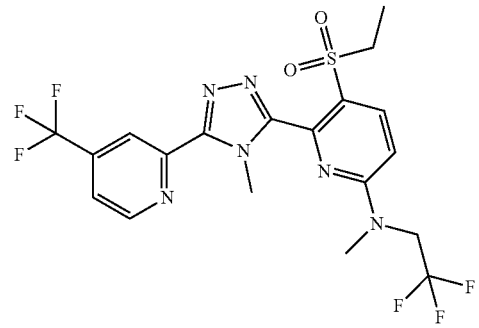

A28

5-ethylsulfonyl-6-[4-methyl-5-[4-(trifluoromethyl)-2-pyridyl]-1,2,4-triazol-3-yl]-N-(2,2,2-trifluoroethyl)pyridin-2-amine (0.2023 mmol, 0.1 g) was dissolved in anhydrous N,N-dimethylformamide (1 mL) and to it sodium hydride (0.2629 mmol, 0.01052 g) was added under nitrogen at 0° C. Reaction mixture was stirred at 0° C. for 15 mins followed by addition of iodomethane (0.2225 mmol, 0.03158 g, 0.0139 mL). The reaction mixture was stirred at room temperature for 2 hours and then quenched by adding methanol (0.5 ml). Compound was extracted with ethyl acetate and combined organic extract was washed successively with water and brine, dried over Na$_2$SO$_4$ and concentrated in vacuo to get the crude product. The title compound was purified in CombiFlash column chromatography gradient cyclohexane+0-50% EtOAc chromatography to give 5-ethylsulfonyl-N-methyl-6-[4-methyl-5-[4-(trifluoromethyl)-2-pyridyl]-1,2,4-triazol-3-yl]-N-(2,2,2-trifluoroethyl) pyridin-2-amine (87 mg, 84%). $^1$H NMR (400 MHz, CDCl$_3$) δ ppm 1.32 (t, 3H) 3.26 (s, 3H) 3.58-3.74 (m, 2H) 3.99 (s, 3H) 4.29-4.49 (m, 2H) 6.83 (d, 1H) 7.51 (d, 1H) 8.16 (d, 1H) 8.61 (d, 1H) 8.84 (d, 1H).

Example P28: Preparation of N-[5-ethylsulfonyl-6-[4-methyl-5-[4-(trifluoromethyl)-2-pyridyl]-1,2,4-triazol-3-yl]-2-pyridyl]-N-(2,2,2-trifluoroethyl)cyclopropanecarboxamide A29

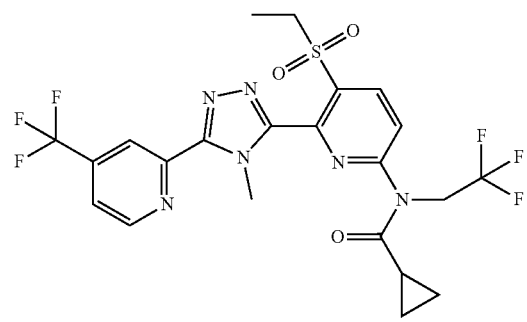

A29

5-ethylsulfonyl-6-[4-methyl-5-[4-(trifluoromethyl)-2-pyridyl]-1,2,4-triazol-3-yl]-N-(2,2,2-trifluoroethyl)pyridin- 2-amine (0.2023 mmol, 0.1 g) was dissolved in anhydrous dichloromethane (2 mL) under nitrogen atmosphere and to it N,N-diethylethanamine (1.011 mmol, 0.141 mL) followed by cyclopropyl carbonyl chloride (0.6068 mmol, 0.06343 g) and N,N-dimethylpyridin-4-amine (0.2023 mmol, 0.02471 g) were added. The reaction mixture was stirred at room temperature for 3 hours. Reaction was monitored by TLC and after the completion of the reaction, it was quenched with water (10 ml) and compound was extracted with ethyl acetate. The combined organic extract were washed successively with water and brine, dried over $Na_2SO_4$ and concentrated in vacuo. The residue was purified by column chromatography gradient cyclohexane+0-50% EtOAc to give N-[5-ethylsulfonyl-6-[4-methyl-5-[4-(trifluoromethyl)-2-pyridyl]-1,2,4-triazol-3-yl]-2-pyridyl]-N-(2,2,2-trifluoroethyl)cyclopropanecarboxamide (61 mg, 53%). $^1$H NMR (400 MHz, $CDCl_3$) δ ppm 0.99-1.09 (m, 2H) 1.27-1.33 (m, 2H) 1.39 (t, 3H) 1.77-1.89 (m, 1H) 3.67-3.87 (m, 2H) 4.04 (s, 3H) 4.91 (q, 2H) 7.55-7.69 (m, 1H) 7.90 (d, 1H) 8.53 (d, 1H) 8.71 (s, 1H) 8.89 (d, 1H).

Example P29: Preparation of 1-[5-ethylsulfonyl-6-[4-methyl-5-[4-(trifluoromethyl)-2-pyridyl]-1,2,4-triazol-3-yl]-3-pyridyl]-1-methyl-hydrazine A30

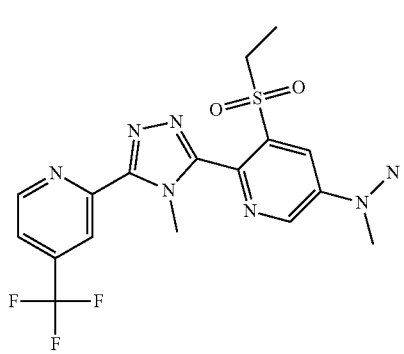

A30

Step A: N-(benzhydrylideneamino)-5-ethylsulfonyl-6-[4-methyl-5-[4-(trifluoromethyl)-2-pyridyl]-1,2,4-triazol-3-yl]pyridin-3-amine

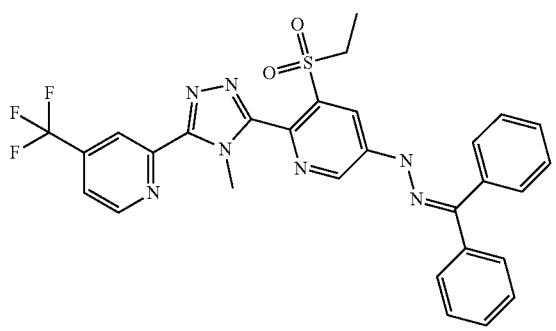 [SMILES: CCS(=O)(=O)c1cc(NN=C(c2ccccc2)c2ccccc2)cnc1-c1nnc(-c2cc(C(F)(F)F)ccn2)n1C]

5-bromo-3-ethylsulfonyl-2-[4-methyl-5-[4-(trifluoromethyl)-2-pyridyl]-1,2,4-triazol-3-yl]pyridine (Prepared as described in Example P1, Step A-1 to step C-2) (4.199 mmol, 2 g) was dissolved in 2-methylbutan-2-ol (4 mL) and degassed, purged with nitrogen for 20 min. NaOH (5.879 mmol, 0.2351 g) was then added to the above solution under nitrogen atmosphere and reaction mixture was heated at 110° C. In another round flask, PALLADIUM(II)ACETATE (0.2100 mmol, 0.04716 g) and MEPHOS (0.4199 mmol, 0.1562 g) were taken together and stirred under nitrogen atmosphere for 20 mins. This active catalyst was then transferred to the above reaction mixture followed by portion wise addition of diphenylmethanone hydrazone (4.199 mmol, 0.8239 g). Reaction mixture was heated at 110° C. for 5 hours, cooled and then filtered through celite bed and washed with ethyl acetate (10 ml). Organic layer was evaporated under vacuum and directly subjected to column chromatography gradient cyclohexane+0-40% EtOAc to give N-(benzhydrylideneamino)-5-ethylsulfonyl-6-[4-methyl-5-[4-(trifluoromethyl)-2-pyridyl]-1,2,4-triazol-3-yl]pyridin-3-amine (1.3 g, 52%). LCMS and NMR showed the desired product. $^1$H NMR (400 MHz, $CDCl_3$) δ ppm 1.37 (t, 3H) 3.78 (q, 2H) 4.01 (s, 3H) 7.34-7.43 (m, 5H) 7.57 (dd, 1H) 7.59-7.70 (m, 5H) 7.85 (s, 1H) 8.03 (d, 1H) 8.70 (d, 1H) 8.80 (d, 1H) 8.85 (d, 1H).

Step B: N-(benzhydrylideneamino)-5-ethylsulfonyl-N-methyl-6-[4-methyl-5-[4-(trifluoromethyl)-2-pyridyl]-1,2,4-triazol-3-yl]pyridin-3-amine

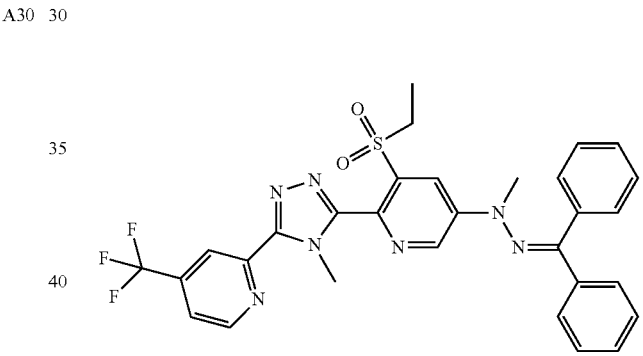

In a 10 ml round flask, sodium hydride (0.2535 mmol, 60 mass %) was added to the ice cold tetrahydrofuran (0.5 ml). To the above suspension, clear brown solution of N-(benzhydrylideneamino)-5-ethylsulfonyl-6-[4-methyl-5-[4-(trifluoromethyl)-2-pyridyl]-1,2,4-triazol-3-yl]pyridin-3-amine (100 mg, 0.1690 mmol) in tetrahydrofuran (1 ml) was added dropwise. After 10 min stirring under ice bath iodomethane (0.2028 mmol) was added and reaction mixture was stirred at room temperature for 1 hour and then quenched with 10 ml water. Reaction mixture was extracted with ethyl acetate (2×15 ml), organic layer was evaporated under vacuum and directly subjected to column chromatography gradient cyclohexane+0-50% EtOAc to give N-(benzhydrylideneamino)-5-ethylsulfonyl-N-methyl-6-[4-methyl-5-[4-(trifluoromethyl)-2-pyridyl]-1,2,4-triazol-3-yl]pyridin-3-amine (95 mg, 94%). H NMR (400 MHz, $CDCl_3$) δ ppm 1.38 (t, 3H) 3.00 (s, 3H) 3.75 (q, 2H) 4.03 (s, 3H) 7.34-7.44 (m, 4H) 7.46-7.54 (m, 4H) 7.57 (m, 1H) 7.62-7.69 (m, 2H) 7.94 (d, 1H) 8.70 (s, 1H) 8.78 (d, 1H) 8.85 (d, 1H).

Step C: Preparation of 1-[5-ethylsulfonyl-6-[4-methyl-5-[4-(trifluoromethyl)-2-pyridyl]-1,2,4-triazol-3-yl]-3-pyridyl]-1-methyl-hydrazine A30

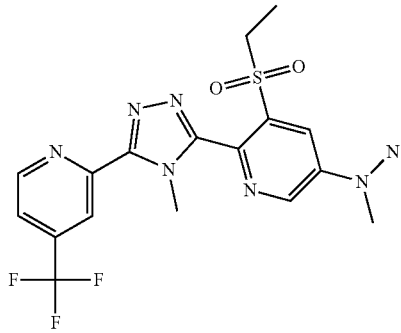

In a 10 ml round flask, N-(benzhydrylideneamino)-5-ethylsulfonyl-N-methyl-6-[4-methyl-5-[4-(trifluoromethyl)-2-pyridyl]-1,2,4-triazol-3-yl]pyridin-3-amine (90 mg, 0.1486 mmol) was dissolved in ethanol (1 mL). To this solution, concentrated HCl (0.22 ml) was added and reaction mixture was stirred for 16 hour at room temperature. After complete conversion of starting material, reaction mixture was cooled to 0° C. and quenched with aq. saturated NaHCO$_3$ solution and then was followed by addition of 5 ml of water. The solution was extracted with ethyl acetate (2×15 ml), combined organic layer were dried on magnesium sulfate and evaporated under vacuum. Crude product was purified by column chromatography gradient cyclohexane+ 0-100% EtOAc to give 1-[5-ethylsulfonyl-6-[4-methyl-5-[4-(trifluoromethyl)-2-pyridyl]-1,2,4-triazol-3-yl]-3-pyridyl]-1-methyl-hydrazine (30 mg, 46%). $^1$H NMR (400 MHz, CDCl$_3$) δ ppm 1.36 (t, 4H) 3.36 (s, 3H) 3.73 (q, 2H) 3.99 (s, 3H) 7.52 (m, 1H) 7.93 (d, 1H) 8.67-8.75 (m, 2H) 8.85 (d, 1H).

Example P19: N'-[5-ethylsulfonyl-6-[4-methyl-5-[4-(trifluoromethyl)-2-pyridyl]-1,2,4-triazol-3-yl]-3-pyridyl]-N,N'-dimethyl-cyclopropanecarbohydrazide A31

Step A: N'-[5-ethylsulfonyl-6-[4-methyl-5-[4-(trifluoromethyl)-2-pyridyl]-1,2,4-triazol-3-yl]-3-pyridyl]-N'-methyl-cyclopropanecarbohydrazide A47

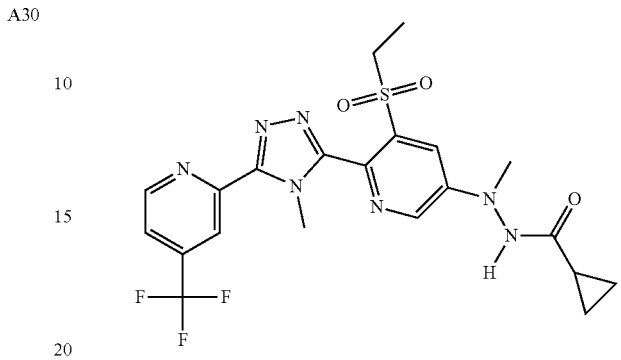

1-[5-ethylsulfonyl-6-[4-methyl-5-[4-(trifluoromethyl)-2-pyridyl]-1,2,4-triazol-3-yl]-3-pyridyl]-1-methyl-hydrazine (Prepared as descripted in Example P29, Step A to step C) (0.723 mmol, 0.319 g) was dissolved in anhydrous DMF (3 ml) under nitrogen. To it cyclopropyl carboxylic acid (0.795 mmol, 0.06 ml) was added followed by the addition of DIPEA (2.169 mmol, 0.4 ml). HATU (1.084 mmol, 412 mg) was then added to the reaction mixture and it was stirred at room temperature overnight. After the completion of the reaction it was quenched in water. Reaction mixture was diluted with EtOAc (20 ml). Organic layer was separated. Aqueous layer was further extracted with EtOAc (2×20 ml). Combined organic extract was washed with water (3×30 ml), brine, dried over sodium sulfate and concentrated to get crude product. Crude product was purified by column chromatography gradient cyclohexane+0-40% EtOAc to give N'-[5-ethylsulfonyl-6-[4-methyl-5-[4-(trifluoromethyl)-2-pyridyl]-1,2,4-triazol-3-yl]-3-pyridyl]-N'-methyl-cyclopropanecarbohydrazide (138 mg, 37%). $^1$H NMR (400 MHz, CDCl$_3$) δ ppm 0.93 (m, 2H), 1.09 (m, 2H) 1.34 (t, 3H) 1.56 (m, 1H) 3.40 (s, 3H) 3.70 (m, 2H) 3.99 (s, 3H) 7.58 (m, 1H) 7.72 (d, 1H) 8.23 (d, 1H) 8.44 (m, 1H), 8.69 (s, 1H), 8.86 (m, 1H).

Step B: N'-[5-ethylsulfonyl-6-[4-methyl-5-[4-(trifluoromethyl)-2-pyridyl]-1,2,4-triazol-3-yl]-3-pyridyl]-N,N'-dimethyl-cyclopropanecarbohydrazide A31

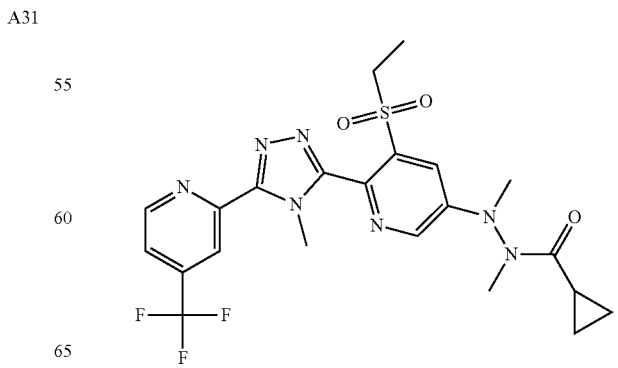

N'-[5-ethylsulfonyl-6-[4-methyl-5-[4-(trifluoromethyl)-2-pyridyl]-1,2,4-triazol-3-yl]-3-pyridyl]-N'-methyl-cyclopropanecarbohydrazide (0.2512 mmol, 0.128 g) was dissolved in N,N-dimethylacetamide (1 mL) and to it sodium hydride (0.3768 mmol, 0.01507 g) was added under nitrogen at 0° C. and reaction mixture was stirred at 0° C. for 10 mins. Iodomethane (0.5025 mmol, 0.07132 g, 0.0313 mL) was added to the reaction mixture and stirred for 2 hrs at room temperature. After the completion of reaction as monitored by TLC, it was quenched with water and diluted with EtOAc (10 ml). Organic layer was separated. Aqueous layer was further extracted with EtOAc (2×15 ml). Combined organic layer was washed with brine, dried over sodium sulfate and concentrated under vacuum to get crude product. Column purification done in CombiFlash and pure compound eluted in EtOAc to give N'-[5-ethylsulfonyl-6-[4-methyl-5-[4-(trifluoromethyl)-2-pyridyl]-1,2,4-triazol-3-yl]-3-pyridyl]-N,N'-dimethyl-cyclopropanecarbohydrazide (0.1624 mmol, 0.085 g) in 64% yield. LCMS and NMR showed product formation. To confirm N-alkylation vs O-alkylation, 13C-APT was performed. Three methyl groups came at 29 ppm, 33 ppm and 38 ppm which confirms N-alkylation as compared to O-alkylation. $^1$H NMR (400 MHz, CDCl$_3$) δ ppm 0.71-0.93 (m, 2H) 0.99-1.15 (m, 2H) 1.36 (t, 4H) 1.88-1.98 (m, 1H) 3.16 (s, 3H) 3.41 (s, 3H) 3.70-3.87 (m, 2H) 4.03 (s, 3H) 7.49-7.63 (m, 1H) 7.73 (d, 1H) 8.45 (d, 1H) 8.61-8.75 (m, 1H) 8.85 (d, 1H).

Example P30: Preparation of 5-ethylsulfonyl-6-[4-methyl-5-[4-(trifluoromethyl)-2-pyridyl]-1,2,4-triazol-3-yl]-N-(2,2,2-trifluoroethyl)pyridin-2-amine A32

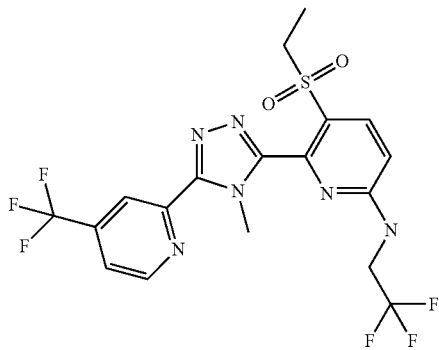

6-chloro-3-ethylsulfonyl-2-[4-methyl-5-[4-(trifluoromethyl)-2-pyridyl]-1,2,4-triazol-3-yl]pyridine (2.316 mmol, 1 g) was dissolved in anhydrous toluene (10 mL) and to it cesium carbonate (9.264 mmol, 3.02 g) was added under nitrogen atmosphere. Reaction mixture was degassed and purged with nitrogen for 15 mins. Tris(dibenzylideneacetone)dipalladium (0) (0.0463 mmol, 0.043 g), (+/-)-BINAP (0.0926 mmol, 0.0595 g) and 2,2,2-trifluoroethylammonium chloride (3.47 mmol, 0.471 g) were added to the reaction mixture and it was heated at 110° C. for 16 hours and monitored by TLC. After the completion of the reaction, it was diluted with water and compound was extracted with ethyl acetate. The combined organic extract was washed successively with water and brine, dried over Na$_2$SO$_4$ and concentrated in vacuo to get the crude product. It was purified in column chromatography gradient cyclohexane+0-80% EtOAc CombiFlash to give 5-ethylsulfonyl-6-[4-methyl-5-[4-(trifluoromethyl)-2-pyridyl]-1,2,4-triazol-3-yl]-N-(2,2,2-trifluoroethyl)pyridin-2-amine (0.675 g, 58%). $^1$H NMR (400 MHz, CDCl$_3$) δ=8.87 (d, 1H), 8.69 (s, 1H), 8.15 (d, 1H), 7.60 (d, 1H), 6.78 (d, 1H), 5.68 (t, 1H), 4.28-4.16 (m, 2H), 4.03 (s, 3H), 3.66 (q, 2H), 1.34 (t, 3H).

Example P31: Preparation of 5-ethylsulfonyl-6-[4-methyl-5-[4-(trifluoromethyl)-2-pyridyl]-1,2,4-triazol-3-yl]pyridine-3-carboxylic acid A33

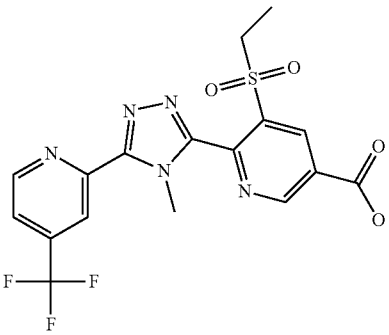

Step A: Preparation of 5-ethylsulfonyl-6-[4-methyl-5-[4-(trifluoromethyl)-2-pyridyl]-1,2,4-triazol-3-yl]pyridine-3-carbonitrile

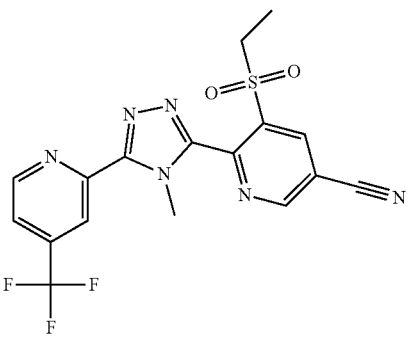 [SMILES: CCS(=O)(=O)c1cc(C#N)cnc1-c1nnc(-c2cc(C(F)(F)F)ccn2)n1C]

A 500 mL one neck flask was charged with 5-bromo-3-ethylsulfonyl-2-[4-methyl-5-[4-(trifluoromethyl)-2-pyridyl]-1,2,4-triazol-3-yl]pyridine (18.14 g, 38.09 mmol) and N,N-dimethyl acetamide (180 mL). To this solution was added Zinc dust (4.57 mmol, 0.305 g) and 1,1-bis(diphenylphosphino) ferrocene (1.52 mmol, 0.845 g) and then purged with N$_2$ gas for 25 min. Zinc cyanide (22.85 mmol, 2.77 g) and (1E,4E)-1,5-diphenylpenta-1,4-dien-3-one; palladium (0.762 mmol, 0.698 g) were successively added to the above reaction mixture and heated at 110° C. for 40 minutes. The reaction mixture was then quenched with 100 ml water and the aqueous phase was extracted with ethyl acetate (3×200 ml).

The organic phases were combined, concentrated under vacuum and purified by column chromatography gradient cyclohexane+0-30% EtOAc CombiFlash using 30% ethyl acetate-Cyclohexane to give the tittle compound in 63% yield. $^1$H NMR (400 MHz, CDCl$_3$) δ ppm 1.40-1.46 (t, 3H)

3.93-4.01 (q, 2H) 4.14 (s, 3H) 7.63 (m, 1H) 8.70 (s, 1H) 8.81 (d, 1H) 8.90 (d, 1H) 9.23 (d, 1H).

Step B: Preparation of 5-ethylsulfonyl-6-[4-methyl-5-[4-(trifluoromethyl)-2-pyridyl]-1,2,4-triazol-3-yl]pyridine-3-carboxylic acid A33

In a 100 ml round bottom flask, 5-ethylsulfonyl-6-[4-methyl-5-[4-(trifluoromethyl)-2-pyridyl]-1,2,4-triazol-3-yl]pyridine-3-carbonitrile (1.657 mmol, 0.7 g) was dissolved in HCl 32% (Conc HCl, 9 ml). The reaction mixture was heated to 60° C. for 8 h. The reaction was monitored by LCMS and TLC. The reaction mixture was then cooled to 0°-5° C., treated with NaOH 60% sol. until pH-11 (basic), extracted with 2×50 ml TBME. The water phase was acidified with Concentrated HCl to pH-4, and then allowed to cool under ice to facilitate the precipitation of the product for about 30 min. The solid was filtrated, washed with water and dried in vacuo to provide 5-ethylsulfonyl-6-[4-methyl-5-[4-(trifluoromethyl)-2-pyridyl]-1,2,4-triazol-3-yl]pyridine-3-carboxylic acid A33 (570 mg, 78%). $^1$H NMR (400 MHz, DMSO-d6) δ ppm 1.23 (t, 3H) 3.82 (q, 2H) 3.93 (s, 3H) 7.98 (d, 1H) 8.51 (s, 1H) 8.83 (d, 1H) 9.06 (d, 1H) 9.50 (d, 1H) 13.94 (s, 1H).

Example 32: Preparation of 5-ethylsulfonyl-6-[4-methyl-5-[4-(trifluoromethyl)-2-pyridyl]-1,2,4-triazol-3-yl]pyridine-2-carboxylic Acid A34

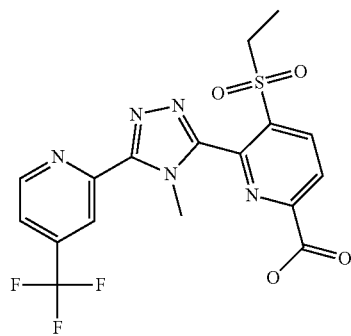

A34

Step A: Preparation of 5-ethylsulfonyl-6-[4-methyl-5-[4-(trifluoromethyl)-2-pyridyl]-1,2,4-triazol-3-yl]pyridine-2-carbonitrile

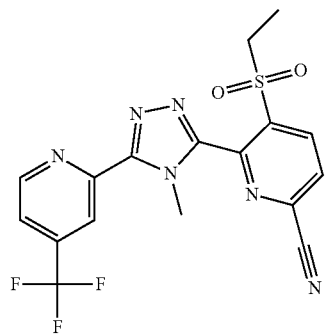 [SMILES: CCS(=O)(=O)c1ccc(C#N)nc1-c1nnc(-c2cc(C(F)(F)F)ccn2)n1C]

6-chloro-3-ethylsulfonyl-2-[4-methyl-5-[4-(trifluoromethyl)-2-pyridyl]-1,2,4-triazol-3-yl]pyridine (8 g, 18.5262 mmol) was dissolved in DMSO in a single neck flask. To this reaction mixture was added 1,4-diazabicyclo[2.2.2]octane (0.9263 mmol, 0.102 mL) at 0° C. under nitrogen atmosphere and the mixture was stirred for 10 mins. A solution of sodium cyanide (22.2315 mmol, 1.0895 g) in water (5 mL) was added to the above reaction mixture and heated at 50° C. for 3 hrs. The reaction mixture was quenched with water and diluted with EtOAc (20 ml). The organic layer was separated and aqueous layer was extracted with EtOAc (2×10 ml). The organic phases were combined, washed with brine, dried over sodium sulfate and concentrated to 5-ethylsulfonyl-6-[4-methyl-5-[4-(trifluoromethyl)-2-pyridyl]-1,2,4-triazol-3-yl]pyridine-2-carbonitrile in 63% yield. $^1$H NMR (400 MHz, CDCl$_3$) δ ppm 1.38 (t, 3H), 3.92 (q, 2H) 4.13 (s, 3H) 7.62 (m, 1H) 8.07 (d, 1H) 8.63-8.73 (m, 2H) 8.87 (m, 1H)

Step B: Preparation of 5-ethylsulfonyl-6-[4-methyl-5-[4-(trifluoromethyl)-2-pyridyl]-1,2,4-triazol-3-yl]pyridine-2-carboxylic Acid A34

In single neck round bottom flask, 5-ethylsulfonyl-6-[4-methyl-5-[4-(trifluoromethyl)-2-pyridyl]-1,2,4-triazol-3-yl]pyridine-2-carbonitrile (5 g, 11.84 mmol) was dissolved in hydrogen chloride (30 mL, 35% in water) and the reaction mixture was stirred at 70° C. for 13 hours. After this, the reaction mixture was cooled with ice and treated with NaOH (10% solution) to bring to the pH 10 and washed with tert-butyl methyl ether. Aqueous layer was acidified (pH=3), thus obtained solid was filtered, washed with water (20 ml), diethyl ether (30 ml), and finally azeotrope evaporated with toluene to provide 5-ethylsulfonyl-6-[4-methyl-5-[4-(trifluoromethyl)-2-pyridyl]-1,2,4-triazol-3-yl]pyridine-2-carboxylic acid (4 g, 80%). $^1$H NMR (400 MHz, DMSO-d6) δ ppm 1.21 (t, 3H) 3.76 (q, 2H) 3.91 (s, 3H) 7.98 (d, 1H) 8.47 (m, 2H) 8.69 (m, 1H) 9.05 (m, 1H).

Example 33: Preparation of 5-ethylsulfonyl-6-[4-methyl-5-[4-(trifluoromethyl)-2-pyridyl]-1,2,4-triazol-3-yl]pyridin-3-amine A35

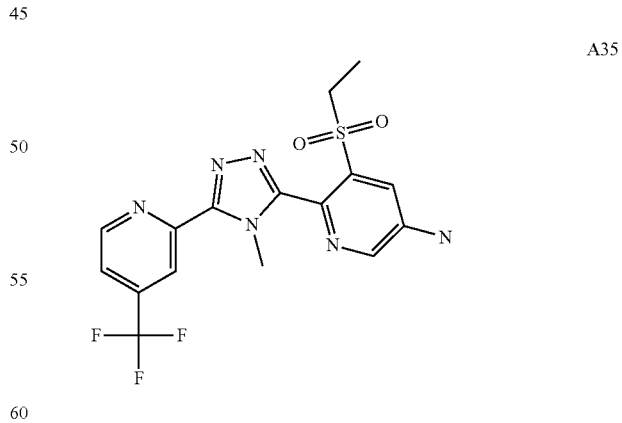

A35

5-bromo-3-ethylsulfonyl-2-[4-methyl-5-[4-(trifluoromethyl)-2-pyridyl]-1,2,4-triazol-3-yl]pyridine (Prepared as described in Example P6, Step A to step B) (25 g, 52.5 mmol) was dissolved in 250 ml of 1,4-dioxane and the mixture was degassed by bubbling nitrogen. Cesium carbonate (24.0 g, 73.5 mmol), tert-butyl carbonate (7.38 g, 63.0 mmol) and Pd(OAc)$_2$ (0.71 g, 3.15 mmol) were added and reaction mixture degassed for 15 min. X-Phos (4.59 g, 9.45 mmol) was added and the reaction mixture was degassed for 15 min. The reaction mixture was heated to 100° C. for 14 h and filtered through celite bed. The celite bed was washed with 1,4-dioxane and combined organic layer concentrated under reduced pressure. The residue was added in parts to 4 M HCl in Dioxane (360 mL) and stirred for 16 h a 24° C. and resulting suspension filtered. The residue was dissolved in water and to it was slowly added solid sodium bicarbonate pH 8. The aqueous layer was extracted with CH$_2$Cl$_2$ (3×100 mL) and the combined organic layer evaporated under reduced pressure to provide 5-ethylsulfonyl-6-[4-methyl-5-[4-(trifluoromethyl)-2-pyridyl]-1,2,4-triazol-3-yl]pyridin-3-amine (13.6 g, 62%). 1H NMR (400 MHz, DMSO-d6) ppm 1.17 (t, 3H) 3.64 (d, 2H) 3.81 (s, 3H), 6.51 (s, 2H), 7.58 (d, 1H) 7.94 (d, 1H) 8.31 (d, 1H) 8.47 (s, 1H) 9.03 (d, 1H)

Example 34: Preparation of 3-chloro-5-ethylsulfonyl-6-[4-methyl-5-[4-(trifluoromethyl)-2-pyridyl]-1,2,4-triazol-3-yl]pyridin-2-amine A42

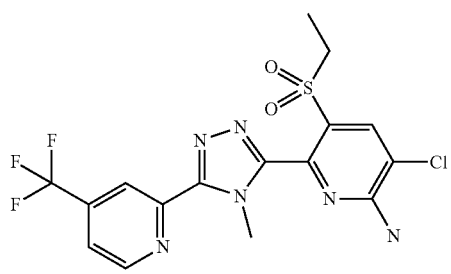 [SMILES: CCS(=O)(=O)c1cc(Cl)c(N)nc1-c1nnc(-c2cc(C(F)(F)F)ccn2)n1C]

200 mg of 5-ethylsulfonyl-6-[4-methyl-5-[4-(trifluoromethyl)-2-pyridyl]-1,2,4-triazol-3-yl]pyridin-2-amine A36 (0.49 mmol) was dissolved in 5 ml of acetonitrile and the mixture was cooled with an ice bath. N-Chlorosuccinimide (67.5 mg, 0.051 mmol) was added and the reaction was stirred at 0° C. for 30 min. The reaction was warmed up to room temperature, then heated to 50° C. and stirred over night at this temperature. The mixture was poured into cold water. The residue solid was separated by filtration, washed with cold water, dissolved in dichloromethane, dried over anhydrous magnesium sulfate, filtered and evaporated under reduced pressure. Then, the resulting solid was stirred in cold diethyl ether, filtered and dried in vacuum to give the title compound in 48% yield. MP: 215-16° C.

Example 35: Preparation of cyclopropyl-[[5-ethylsulfonyl-6-[4-methyl-5-[4-(trifluoromethyl)-2-pyridyl]-1,2,4-triazol-3-yl]-3-pyridyl]imino]-methyl-oxido-λ4-sulfanylidene A46

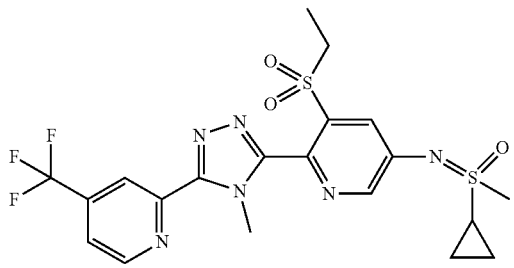 [SMILES: CCS(=O)(=O)c1cc(N=S(C)(=O)C2CC2)cnc1-c1nnc(-c2cc(C(F)(F)F)ccn2)n1C]

A microwave vial was charged with 5-bromo-3-ethylsulfonyl-2-[4-methyl-5-[4-(trifluoromethyl)-2-pyridyl]-1,2,4-triazol-3-yl]pyridine (0.6299 mmol, 0.3 g), cyclopropyl(methyl) sulfoximine (0.693 mmol, 0.0826 g), dicesium carbonic acid (1.26 mmol, 0.413 g) and (5-diphenylphosphanyl-9,9-dimethyl-xanthen-4-yl)-diphenyl-phosphane (0.126 mmol, 0.0751 g) in 1,4-dioxane (6.0 mL) and then degassed, purged with nitrogen for 10 min. To this was then added (1E,4E)-1,5-diphenylpenta-1,4-dien-3-one palladium (0.063 mmol, 0.0577 g) and reaction mixture was heated in microwave at 110° C. for 60 min, the reaction was diluted with water (10 ml) and extracted with ethyl acetate (3×30 ml). The combined organic layer was dried over sodium sulfate, filtered and concentrated under reduced pressure. crude product was purified by CombiFlash (silica gel, 70% EA-cyclohexane) to afford cyclopropyl-[[5-ethylsulfonyl-6-[4-methyl-5-[4-(trifluoromethyl)-2-pyridyl]-1,2,4-triazol-3-yl]-3-pyridyl]imino]-methyloxido-λ4-sulfanylidene (0.292 mmol, 0.15 g, 46%)[1] H NMR (400 MHz, CDCl$_3$) δ ppm 8.85 (d, 1H), 8.70-8.66 (m, 2H), 8.08 (d, 1H), 7.59-7.55 (m, 1H), 4.02 (s, 3H), 3.79-3.68 (m, 2H), 3.27 (s, 3H), 2.67-2.61 (m, 1H), 1.59-1.55 (m, 1H), 1.39-1.33 (t, 3H), 1.32-1.28 (m, 2H), 1.23-1.16 (m, 1H).

TABLE P1

Examples of compounds of formula (I)

| Compound No. | Structures | Analytic Method |
|---|---|---|
| A1 | 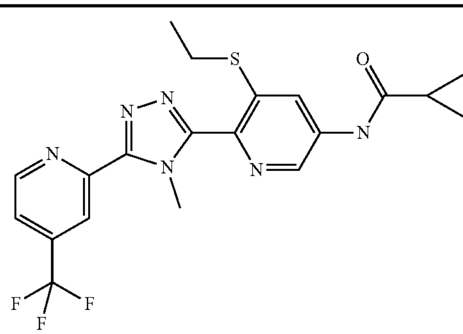 | See experimental part above |

TABLE P1-continued

Examples of compounds of formula (I)

| Compound No. | Structures | Analytic Method |
|---|---|---|
| A2 | 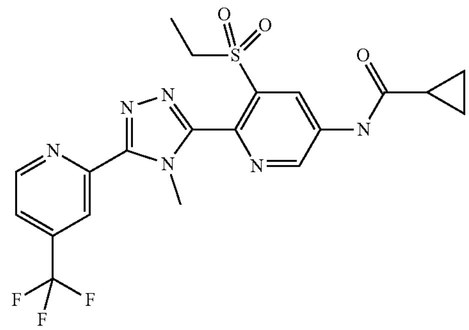 [SMILES: CCS(=O)(=O)c1cc(NC(=O)C2CC2)cnc1-c1nnc(-c2cc(C(F)(F)F)ccn2)n1C] | See experimental part above |
| A3 | 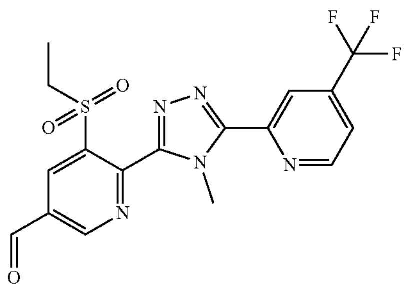 [SMILES: CCS(=O)(=O)c1cc(C=O)cnc1-c1nnc(-c2cc(C(F)(F)F)ccn2)n1C] | See experimental part above |
| A4 | 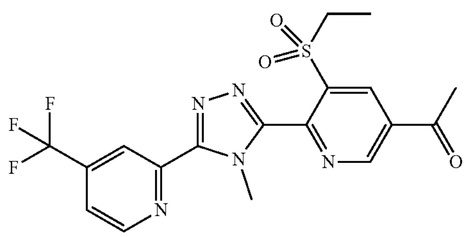 [SMILES: CCS(=O)(=O)c1cc(C(C)=O)cnc1-c1nnc(-c2cc(C(F)(F)F)ccn2)n1C] | See experimental part above |
| A5 | 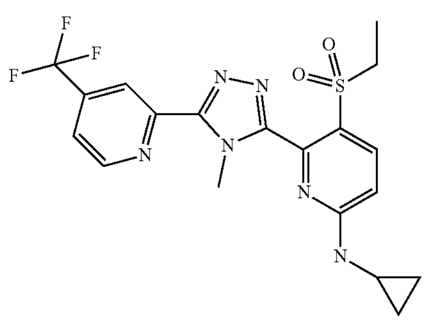 [SMILES: CCS(=O)(=O)c1ccc(NC2CC2)nc1-c1nnc(-c2cc(C(F)(F)F)ccn2)n1C] | See experimental part above |
| A6 | 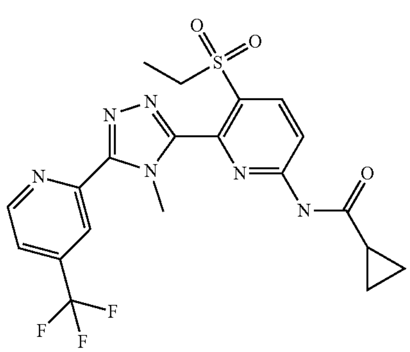 [SMILES: CCS(=O)(=O)c1ccc(NC(=O)C2CC2)nc1-c1nnc(-c2cc(C(F)(F)F)ccn2)n1C] | See experimental part above |

TABLE P1-continued

Examples of compounds of formula (I)

| Compound No. | Structures | Analytic Method |
|---|---|---|
| A7 | 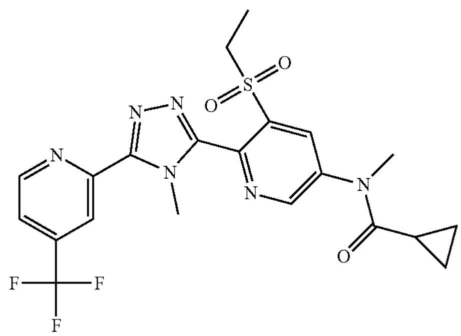 [SMILES: CCS(=O)(=O)c1cc(N(C)C(=O)C2CC2)cnc1-c1nnc(-c2cc(C(F)(F)F)ccn2)n1C] | See experimental part above |
| A8 | 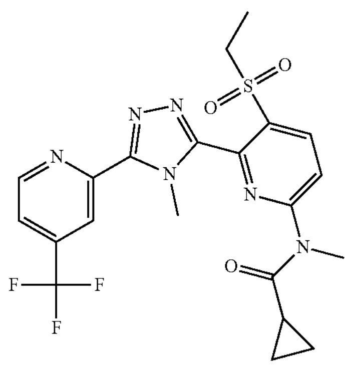 [SMILES: CCS(=O)(=O)c1ccc(N(C)C(=O)C2CC2)nc1-c1nnc(-c2cc(C(F)(F)F)ccn2)n1C] | See experimental part above |
| A9 | 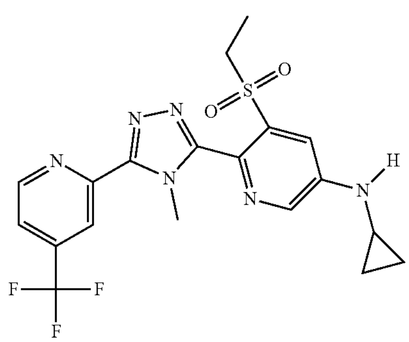 [SMILES: CCS(=O)(=O)c1cc(NC2CC2)cnc1-c1nnc(-c2cc(C(F)(F)F)ccn2)n1C] | See experimental part above |
| A10 | 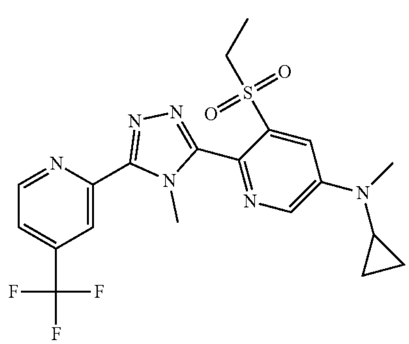 [SMILES: CCS(=O)(=O)c1cc(N(C)C2CC2)cnc1-c1nnc(-c2cc(C(F)(F)F)ccn2)n1C] | See experimental part above |

TABLE P1-continued

Examples of compounds of formula (I)

| Compound No. | Structures | Analytic Method |
|---|---|---|
| A11 | 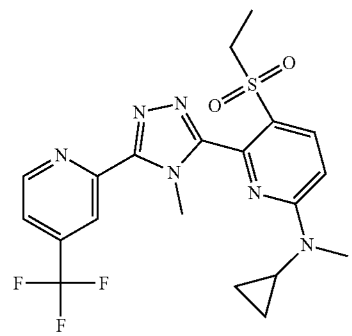 [SMILES: CCS(=O)(=O)c1ccc(N(C)C2CC2)nc1-c1nnc(-c2cc(C(F)(F)F)ccn2)n1C] | See experimental part above |
| A12 | 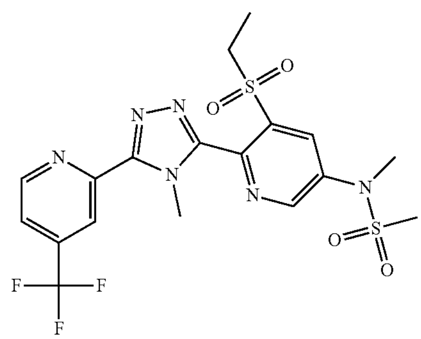 [SMILES: CCS(=O)(=O)c1cc(N(C)S(C)(=O)=O)cnc1-c1nnc(-c2cc(C(F)(F)F)ccn2)n1C] | See experimental part above |
| A13 | 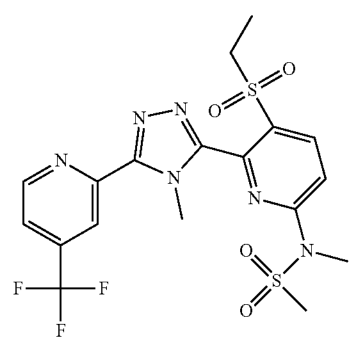 [SMILES: CCS(=O)(=O)c1ccc(N(C)S(C)(=O)=O)nc1-c1nnc(-c2cc(C(F)(F)F)ccn2)n1C] | See experimental part above |
| A14 | 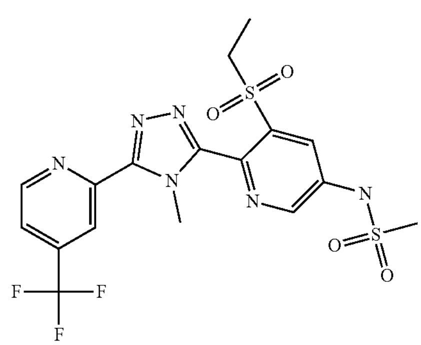 [SMILES: CCS(=O)(=O)c1cc(NS(C)(=O)=O)cnc1-c1nnc(-c2cc(C(F)(F)F)ccn2)n1C] | See experimental part above |

TABLE P1-continued

Examples of compounds of formula (I)

| Compound No. | Structures | Analytic Method |
|---|---|---|
| A15 | 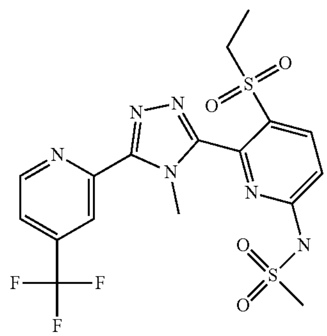 [SMILES: CCS(=O)(=O)c1ccc(NS(C)(=O)=O)nc1-c1nnc(-c2cc(C(F)(F)F)ccn2)n1C] | See experimental part above |
| A16 | 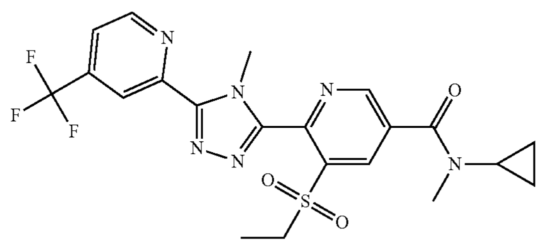 [SMILES: CCS(=O)(=O)c1cc(C(=O)N(C)C2CC2)cnc1-c1nnc(-c2cc(C(F)(F)F)ccn2)n1C] | See experimental part above |
| A17 | 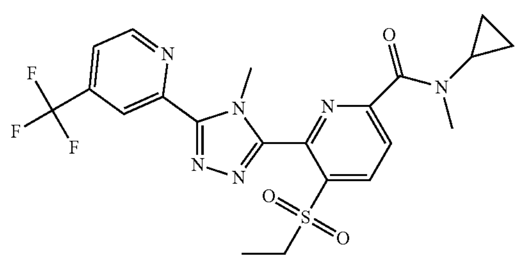 [SMILES: CCS(=O)(=O)c1ccc(C(=O)N(C)C2CC2)nc1-c1nnc(-c2cc(C(F)(F)F)ccn2)n1C] | See experimental part above |
| A18 | 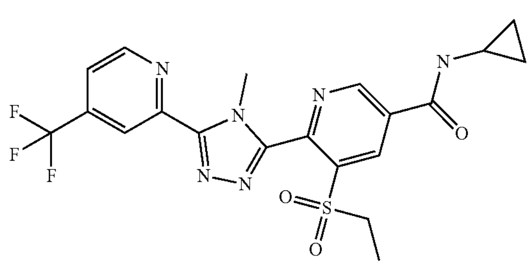 [SMILES: CCS(=O)(=O)c1cc(C(=O)NC2CC2)cnc1-c1nnc(-c2cc(C(F)(F)F)ccn2)n1C] | See experimental part above |
| A19 | 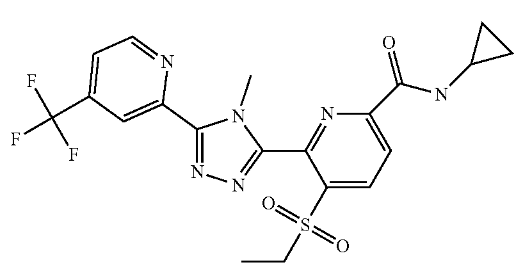 [SMILES: CCS(=O)(=O)c1ccc(C(=O)NC2CC2)nc1-c1nnc(-c2cc(C(F)(F)F)ccn2)n1C] | See experimental part above |

TABLE P1-continued

Examples of compounds of formula (I)

| Compound No. | Structures | Analytic Method |
|---|---|---|
| A20 | 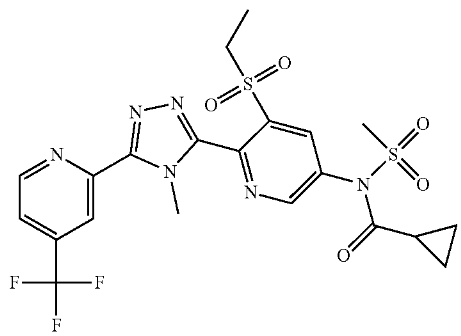 [SMILES: CCS(=O)(=O)c1cc(N(C(=O)C2CC2)S(C)(=O)=O)cnc1-c1nnc(-c2cc(C(F)(F)F)ccn2)n1C] | See experimental part above |
| A21 | 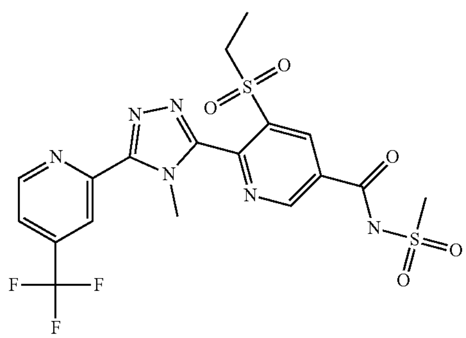 [SMILES: CCS(=O)(=O)c1cc(C(=O)NS(C)(=O)=O)cnc1-c1nnc(-c2cc(C(F)(F)F)ccn2)n1C] | See experimental part above |
| A22 | 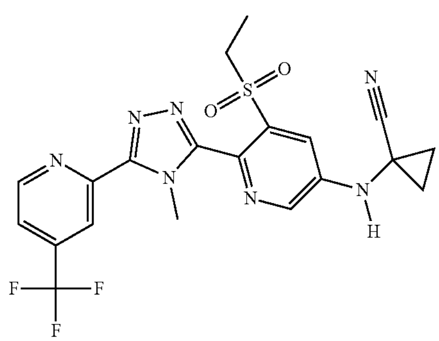 [SMILES: CCS(=O)(=O)c1cc(NC2(C#N)CC2)cnc1-c1nnc(-c2cc(C(F)(F)F)ccn2)n1C] | See experimental part above |
| A23 | 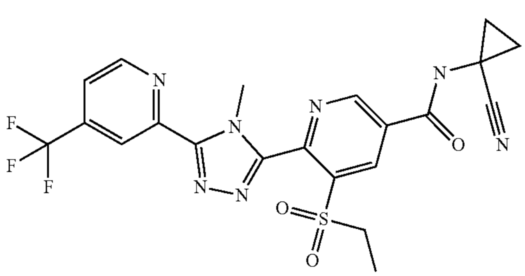 [SMILES: CCS(=O)(=O)c1cc(C(=O)NC2(C#N)CC2)cnc1-c1nnc(-c2cc(C(F)(F)F)ccn2)n1C] | See experimental part above |

TABLE P1-continued

Examples of compounds of formula (I)

| Compound No. | Structures | Analytic Method |
|---|---|---|
| A24 | 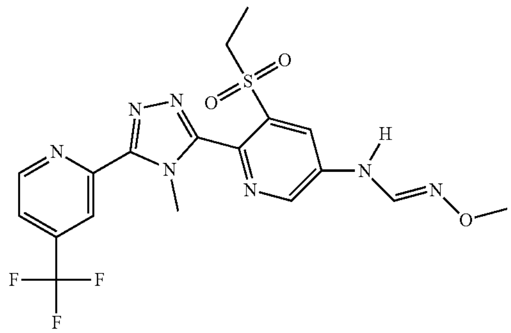 [SMILES: CCS(=O)(=O)c1cc(N/C=N/OC)cnc1-c1nnc(-c2cc(C(F)(F)F)ccn2)n1C] | See experimental part above |
| A25 | 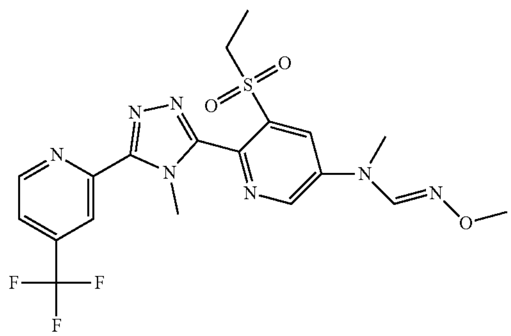 [SMILES: CCS(=O)(=O)c1cc(N(C)/C=N/OC)cnc1-c1nnc(-c2cc(C(F)(F)F)ccn2)n1C] | See experimental part above |
| A26 | 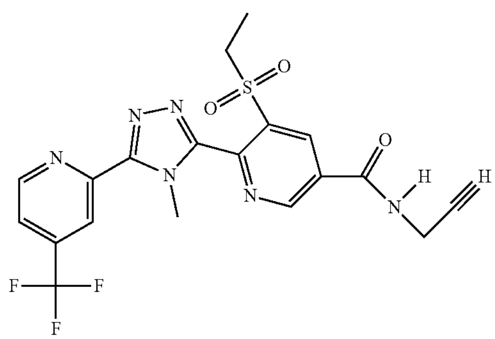 | See experimental part above |
| A27 | 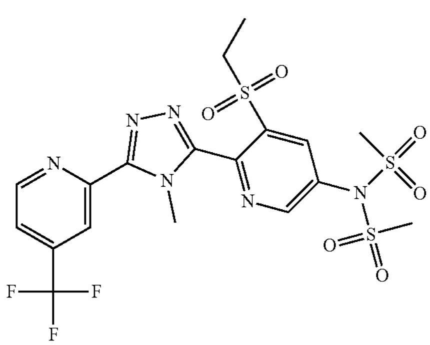 [SMILES: CCS(=O)(=O)c1cc(N(S(C)(=O)=O)S(C)(=O)=O)cnc1-c1nnc(-c2cc(C(F)(F)F)ccn2)n1C] | See experimental part above |

TABLE P1-continued

Examples of compounds of formula (I)

| Compound No. | Structures | Analytic Method |
|---|---|---|
| A28 | 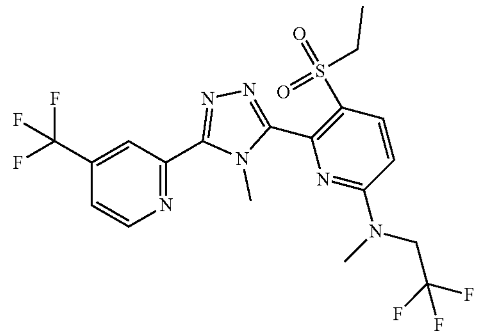 [SMILES: CCS(=O)(=O)c1ccc(N(C)CC(F)(F)F)nc1-c1nnc(-c2cc(C(F)(F)F)ccn2)n1C] | See experimental part above |
| A29 | 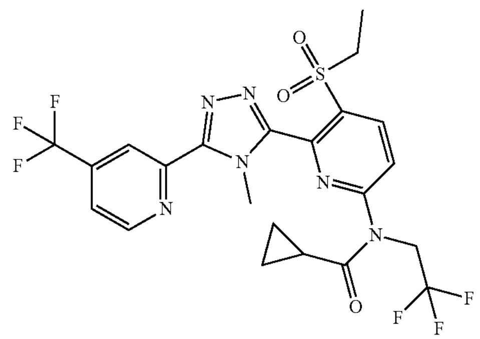 [SMILES: CCS(=O)(=O)c1ccc(N(CC(F)(F)F)C(=O)C2CC2)nc1-c1nnc(-c2cc(C(F)(F)F)ccn2)n1C] | See experimental part above |
| A30 | 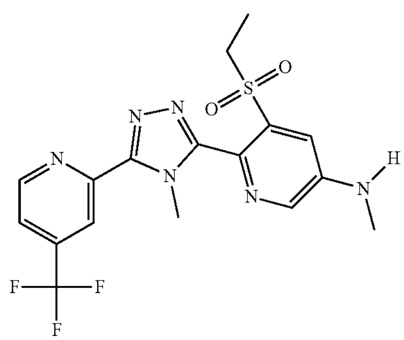 [SMILES: CCS(=O)(=O)c1cc(NC)cnc1-c1nnc(-c2cc(C(F)(F)F)ccn2)n1C] | See experimental part above |
| A31 | 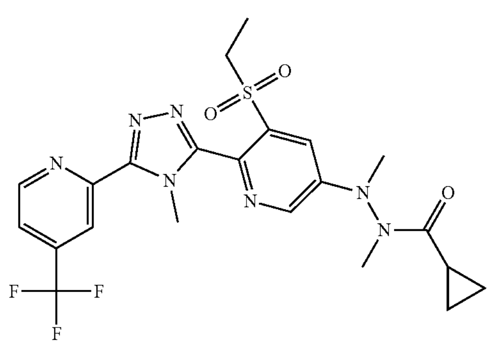 [SMILES: CCS(=O)(=O)c1cc(N(C)N(C)C(=O)C2CC2)cnc1-c1nnc(-c2cc(C(F)(F)F)ccn2)n1C] | See experimental part above |

TABLE P1-continued

Examples of compounds of formula (I)

| Compound No. | Structures | Analytic Method |
|---|---|---|
| A32 | 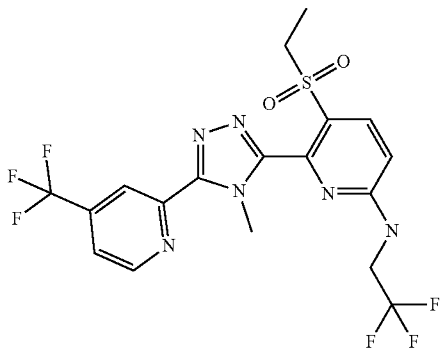 [SMILES: CCS(=O)(=O)c1ccc(NCC(F)(F)F)nc1-c1nnc(-c2cc(C(F)(F)F)ccn2)n1C] | See experimental part above |
| A33 | 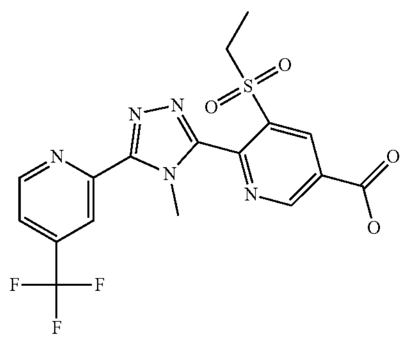 [SMILES: CCS(=O)(=O)c1cc(C(=O)O)cnc1-c1nnc(-c2cc(C(F)(F)F)ccn2)n1C] | See experimental part above |
| A34 | 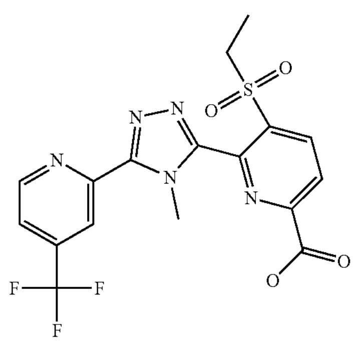 [SMILES: CCS(=O)(=O)c1ccc(C(=O)O)nc1-c1nnc(-c2cc(C(F)(F)F)ccn2)n1C] | See experimental part above |
| A35 | 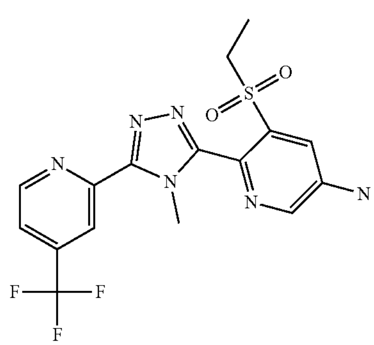 [SMILES: CCS(=O)(=O)c1cc(N)cnc1-c1nnc(-c2cc(C(F)(F)F)ccn2)n1C] | See experimental part above |

TABLE P1-continued

Examples of compounds of formula (I)

| Compound No. | Structures | Analytic Method |
|---|---|---|
| A36 | 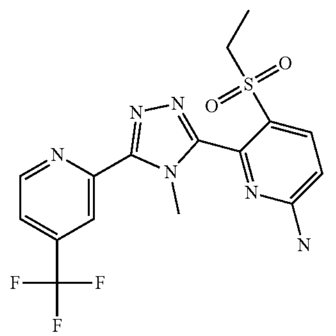 [SMILES: CCS(=O)(=O)c1ccc(N)nc1-c1nnc(-c2cc(C(F)(F)F)ccn2)n1C] | See experimental part above |
| A37 | 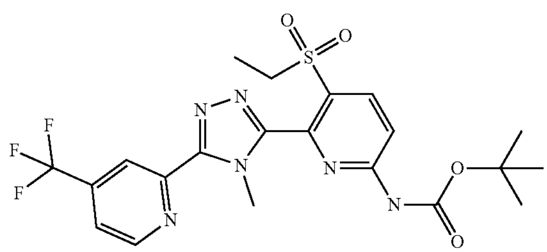 [SMILES: CCS(=O)(=O)c1ccc(NC(=O)OC(C)(C)C)nc1-c1nnc(-c2cc(C(F)(F)F)ccn2)n1C] | See experimental part above |
| A38 | 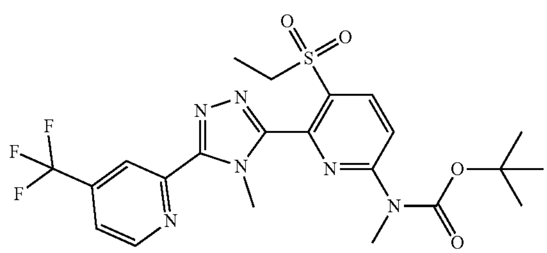 [SMILES: CCS(=O)(=O)c1ccc(N(C)C(=O)OC(C)(C)C)nc1-c1nnc(-c2cc(C(F)(F)F)ccn2)n1C] | See experimental part above |
| A39 | 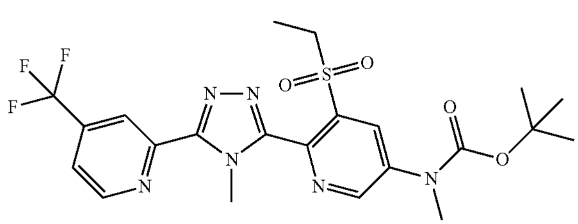 [SMILES: CCS(=O)(=O)c1cc(N(C)C(=O)OC(C)(C)C)cnc1-c1nnc(-c2cc(C(F)(F)F)ccn2)n1C] | See experimental part above |
| A40 | 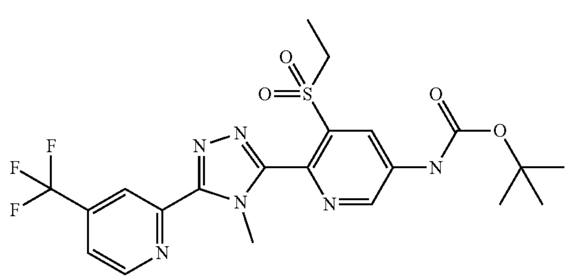 [SMILES: CCS(=O)(=O)c1cc(NC(=O)OC(C)(C)C)cnc1-c1nnc(-c2cc(C(F)(F)F)ccn2)n1C] | See experimental part above |

TABLE P1-continued

Examples of compounds of formula (I)

| Compound No. | Structures | Analytic Method |
|---|---|---|
| A41 | 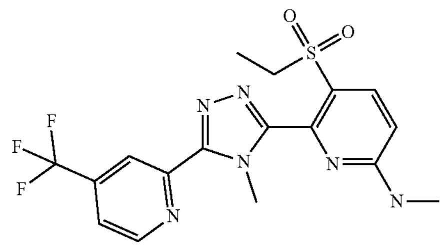 [SMILES: CCS(=O)(=O)c1ccc(NC)nc1-c1nnc(-c2cc(C(F)(F)F)ccn2)n1C] | See experimental part above |
| A42 | 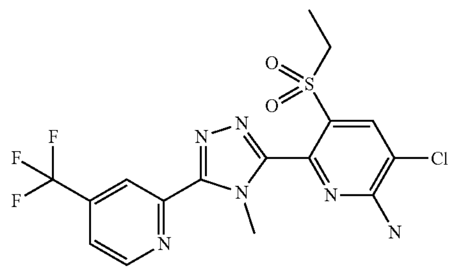 [SMILES: CCS(=O)(=O)c1cc(Cl)c(N)nc1-c1nnc(-c2cc(C(F)(F)F)ccn2)n1C] | See experimental part above |
| A43 | 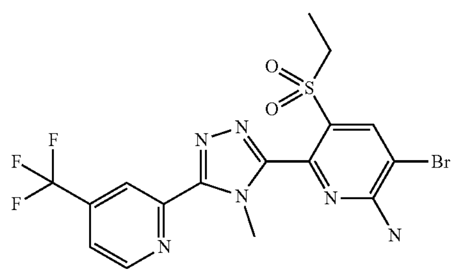 [SMILES: CCS(=O)(=O)c1cc(Br)c(N)nc1-c1nnc(-c2cc(C(F)(F)F)ccn2)n1C] | A43 was synthesised using a similar protocol as described for A42 using NBS. MP: 210-211° C. |
| A44 | 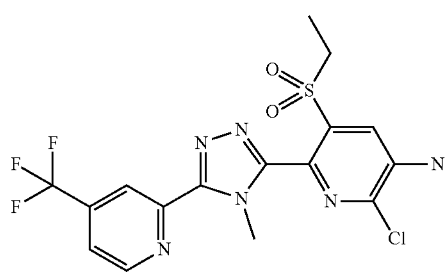 [SMILES: CCS(=O)(=O)c1cc(N)c(Cl)nc1-c1nnc(-c2cc(C(F)(F)F)ccn2)n1C] | A44 was synthesised using a similar protocol as described for A42 using A35. MP: 258-260° C. |
| A45 | 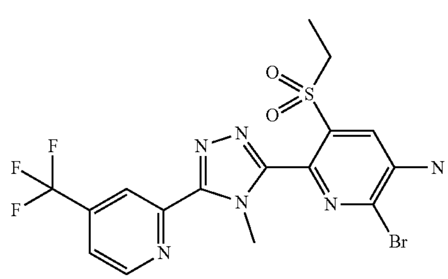 [SMILES: CCS(=O)(=O)c1cc(N)c(Br)nc1-c1nnc(-c2cc(C(F)(F)F)ccn2)n1C] | A45 was synthesised using a similar protocol as described for A42 using NBS and A35. MP: 251-253° C. |

TABLE P1-continued

Examples of compounds of formula (I)

| Compound No. | Structures | Analytic Method |
| --- | --- | --- |
| A46 | 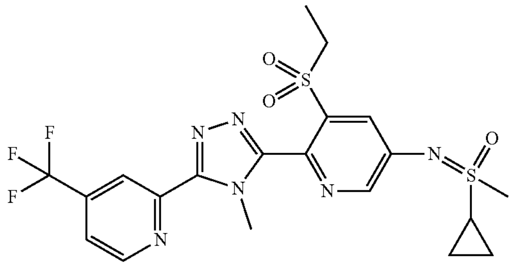 [SMILES: CCS(=O)(=O)c1cc(N=S(C)(=O)C2CC2)cnc1-c1nnc(-c2cc(C(F)(F)F)ccn2)n1C] | See experimental part above |
| A47 | 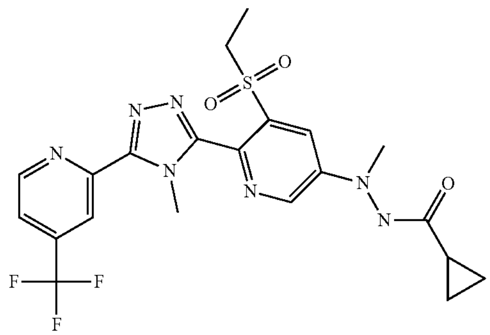 [SMILES: CCS(=O)(=O)c1cc(N(C)NC(=O)C2CC2)cnc1-c1nnc(-c2cc(C(F)(F)F)ccn2)n1C] | See experimental part above |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 42 and P of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacry-pyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX,

*Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure B$_1$ (839)+TX, trimedlure B$_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+

TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin

[CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloroprallethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+

TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzo-lar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihyd roxy-4,6a, 12b-trimethyl-11-oxo-9-(3-pyridinyl)-2H,11Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, Colletotrichum acutatum+TX, Coniothyrium minitans (Cotans WG®)+TX, Coniothyrium spp.+TX, Cryptococcus albidus (YIELDPLUS®)+TX, Cryptococcus humicola+TX, Cryptococcus infirmo-miniatus+TX, Cryptococcus laurentii+TX, Cryptophlebia leucotreta granulovirus (Cryptex®)+TX, Cupriavidus campinensis+TX, Cydia pomonella granulovirus (CYD-X®)+TX, Cydia pomonella granulovirus (Madex®+TX, Madex Plus®+TX, Madex Max/Carpovirusine®)+TX, Cylindrobasidium laeve (Stumpout®)+TX, Cylindrocladium+TX, Debaryomyces hansenii+TX, Drechslera hawaiinensis+TX, Enterobacter cloacae+TX, Enterobacteriaceae+TX, Entomophtora virulenta (Vektor®)+TX, Epicoccum nigrum+TX, Epicoccum purpurascens+TX, Epicoccum spp.+TX, Filobasidium floriforme+TX, Fusarium acuminatum+TX, Fusarium chlamydosporum+TX, Fusarium oxysporum (Fusaclean®/Biofox C®)+TX, Fusarium proliferatum+TX, Fusarium spp.+TX, Galactomyces geotrichum+TX, Gliocladium catenulatum (Primastop®+TX, Prestop®)+TX, Gliocladium roseum+TX, Gliocladium spp. (SoilGard®)+TX, Gliocladium virens (Soilgard®)+TX, Granulovirus (Granupom®)+TX, Halobacillus halophilus+TX, Halobacillus litoralis+TX, Halobacillus trueperi+TX, Halomonas spp.+TX, Halomonas subglaciescola+TX, Halovibrio variabilis+TX, Hanseniaspora uvarum+TX, Helicoverpa armigera nucleopolyhedrovirus (Helicovex®)+TX, Helicoverpa zea nuclear polyhedrosis virus (Gemstar®)+TX, Isoflavone-formononetin (Myconate®)+TX, Kloeckera apiculata+TX, Kloeckera spp.+TX, Lagenidium giganteum (Laginex®)+TX, Lecanicillium longisporum (Vertiblast®)+TX, Lecanicillium muscarium (Vertikil®)+TX, Lymantria Dispar nucleopolyhedrosis virus (Disparvirus®)+TX, Marinococcus halophilus+TX, Meira geulakonigii+TX, Metarhizium anisopliae (Met52®)+TX, Metarhizium anisopliae (Destruxin WP®)+TX, Metschnikowia fruticola (Shemer®)+TX, Metschnikowia pulcherrima+TX, Microdochium dimerum (Antibot®)+TX, Micromonospora coerulea+TX, Microsphaeropsis ochracea+TX, Muscodor albus 620 (Muscudor®)+TX, Muscodor roseus strain A3-5+TX, Mycorrhizae spp. (AMykor®+TX, Root Maximizer®)+TX, Myrothecium verrucaria strain AARC-0255 (DiTera®)+TX, BROS PLUS®+TX, Ophiostoma piliferum strain D97 (Sylvanex®)+TX, Paecilomyces farinosus+TX, Paecilomyces fumosoroseus (PFR-97®+TX, PreFeRal®)+TX, Paecilomyces linacinus (Biostat WP®)+TX, Paecilomyces lilacinus strain 251 (MeloCon WG®)+TX, Paenibacillus polymyxa+TX, Pantoea agglomerans (BlightBan C9-1®)+TX, Pantoea spp.+TX, Pasteuria spp. (Econem®)+TX, Pasteuria nishizawae+TX, Penicillium aurantiogriseum+TX, Penicillium billai (Jumpstart®+TX, TagTeam®)+TX, Penicillium brevicompactum+TX, Penicillium frequentans+TX, Penicillium griseofulvum+TX, Penicillium purpurogenum+TX, Penicillium spp.+TX, Penicillium viridicatum+TX, Phlebiopsis gigantean (Rotstop®)+TX, phosphate solubilizing bacteria (Phosphomeal®)+TX, Phytophthora cryptogea+TX, Phytophthora palmivora (Devine®)+TX, Pichia anomala+TX, Pichia guilermondii+TX, Pichia membranaefaciens+TX, Pichia onychis+TX, Pichia stipites+TX, Pseudomonas aeruginosa+TX, Pseudomonas aureofasciens (Spot-Less Biofungicide®)+TX, Pseudomonas cepacia+TX, Pseudomonas chlororaphis (AtEze®)+TX, Pseudomonas corrugate+TX, Pseudomonas fluorescens strain A506 (BlightBan A506®)+TX, Pseudomonas putida+TX, Pseudomonas reactans+TX, Pseudomonas spp.+TX, Pseudomonas syringae (Bio-Save®)+TX, Pseudomonas viridiflava+TX, Pseudomons fluorescens (Zequanox®)+TX, Pseudozyma flocculosa strain PF-A22 UL (Sporodex L®)+TX, Puccinia canaliculata+TX, Puccinia thlaspeos (Wood Warrior®)+TX, Pythium paroecandrum+TX, Pythium oligandrum (Polygandron®+TX, Polyversum®)+TX, Pythium periplocum+TX, Rhanella aquatilis+TX, Rhanella spp.+TX, Rhizobia (Dormal®+TX, Vault®)+TX, Rhizoctonia+TX, Rhodococcus globerulus strain AQ719+TX, Rhodosporidium diobovatum+TX, Rhodosporidium toruloides+TX, Rhodotorula spp.+TX, Rhodotorula glutinis+TX, Rhodotorula graminis+TX, Rhodotorula mucilagnosa+TX, Rhodotorula rubra+TX, Saccharomyces cerevisiae+TX, Salinococcus roseus+TX, Sclerotinia minor+TX, Sclerotinia minor (SARRITOR®)+TX, Scytalidium spp.+TX, Scytalidium uredinicola+TX, Spodoptera exigua nuclear polyhedrosis virus (Spod-X®+TX, Spexit®)+TX, Serratia marcescens+TX, Serratia plymuthica+TX, Serratia spp.+TX, Sordaria fimicola+TX, Spodoptera littoralis nucleopolyhedrovirus (Littovir)+TX, Sporobolomyces roseus+TX, Stenotrophomonas maltophilia+TX, Streptomyces ahygroscopicus+TX, Streptomyces albaduncus+TX, Streptomyces exfoliates+TX, Streptomyces galbus+TX, Streptomyces griseoplanus+TX, Streptomyces griseoviridis (Mycostop®)+TX, Streptomyces lydicus (Actinovate®)+TX, Streptomyces lydicus WYEC-108 (ActinoGrow®)+TX, Streptomyces violaceus+TX, Tilletiopsis minor+TX, Tilletiopsis spp.+TX, Trichoderma asperellum (T34 Biocontrol®)+TX, Trichoderma gamsii (Tenet®)+TX, Trichoderma atroviride (Plantmate®)+TX, Trichoderma hamatum TH 382+TX, Trichoderma harzianum rifai (Mycostar®)+TX, Trichoderma harzianum T-22 (Trianum-P®+TX, PlantShield HC®+TX, RootShield®+TX, Trianum-G®)+TX, Trichoderma harzianum T-39 (Trichodex®)+TX, Trichoderma inhamatum+TX, Trichoderma koningii+TX, Trichoderma spp. LC 52 (Sentinel®)+TX, Trichoderma lignorum+TX, Trichoderma longibrachiatum+TX, Trichoderma polysporum (Binab T®)+TX, Trichoderma taxi+TX, Trichoderma virens+TX, Trichoderma virens (formerly Gliocladium virens GL-21) (SoilGuard®)+TX, Trichoderma viride+TX, Trichoderma viride strain ICC 080 (Remedier®)+TX, Trichosporon pullulans+TX, Trichosporon spp.+TX, Trichothecium spp.+TX, Trichothecium roseum+TX, Typhula phacorrhiza strain 94670+TX, Typhula phacorrhiza strain 94671+TX, Ulocladium atrum+TX, Ulocladium oudemansii (Botry-Zen®)+TX, Ustilago maydis+TX, various bacteria and supplementary micronutrients (Natural II®)+TX, various fungi (Millennium Microbes®)+TX, Verticillium chlamydosporium+TX, Verticillium lecanii (Mycotal®+TX, Vertalec®)+TX, Vip3Aa20 (VIPtera®)+TX, Virgibacillus marismortui+TX, Xanthomonas campestris pv. Poae (Camperico®)+TX, Xenorhabdus bovienii+TX, Xenorhabdus nematophilus; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, Chenopodium ambrosioides near ambrosioides (Requiem®)+TX, Chrysanthemum extract (Crisant®)+TX, extract of neem oil (Trilogy®)+TX, essentials oils of Labiatae (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, Nepeta cataria (Catnip oil)+TX, Nepeta catarina+TX, nicotine+TX, oregano oil (MossBuster®)+TX, Pedaliaceae oil (Nematon®)+TX, pyrethrum+TX, Quillaja saponaria (NemaQ®)+TX, Reynoutria sachalinensis (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX, E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (*Aphelinus*-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline *cucumeris*®)+TX, *Amblyseius fallacis* (*Fallacis*®)+TX, *Amblyseius swirskii* (Bugline *swirskii*®+TX, Swirskii-Mite®)+TX, *Amblyseius womersleyi* (Womer-Mite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (*Encarsia* Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline E®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline Hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline M®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline C®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline I®)+TX, *Orius laevigatus* (Thripor-L®+TX, Oriline I®)+TX, *Orius majusculus* (Oriline M®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline Sf®+TX, Sciarid®+TX, Entonem®)+TX, *Steinernema kraussei* (Nemasys L®+TX, BioNem L®+TX, Exhibitline Srb®)+TX, *Steinernema riobrave* (BioVector@+TX, BioVektor@)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (Tricho- Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, Ferri-phosphate (Ferramol®)+TX, Funnel traps (Trapline Y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline F®)+TX, *Microctonus hyperodae*+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (Sil-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+B®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds of formula I selected from Tables 1 to 42 and P with active ingredients described above comprises a compound selected from Tables 1 to 42 and P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 42 and P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 42 and P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

Biological Examples

Example B1: *Bemisia tabaci* (Cotton White Fly): Feeding/Contact Activity

Cotton leaf discs were placed on agar in 24-well microtiter plates and sprayed with aqueous test solutions prepared from 10'000 ppm DMSO stock solutions. After drying the leaf discs were infested with adult white flies. The samples were checked for mortality 6 days after incubation.

The following compounds resulted in at least 80% mortality at an application rate of 200 ppm:
A17, A42 and A43.

Example B2: *Diabrotica Balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:
A2, A8, A29, A38, A39, A42, A43 and A45.

Example B3: *Euschistus heros* (Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm:
A7, A9, A30 and A36.

Example B4: *Frankliniella occidentalis* (Western Flower *Thrips*): Feeding/Contact Activity Sunflower leaf discs were placed on agar in 24-well microtiter plates and sprayed with aqueous test solutions prepared from 10'000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm:
A2, A6, A7 and A37.

Example B5: *Myzus persicae* (Green Peach Aphid): Feeding/Contact Activity

Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm:
A2, A3, A5, A6, A7, A8, A9, A10, A11, A12, A17, A1, A19, A25, A26, A29, A30, A31, A35, A36, A38, A41, A42 and A43.

Example B6: *Myzus persicae* (Green Peach Aphid). Systemic Activity

Roots of pea seedlings infested with an aphid population of mixed ages were placed directly into aqueous test solutions prepared from 10'000 DMSO stock solutions. The samples were assessed for mortality 6 days after placing seedlings into test solutions.

The following compounds resulted in at least 80% mortality at a test rate of 24 ppm:
A2, A3, A4, A5, A6, A7, A8, A9, A11, A12, 15, A17, A18, A19, A22, A24, A25, A26, A31, A36, A37, A41, A42 and A43.

Example B7: *Plutella xylostella* (Diamond Back Moth)

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:
A7, A8, A29, A37, A38, A39, A42, A43 and A45.

Example B8: *Spodoptera littoralis* (Egyqptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm:
A8, A9, A10, A29, A37, A38, A39, A42, A43 and A45.

Example B9: *Spodoptera littoralis* (Egyqptian Cotton Leaf Worm)

Test compounds were applied by pipette from 10'000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm:
A34 and A45.

Example B10: *Tetranychus urticae* (Two-Spotted Spider Mite): Feeding/Contact Activity Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:
A9, A15, A18, A26 and A32.

Example B11: *Thrips tabaci* (Onion *Thrips*) Feeding/Contact Activity

Sunflower leaf discs were placed on agar in 24-well microtiter plates and sprayed with aqueous test solutions prepared from 10'000 ppm DMSO stock solutions. After drying the leaf discs were infested with a *thrips* population of mixed ages. The samples were assessed for mortality 6 days after infestation.

The following compounds resulted in at least 80% mortality at an application rate of 200 ppm:
A8, A19, A29, A42 and A43.

The invention claimed is:
1. A compound of formula I,

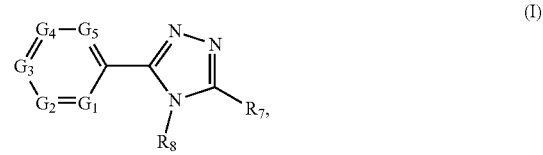

wherein $G_1$ is nitrogen or $CR_2$;

$G_2$ is nitrogen or $CR_3$;

$G_3$ is nitrogen or $CR_4$;

$G_4$ is nitrogen or $CR_5$;

$G_5$ is nitrogen or $CR_6$, with the proviso that not more than 2 nitrogen as G may follow consecutively;

$R_2$, $R_3$, $R_4$, $R_5$ and $R_6$ are, independently from each other, hydrogen, halogen, $C_1$-$C_6$haloalkyl or $C_1$-$C_6$alkyl; or $R_2$, $R_3$, $R_4$, $R_5$ and $R_6$ are, independently from each other, $C_1$-$C_6$haloalkylsulfanyl, $C_1$-$C_6$haloalkylsulfinyl, $C_1$-$C_6$haloalkylsulfonyl, $C_1$-$C_6$alkylsulfanyl, $C_1$-$C_6$alkylsulfinyl, $C_1$-$C_6$alkylsulfonyl, $C_1$-$C_6$alkoxy, $C_1$-$C_6$haloalkoxy, $C_1$-$C_4$haloalkoxy$C_1$-$C_4$alkyl, $C_1$-$C_4$alkoxy$C_1$-$C_4$alkyl, $SF_5$, cyano, $C_3$-$C_6$cycloalkyl$C_1$-$C_4$alkyl or —C(O)$C_1$-$C_6$haloalkyl; or $R_2$, $R_3$, $R_4$, $R_5$ and $R_6$ are, independently from each other, $C_3$-$C_6$cycloalkyl which can be mono- or polysubstituted by substituents selected from the group consisting of halogen, cyano, $C_1$-$C_4$haloalkyl and $C_1$-$C_4$alkyl;

$R_8$ is hydrogen, $C_1$-$C_6$alkyl, $C_1$-$C_6$haloalkyl or $C_1$-$C_4$alkyl substituted by $C_1$-$C_4$alkylsulfanyl;

$R_7$ is a radical selected from the group consisting of formula $Q_1$, $Q_2$, $Q_3$, $Q_4$, $Q_5$, $Q_6$, $Q_7$, $Q_8$, $Q_9$, $Q_{10}$, $Q_{11}$, $Q_{12}$, $Q_{13}$ and $Q_{14}$

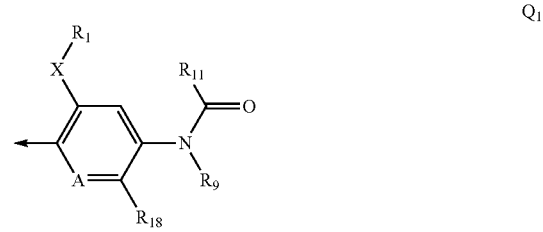

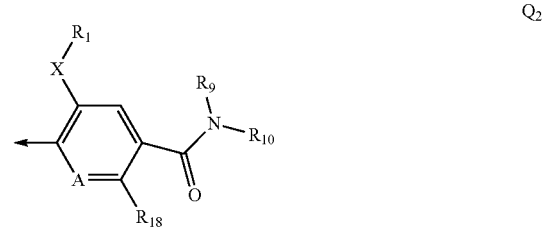

-continued
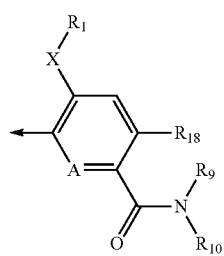
Q3
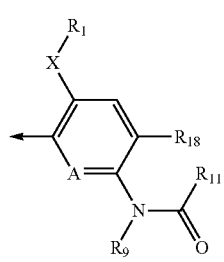
Q4
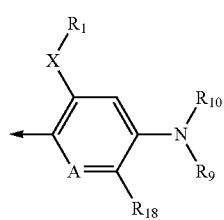
Q5
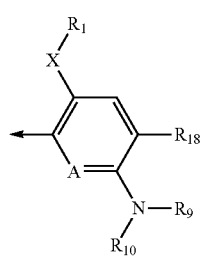
Q6
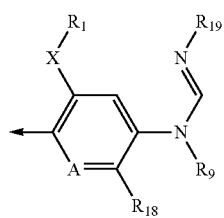
Q7
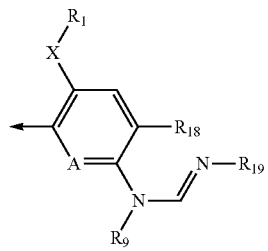
Q8
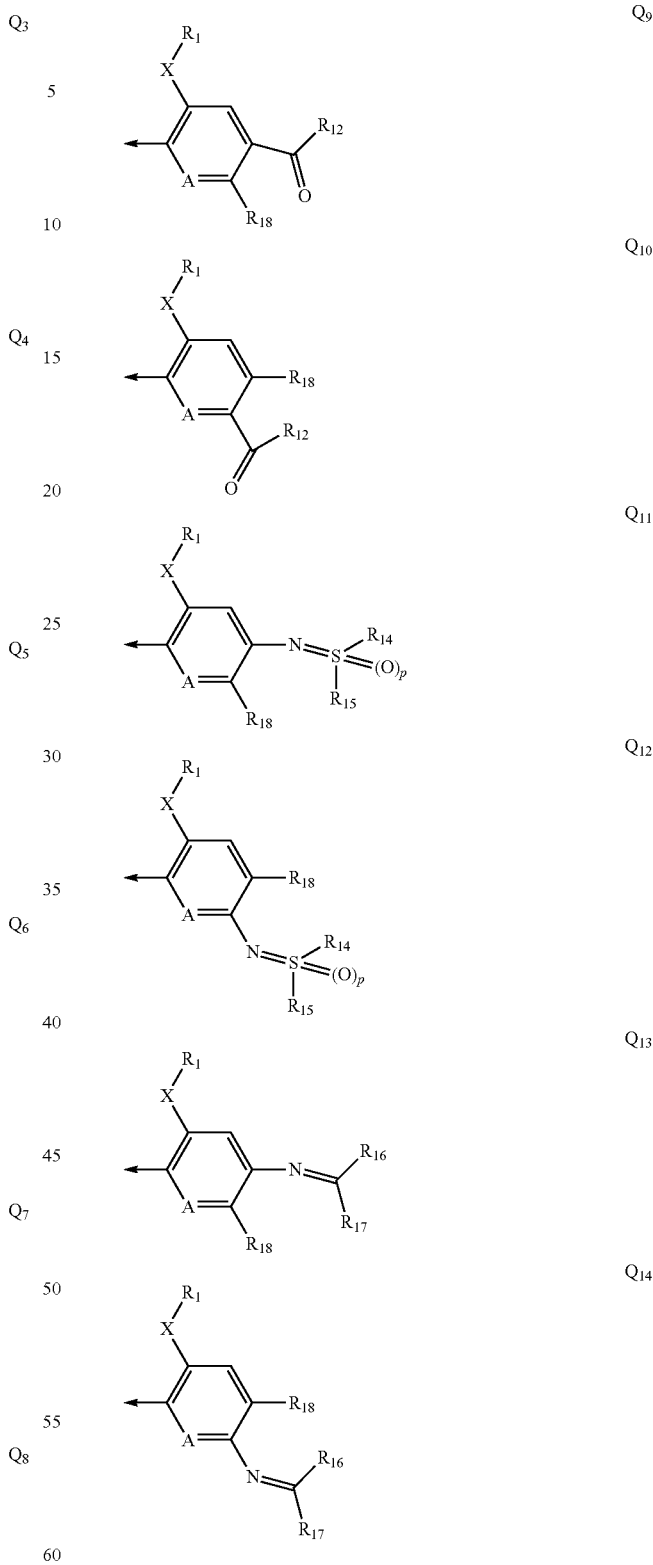
wherein the arrow denotes the point of attachment to the triazole ring;
A represents CH or N;
X is S, SO or SO$_2$;
R$_1$ is C$_1$-C$_4$alkyl or C$_1$-C$_4$haloalkyl; or $R_1$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_1$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;

$R_9$ is hydrogen, $C_1$-$C_6$alkyl, $C_1$-$C_6$haloalkyl, $C_1$-$C_4$alkoxy$C_1$-$C_4$alkyl, hydroxyl, $C_1$-$C_6$alkoxy or $S(O)mR_{13}$; or $R_9$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_9$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;

$R_{10}$ is hydrogen, $C_1$-$C_6$alkyl, cyano, $C_1$-$C_6$alkoxy, $C_1$-$C_6$haloalkoxy, $C_2$-$C_6$alkynyl, $C_2$-$C_6$alkenyl, amino, NH—CN, N—($C_1$-$C_4$alkyl)amino, N—($C_1$-$C_4$ alkyl)N—($C_1$-$C_4$ alkyl)amino, N—($C_3$-$C_6$cycloalkyl)amino, N—($C_1$-$C_4$alkyl)N—($C_3$-$C_6$cycloalkyl)amino, N—($C_1$-$C_4$alkylcarbonyl)amino, N—($C_1$-$C_4$alkyl)N—($C_1$-$C_4$alkylcarbonyl)amino, N—($C_1$-$C_4$ alkyl)N—($C_3$-$C_6$cycloalkylcarbonyl)amino, N—($C_3$-$C_6$cycloalkylcarbonyl)amino, N—($C_1$-$C_4$alkylcarbonyl)N—($C_3$-$C_6$cycloalkyl)amino or —$S(O)mR_{13}$; or $R_{10}$ is $C_1$-$C_4$alkyl mono- or polysubstituted by substituents independently selected from the group Z; or $R_{10}$ is a five to six-membered ring aromatic or heteroaromatic system, said aromatic or heteroaromatic ring system can contain 1 to 4 hetero atoms selected from the group consisting of nitrogen, oxygen and sulfur, with the proviso that each ring system cannot contain more than 2 oxygen atoms and more than 2 sulfur atoms, said five to six-membered ring system can be mono- or polysubstituted by substituents independently selected from the group V;

$R_{11}$ is hydrogen, $C_1$-$C_6$alkyl, $C_1$-$C_6$alkoxy, $C_1$-$C_6$haloalkoxy, amino, N—$C_1$-$C_4$alkylamino, N—($C_1$-$C_4$ alkyl)N—($C_3$-$C_6$ cycloalkyl)amino, N—($C_3$-$C_6$ cycloalkyl)amino or N—($C_1$-$C_4$ alkyl)N—($C_1$-$C_4$ alkyl)amino; or $R_{11}$ is $C_1$-$C_4$alkyl mono- or polysubstituted by substituents independently selected from the group Z; or $R_{11}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{11}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl; or $R_{11}$ is a five- to six-membered aromatic or heteroaromatic ring system, said aromatic or heteroaromatic ring system can contain 1 to 4 hetero atoms selected from the group consisting of nitrogen, oxygen and sulfur, with the proviso that each ring system cannot contain more than 2 oxygen atoms and more than 2 sulfur atoms, said five- to six-membered aromatic or heteroaromatic ring system can be mono- or polysubstituted by substituents independently selected from the group V;

$R_{12}$ is hydrogen, $C_1$-$C_6$ alkyl, $C_1$-$C_6$alkoxy, hydroxyl or $C_1$-$C_6$ haloalkoxy; or $R_{12}$ is $C_1$-$C_4$alkyl mono- or polysubstituted by substituents independently selected from the group Z; or $R_{12}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{12}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;

$R_{13}$ is $C_1$-$C_4$alkyl, $C_1$-$C_4$haloalkyl, N—$C_1$-$C_4$alkylamino, N,N—($C_1$-$C_4$ alkyl)$_2$amino or phenyl; said phenyl can be mono- or polysubstituted by substituents selected from the group consisting of halogen, $C_1$-$C_4$alkyl, cyano, $C_1$-$C_4$haloalkyl and $C_1$-$C_4$alkoxy; or $R_{13}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{13}$ is $C_3$-$C_6$cycloalkyl$C_1$-$C_4$alkyl which can be mono- or polysubstituted by substituents selected from the group consisting of halogen, $C_1$-$C_4$haloalkyl, cyano and $C_1$-$C_4$alkyl;

m is 0, 1 or 2;

$R_{14}$ is hydrogen or $C_1$-$C_6$ alkyl;

$R_{15}$ is hydrogen, $C_1$-$C_6$ alkyl, $C_1$-$C_6$alkoxy, $C_1$-$C_6$ haloalkoxy, amino, N—$C_1$-$C_4$alkylamino or N,N—($C_1$-$C_4$ alkyl)$_2$amino; or $R_{15}$ is $C_1$-$C_4$alkyl mono- or polysubstituted by substituents independently selected from the group Z; or $R_{15}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{15}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;

p is 0 or 1;

$R_{16}$ is hydrogen or $C_1$-$C_6$ alkyl;

$R_{17}$ is hydrogen, $C_1$-$C_6$alkyl, $C_1$-$C_6$haloalkyl, $C_1$-$C_6$alkoxy or $C_1$-$C_6$ haloalkoxy; or $R_{17}$ is amino which can be mono- or disubstituted by substituents selected from the group consisting of cyano, $C_1$-$C_6$alkyl, $C_1$-$C_6$alkoxy, $C_1$-$C_6$haloalkoxy, $C_3$-$C_6$cycloalkyl and $C_3$-$C_6$cycloalkyl-$C_1$-$C_4$alkyl, said $C_3$-$C_6$cycloalkyl and $C_3$-$C_6$cycloalkyl-$C_1$-$C_4$alkyl groups itself can be mono- or polysubstituted by substituents selected from the group consisting of halogen, $C_1$-$C_4$haloalkyl, cyano and $C_1$-$C_4$alkyl; or $R_{17}$ is $C_1$-$C_4$alkyl mono- or polysubstituted by substituents independently selected from the group Z; or $R_{17}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{17}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl; or $R_{17}$ is a five- to six-membered ring aromatic or heteroaromatic ring system, said aromatic or heteroaromatic ring system can contain 1 to 4 hetero atoms selected from the group consisting of nitrogen, oxygen and sulfur, with the proviso that each ring system cannot contain more than 2 oxygen atoms and more than 2 sulfur atoms, said five- to six-membered aromatic or heteroaromatic ring system can be mono- to polysubstituted by substituents independently selected from the group V;

$R_{18}$ is hydrogen, halogen, $C_1$-$C_4$haloalkyl, amino, cyano, $C_1$-$C_4$alkyl, $C_3$-$C_6$cycloalkyl, or is $C_3$-$C_6$cycloalkyl mono-, di- or tri-substituted by substituents selected from the group consisting of halogen, $C_1$-$C_4$haloalkyl, cyano and $C_1$-$C_4$alkyl;

$R_{19}$ is hydrogen, $C_1$-$C_6$alkyl, $C_1$-$C_6$alkoxy, $C_1$-$C_6$haloalkoxy, $C_3$-$C_6$cycloalkyl$C_1$-$C_4$alkyl, $C_3$-$C_6$cycloalkyl;

Z is cyano, halogen, hydroxy, —SH, amino, nitro, $C_1$-$C_4$alkoxy, $C_1$-$C_4$haloalkoxy, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl or phenyl; said phenyl can be mono- or polysubstituted by substituents selected from the group consisting of halogen, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, cyano, $C_1$-$C_4$haloalkyl and $C_1$-$C_4$alkyl; or Z is pyridyl; said pyridyl can be mono- or polysubstituted by substituents selected from the group consisting of halogen, $C_1$-$C_4$ alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, cyano, $C_1$-$C_4$haloalkyl and $C_1$-$C_4$alkyl; or Z is pyrimidyl; said pyrimidinyl can be mono- or polysubstituted by substituents selected from the group consisting of halogen, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, cyano, $C_1$-$C_4$haloalkyl and $C_1$-$C_4$alkyl; and V is cyano, halogen, $C_1$-$C_4$ alkyl, $C_3$-$C_6$ cycloalkyl, $C_1$-$C_4$alkoxy, $C_1$-$C_4$alkoxy$C_1$-$C_4$ alkyl, $C_1$-$C_4$haloalkyl, $C_1$-$C_4$haloalkoxy, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl or $C_1$-$C_4$haloalkylsulfonyl; and agrochemically acceptable salts, stereoismers, enantiomers, tautomers and N-oxides of the compounds of formula I.

2. The compound of claim 1, wherein $R_1$ is methyl, ethyl, n-propyl, i-propyl or cyclopropylmethyl.

3. The compound of claim 1, wherein $G_2$ and $G_5$ are each CH; and $G_4$ is $CR_5$.

4. The compound of claim 1, wherein
$G_1$ is nitrogen;
$G_2$, $G_3$ and $G_5$ are each CH;
$G_4$ is $CR_5$;
$R_5$ is $C_1$-$C_4$haloalkyl;
$R_8$ is $C_1$-$C_4$alkyl;
$R_7$ is selected from the group consisting of $Q_1$, $Q_2$, $Q_3$, $Q_4$, $Q_5$ and $Q_6$;
$R_1$ is $C_1$-$C_4$alkyl; and
$R_{18}$ is hydrogen.

5. The compound of claim 1, wherein
$G_1$ is nitrogen;
$G_2$, $G_3$ and $G_5$ are each CH;
$G_4$ is $CR_5$;
$R_5$ is $C_1$-$C_4$haloalkyl;
$R_8$ is $C_1$-$C_3$alkyl;
$R_7$ is selected from the group consisting of $Q_1$, $Q_2$, $Q_3$, $Q_4$, $Q_5$, $Q_6$, $Q_7$, $Q_9$, $Q_{10}$ and $Q_{11}$;
$R_1$ is $C_1$-$C_4$alkyl; and
$R_9$ is hydrogen, $C_1$-$C_4$alkyl, $C_1$-$C_4$haloalkyl, —S(O)m$R_{13}$; or $R_9$ is cyclopropyl which is optionally substituted by cyano;

$R_{10}$ is hydrogen, $C_1$-$C_6$alkyl, amino, N—($C_1$-$C_4$alkyl) N—($C_3$-$C_6$cycloalkylcarbonyl)amino, N—($C_3$-$C_6$cycloalkylcarbonyl)amino or —S(O)m$R_{13}$; or $R_{10}$ is $C_1$-$C_4$alkyl which can be substituted by cyano;

$R_{11}$ is $C_1$-$C_4$alkoxy or cyclopropyl;
$R_{12}$ is $C_1$-$C_6$alkyl or hydroxyl;
$R_{13}$ is $C_1$-$C_4$alkyl or cyclopropyl;
$R_{14}$ is $C_1$-$C_4$alkyl;
$R_{15}$ is cyclopropyl;
$R_{18}$ is hydrogen or halogen;
$R_{19}$ is $C_1$-$C_4$alkoxy;
m is 2; and
p is 1.

6. The compound of claim 1, wherein
the ring, which is formed by the groups $G_1$, $G_2$, $G_3$, $G_4$ and $G_5$, represents pyridyl, optionally substituted by $C_1$-$C_4$haloalkyl;
$R_7$ is pyridyl, which is substituted by ethylsulfonyl; and which is optionally further substituted by substituents selected from the group consisting of $C_2$-$C_6$alkenyl, —CHO, $C_1$-$C_6$alkylcarbonyl, $C_3$-$C_6$cycloalkylcarbonylamino and $C_3$-$C_6$cycloalkylamino; and
$R_8$ is $C_1$-$C_4$alkyl.

7. The compound of claim 1, wherein $G_1$ is nitrogen and A is N.

8. The compound of claim 1, wherein
$G_1$ is nitrogen;
$G_2$ is $CR_3$;
$G_3$ is $CR_4$;
$G_4$ is $CR_5$;
$G_5$ is $CR_6$; and
A is N.

9. The compound of claim 8, wherein
$R_3$, $R_4$ and $R_6$ are each hydrogen; and
$R_5$ is $CF_3$.

10. The compound of claim 9, wherein $R_8$ is methyl.

11. The compound of claim 10, wherein X is $SO_2$.

12. The compound of claim 11, wherein $R_1$ is ethyl.

13. The compound of claim 8, wherein $R_7$ is selected from the group consisting of $Q_1$, $Q_2$, $Q_3$, $Q_4$, $Q_5$, $Q_6$, $Q_9$ and $Q_{10}$.

14. The compound of claim 8, wherein at least one of $R_3$, $R_4$, $R_5$, and $R_6$ is not hydrogen.

15. The compound of claim 1, wherein $R_7$ is selected from the group consisting of $Q_7$, $Q_8$, $Q_{11}$, $Q_{12}$, $Q_{13}$ and $Q_{14}$.

16. A pesticidal composition, which comprises a pesticidally effective amount of at least one compound of formula I according to claim 1 or, where appropriate, a tautomer thereof, in each case in free form or in agrochemically utilizable salt form, as active ingredient and at least one auxiliary.

17. A method for controlling pests, which comprises applying a composition according to claim 16 to the pests or their environment with the exception of a method for treatment of the human or animal body by surgery or therapy and diagnostic methods practised on the human or animal body.

18. A method for the protection of plant propagation material from the attack by pests, which comprises treating the propagation material or the site, where the propagation material is planted, with a composition according to claim 16.

19. Plant propagation material treated in accordance with the method described in claim 18.

* * * * *